United States Patent
Haidle et al.

(10) Patent No.: US 9,353,066 B2
(45) Date of Patent: May 31, 2016

(54) SUBSTITUTED PHENYL-SPLEEN TYROSINE KINASE (SYK) INHIBITORS

(71) Applicants: Merck Sharp & Dohme Corp., Rahway, NJ (US); Merck Canada Inc., Kirkland (CA)

(72) Inventors: Andrew M. Haidle, Cambridge, MA (US); Jason Burch, Redwood City, CA (US); Daniel Guay, Lachine (CA); Jacques Yves Gauthier, Laval des Rapides (CA); Joel Robichaud, Dollard des Ormeaux (CA); Jean Francois Fournier, Juan les Pins (FR); John Michael Ellis, Needham, MA (US); Matthew Christopher, Brookline, MA (US); Solomon D. Kattar, Arlington, MA (US); Graham F. Smith, Sudbury, MA (US); Alan B. Northrup, Reading, MA (US)

(73) Assignees: Merck Sharp & Dohme Corp., Rahway, NJ (US); Merck Canada Inc., Kirkland, Quebec (CA)

( * ) Notice: Subject to any disclaimer, the term of this patent is extended or adjusted under 35 U.S.C. 154(b) by 0 days.

(21) Appl. No.: 14/422,419

(22) PCT Filed: Aug. 15, 2013

(86) PCT No.: PCT/US2013/055133
§ 371 (c)(1),
(2) Date: Feb. 19, 2015

(87) PCT Pub. No.: WO2014/031438
PCT Pub. Date: Feb. 27, 2014

(65) Prior Publication Data
US 2015/0232428 A1    Aug. 20, 2015

Related U.S. Application Data

(60) Provisional application No. 61/684,979, filed on Aug. 20, 2012.

(51) Int. Cl.

| | |
|---|---|
| *C07D 239/42* | (2006.01) |
| *C07D 403/12* | (2006.01) |
| *A61K 31/506* | (2006.01) |
| *A61K 31/505* | (2006.01) |
| *C07D 401/12* | (2006.01) |
| *C07D 239/47* | (2006.01) |

(52) U.S. Cl.
CPC ............ *C07D 239/42* (2013.01); *A61K 31/505* (2013.01); *A61K 31/506* (2013.01); *C07D 239/47* (2013.01); *C07D 401/12* (2013.01); *C07D 403/12* (2013.01)

(58) Field of Classification Search
CPC ............... C07D 239/42; C07D 403/12; A61K 31/5377; A61K 31/506

USPC ................ 544/122, 331; 514/235.8, 275
See application file for complete search history.

(56) References Cited

U.S. PATENT DOCUMENTS

| | | | |
|---|---|---|---|
| 5,104,877 | A | 4/1992 | Boger |
| 5,710,129 | A | 1/1998 | Lynch et al. |
| 6,248,790 | B1 | 6/2001 | Uckun et al. |
| 6,432,963 | B1 | 8/2002 | Hisamichi et al. |
| 6,589,950 | B1 | 7/2003 | Collingwood et al. |
| 6,770,643 | B2 | 8/2004 | Cox et al. |
| 6,797,706 | B1 | 9/2004 | Hisamichi et al. |
| 6,897,207 | B2 | 5/2005 | Cox et al. |
| 6,897,208 | B2 | 5/2005 | Edwards et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,259,154 | B2 | 8/2007 | Cox et al. |
| 7,276,502 | B2 | 10/2007 | Brenchley et al. |
| 7,557,207 | B2 | 7/2009 | Cooper et al. |

(Continued)

FOREIGN PATENT DOCUMENTS

| | | |
|---|---|---|
| EP | 0426815 B1 | 12/1994 |
| EP | 0877020 A1 | 11/1998 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao
(74) *Attorney, Agent, or Firm* — Eric A. Meade; Anna L. Cocuzzo

(57) ABSTRACT

The invention provides certain substituted phenyl compounds of the Formula (I) or pharmaceutically acceptable salts thereof, wherein $R^1$, $R^2$, $R^3$, $R^4$, $R^{cy}$, and t are as defined herein. The invention also provides pharmaceutical compositions comprising such compounds, and methods of using the compounds for treating diseases or conditions mediated by Spleen Tyrosine Kinase (Syk).

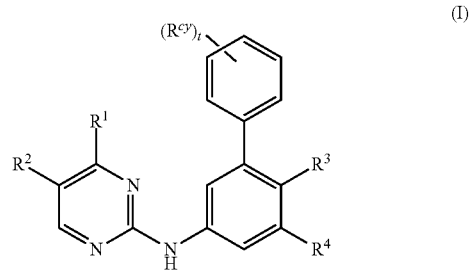

(I)

19 Claims, No Drawings

(56) References Cited

U.S. PATENT DOCUMENTS

| | | |
|---|---|---|
| 7,803,801 B2 | 9/2010 | Kodama et al. |
| 8,551,984 B2 | 10/2013 | Altman et al. |
| 8,735,417 B2 | 5/2014 | Altman et al. |
| 8,759,366 B2 | 6/2014 | Childers et al. |
| 8,796,310 B2 | 8/2014 | Romeo et al. |
| 8,987,456 B2 | 3/2015 | Altman et al. |
| 9,006,444 B2 | 4/2015 | Altman et al. |
| 9,120,785 B2 | 9/2015 | Altman et al. |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0211657 A1 | 9/2006 | Singh et al. |
| 2006/0234483 A1 | 10/2006 | Arak et al. |
| 2006/0247262 A1 | 11/2006 | Baenteli et al. |
| 2007/0004626 A1 | 1/2007 | Masuda et al. |
| 2007/0129362 A1 | 6/2007 | Bhamidipati et al. |
| 2007/0197782 A1 | 8/2007 | Clough et al. |
| 2007/0249645 A1 | 10/2007 | Cochran et al. |
| 2011/0245205 A1 | 10/2011 | Altman et al. |
| 2011/0301175 A1 | 12/2011 | Molteni et al. |
| 2014/0148474 A1 | 5/2014 | Altman et al. |
| 2014/0243336 A1 | 8/2014 | Altman et al. |
| 2014/0249130 A1 | 9/2014 | Deschenes et al. |
| 2015/0148327 A1 | 5/2015 | Haidle et al. |
| 2015/0166486 A1 | 6/2015 | Haidle et al. |
| 2015/0175575 A1 | 6/2015 | Lim et al. |
| 2015/0191461 A1 | 7/2015 | Machacek et al. |
| 2015/0239866 A1 | 8/2015 | Machacek et al. |

FOREIGN PATENT DOCUMENTS

| | | |
|---|---|---|
| JP | 2004203748 | 12/2002 |
| WO | 03/063794 A2 | 8/2003 |
| WO | WO03078404 A1 | 9/2003 |
| WO | 2004/041810 A1 | 5/2004 |
| WO | WO2004080463 A1 | 9/2004 |
| WO | WO2005013996 A2 | 2/2005 |
| WO | WO2005026158 A1 | 3/2005 |
| WO | WO2005033103 A1 | 4/2005 |
| WO | WO2006004865 A1 | 1/2006 |
| WO | WO2006028833 A1 | 3/2006 |
| WO | WO2006050480 A2 | 5/2006 |
| WO | WO2006068770 A1 | 6/2006 |
| WO | WO2006078846 A1 | 7/2006 |
| WO | WO2006093247 A1 | 9/2006 |
| WO | WO2006129100 A1 | 12/2006 |
| WO | WO2006133426 A2 | 12/2006 |
| WO | WO2006135915 A2 | 12/2006 |
| WO | WO2007009681 A1 | 1/2007 |
| WO | WO2007009773 A1 | 1/2007 |
| WO | WO2007028445 A1 | 3/2007 |
| WO | WO2007042298 A1 | 4/2007 |
| WO | WO2007042299 A1 | 4/2007 |
| WO | WO2007070872 A1 | 6/2007 |
| WO | WO2007085540 A1 | 8/2007 |
| WO | WO2007120980 A2 | 10/2007 |
| WO | 2008/024634 A1 | 2/2008 |
| WO | WO2009031011 A2 | 3/2009 |
| WO | WO2009084695 A1 | 7/2009 |
| WO | WO2009097287 A1 | 8/2009 |
| WO | WO2009102468 A1 | 8/2009 |
| WO | WO2009131687 A2 | 10/2009 |
| WO | WO2009136995 A2 | 11/2009 |
| WO | WO2009145856 A1 | 12/2009 |
| WO | WO2010068257 A1 | 6/2010 |
| WO | WO2010068258 A1 | 6/2010 |

OTHER PUBLICATIONS

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Pamuk et al., Spleen tyrosine kinase inhibition in the treatment of autoimmune, allergic and autoinflammatory diseases, Arthritis Research & Therapy, (2010), 12:222, pp. 1-11.*

International Search Report and Written Opinion for PCT/US13/55133 mailed Feb. 7, 2014.

Yamamoto, et al, "The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents", The Journal of Pharmacology and Experimental Therapeutics, 2003, pp. 1174-1181, vol. 306(3).

European Search Report for PCT/US2013/055133 dated Mar. 1, 2016.

* cited by examiner

SUBSTITUTED PHENYL-SPLEEN TYROSINE KINASE (SYK) INHIBITORS

CROSS REFERENCE TO RELATED APPLICATIONS

This application is a U.S. National Phase application under 35 U.S.C. §371 of PCT Application No. PCT/US2013/055133, filed Aug. 15, 2013, which claims priority under 35 U.S.C. §119(e) from U.S. Provisional Application No. 61/684,979, filed Aug. 20, 2012.

FIELD OF THE INVENTION

The present invention relates to certain substituted phenyl compounds of the Formula (I) (also referred to herein as the "compounds of the Formula (I)" or "compounds of Formula (I)") which are inhibitors of Spleen Tyrosine Kinase (Syk) activity, or are prodrugs thereof. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signalling cascade. In mast cells, for example, the early sequence of $Fc_{epsilon}RI$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, *Journal of Allergy and Clinical Immunology* (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 *Nature* 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

SUMMARY OF THE INVENTION

The present invention provides novel compounds that are potent inhibitors of Syk, or are prodrugs thereof, as well as pharmaceutical compositions containing them. As Syk inhibitors compounds of Formula (I) are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or condition mediated by Syk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of cancer pain or an inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 F atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "carbocycle," as used herein, refers to a fully saturated, partially unsaturated, or an aromatic monocyclic or multicyclic ring system comprising comprising from about 6 to 14 carbon atoms. In one embodiment, an aryl group contains from 3 to 10 carbon atoms ($C_3$-$C_{10}$ carbocycle). Non-limiting examples of carbocyclic groups include cycloalkyl and aryl groups, as defined herein. In specific embodiments, the carbocylic groups are selected from cyclopropyl, cyclobutyl, cyclopentyl, cyclohexyl, phenyl, indanyl, napthyl, and tetrahydronapthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocyclyl as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl," as used herein, refers to a non-aromatic saturated or partially saturated monocyclic or multicyclic ring system containing 3 to 11 ring atoms, wherein from 1 to 4 of the ring atoms are independently O, S, or N, and the remainder of the ring atoms are carbon atoms. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. A heterocyclyl group can be joined to the rest of the molecule via a ring carbon or ring nitrogen atom. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms.

The term "spiroheterocyclic ring," as used herein, refers to a bicyclic heterocyclic ring as defined above wherein the two rings are joined through a common ring carbon atom. In one embodiment, a spiroheterocyclic ring is a 8- to 11-membered ring system containing one to three heteroatoms, e.g., one to two heteroatoms, selected from the group consisting of N and O. Non-limiting examples of spiroheterocyclic rings include 1,9-diazaspiro[5.5]undecane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa-7-azaspiro[4.5]decane; 1,4-dioxa-7-azaspiro[4.5]decane; 1,4-dioxa-8-azaspiro[4.5]decane, and 1,4-dioxaspiro[4.5]decane.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

When a structural formula specifies a methylene or substituted methylene group in parentheses which bridges two adjacent moieties, and a variable to indicate the number of such methylenes, when such variable is 0, it is meant that such methylene group is replaced by a bond. By way of example, in the group of the formula

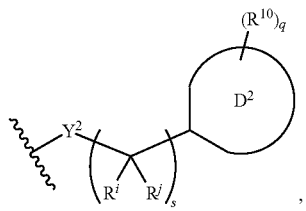

when s is 0, it is meant that $Y^2$ is bonded to $D^2$ as shown in the following structural formula:

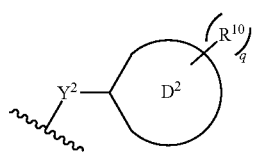

In the structural formula for the group

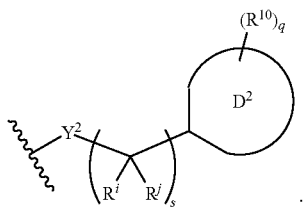

for $R^{cy}$, it will be understood that the moiety $R^{10}$ may be substituted on the ring carbon atom which joins $D^2$ to the remaining structure of group, where the valency of such ring carbon atom permits substitution. By way of example in some embodiments, the group $R^{cy}$ has the formula

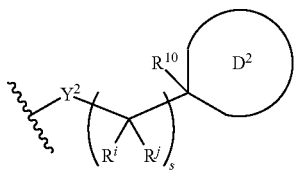

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $R^1$, $R^2$, $R^3$, $R^4$, $R^{cy}$, $C^y$, and t are as defined below. Described below are embodiments of the compound of Formula (I). The compounds of the Formulas (IA) and (IB), shown below, are embodiments of the compound of Formula (I).

In embodiment no. 1, the invention provides a compound of Formula (I),

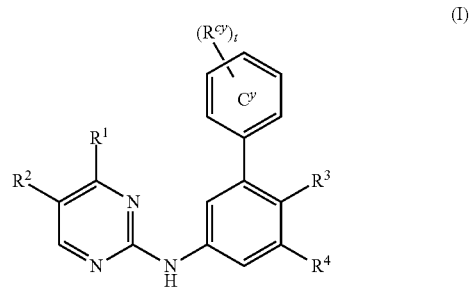

or a pharmaceutically acceptable salt thereof, wherein
$R^1$ is selected from the group consisting of $C_1$-$C_6$ alkyl, $C_1$-$C_3$ fluoroalkyl, $C_1$-$C_3$ alkoxy, $C_3$-$C_6$ cycloalkyl, 2,8-diazaspiro[4.5]decyl, and 4-piperidinyloxy;
$R^2$ is selected from the group consisting of H, methyl, methoxy, —$CHF_2$, —$CF_3$, halo, and cyano;

$R^3$ is selected from the group consisting of H, $C_1$-$C_3$ alkyl, and halo;

$R^4$ is selected from the group consisting of H, $C_1$-$C_3$ alkyl, $C_1$-$C_3$ fluoroalkyl, $C_1$-$C_3$ alkoxy, $C_3$-$C_6$ cycloalkyl, halo, —N($R^{4a}$)$_2$, —N($R^{4a}$)C(O)$R^{4b}$, —N($R^{4a}$)C(O)N($R^{4a}$)$_2$, —N($R^{4a}$)S(O)$_2$$R^{4b}$, —N($R^{4a}$)C(O)N($R^{4a}$)—S(O)$_2$$R^{4a}$, —CO$_2$H, and $R^{4c}$, wherein $R^{4c}$ is -G-$R^{4c1}$ or —$R^{4c1}$, wherein
G is a —O—, —C(O)—, or —CH$_2$—;
$R^{4c1}$ is:
(i) a 5-8 membered heterocyclyl containing 1 nitrogen atom and 0 to 1 additional heteroatoms selected from the group consisting of N, O, and S.
(ii) a 9-10 membered spiroheterocyclyl containing 1 nitrogen atom and 0 to 1 additional heteroatoms selected from the group consisting of N, O, and S; and
(iii) phenyl;
wherein said $R^{4c1}$ is unsubstituted or substituted by 1 to 2 $R^{4c2}$ moieties selected from the group consisting of $C_1$-$C_3$ alkyl, —S(O)$_2$—($C_1$-$C_3$ alkyl), —CH$_2$—O—($C_1$-$C_3$ alkyl), —CH$_2$—N($C_1$-$C_3$ alkyl)$_2$, and —CH$_2$O—C(O)—($C_1$-$C_3$ alkyl), or optionally, wherein 2 $R^{4c2}$ moieties are geminally substituted on a common ring carbon, the 2 $R^{4c2}$ moieties together with said ring carbon form a carbonyl;

each $R^{4a}$ is independently selected from the group consisting of H, $C_1$-$C_3$ alkyl, and $C_1$-$C_3$ fluoroalkyl;

$R^{4b}$ is selected from the group consisting of $C_1$-$C_3$ alkyl and phenyl, wherein said phenyl is unsubstituted or substituted by one halo;

t is 0, 1, 2, or 3;

each $R^{cy}$ is independently selected from the group consisting of:

A. a group of the formula

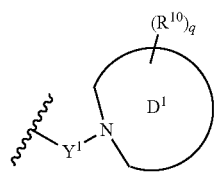

wherein
$Y^1$ is a bond, —(CH$_2$)$_{z1}$—, —S(O)$_2$(CH$_2$)$_{z1}$—, —S(O)$_2$N(H)(CH$_2$)$_{z2}$—, —O(CH$_2$)$_{z2}$—, or —C(O)—;
the subscript z1 is 0, 1, 2, or 3;
the subscript z2 is 2 or 3;
$D^1$ is
(i) a 4- to 9-membered mono- or bicyclic heterocyclic ring optionally containing one to two additional heteroatoms selected from the group consisting of N, O, S, S(O), and S(O)$_2$;
(ii) a 9- to 11-membered spiroheterocyclic ring containing one to two additional heteroatoms selected from the group consisting of N and O;
each $R^{10}$ is independently selected from the group consisting of $C_1$-$C_3$ alkyl, $C_1$-$C_3$ alkoxy, halo, hydroxyl, $C_1$-$C_3$ fluoroalkyl, —(CH$_2$)$_{n5}$CO$_2$$R^g$, hydroxyl($C_1$-$C_3$) alkyl, —(CH$_2$)$_{n5}$OCH$_3$, —C(O)—($C_1$-$C_3$) alkyl, —(CH$_2$)$_{n5}$C(O)N($R^h$)$_2$, —S(O)$_2$—($C_1$-$C_3$) alkyl, —C(O)CH$_2$CN, and —C(O)CH$_2$OH, or wherein when two $R^{10}$ moieties are geminally substituted on a common ring carbon atom of $D^1$, the two geminally substituted $R^{10}$ moieties together with the carbon atom on which they are attached form —C(O)—;
each $R^h$ is independently H, $C_1$-$C_3$ alkyl, $C_3$-$C_6$ cycloalkyl, —CH$_2$CO$_2$H, —CH$_2$C(O)NH$_2$, —S(O)$_2$—$C_1$-$C_3$ alkyl, or —S(O)$_2$—NH$_2$;
the subscript n5 is 0, 1, 2, or 3;
the subscript q is 0, 1, 2, 3, 4, or 5;

B. a group of the formula

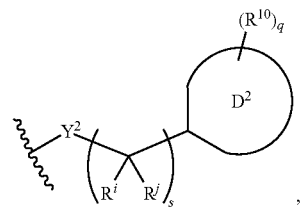

wherein
$Y^2$ is a bond, —C(O)—, —N($R^k$)—, —O—, —C(O)—N($R^k$)—, —S(O)$_2$—N($R^k$)—, or —N($R^k$)—S(O)$_2$—;
$R^k$ is H or $C_1$-$C_3$ alkyl;
each $R^i$ is independently H, $C_1$-$C_3$ alkyl, hydroxyl, —CO$_2$H, or —N(H)C(O)NH$_2$;
each $R^j$ is independently H, $C_1$-$C_4$ alkyl, or cyclopropyl;
the subscript s is 0, 1, 2, 3, 4, or 5; and
$D^2$ is selected from the group consisting of:
(i) a $C_3$-$C_{10}$ carbocycle,
(ii) a 5- to 9-membered mono- or bicyclic heterocyclyl containing 1 or 3 heteroatoms selected from the group consisting of N, O, S, S(O), and S(O)$_2$; and
(iii) a 5- to 6-membered heteroaryl containing 1 to 2 heteroatoms selected from the group consisting of N, O, and S;

C. a group of the formula

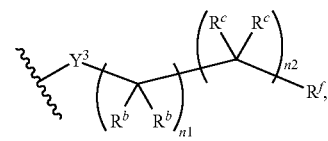

wherein
$Y^3$ is (i) a bond,

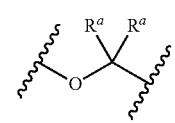

(ii)

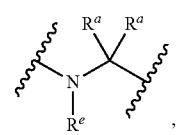

(iii)

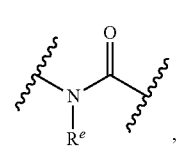

(iv)

-continued

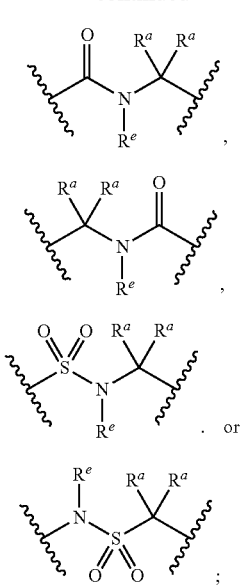

(v)

(vi)

(vii)

(viii)

$R^e$ is H, $C_1$-$C_3$ alkyl, hydroxyl($C_2$-$C_3$) alkyl, or —(CH$_2$)$_{n3}$CN;

each $R^a$ is independently selected from the group consisting of H, fluoro, $C_1$-$C_6$ alkyl, and $C_1$-$C_3$ fluoroalkyl;

each $R^b$ is independently selected from the group consisting of H, hydroxyl, fluoro, $C_1$-$C_6$ alkyl, $C_1$-$C_3$ fluoroalkyl, hydroxy($C_1$-$C_3$) alkyl, —(CH$_2$)$_{n4}$—O—($C_1$-$C_3$) alkyl, —(CH$_2$)$_{n4}$C(O)NH$_2$, —(CH$_2$)$_{n4}$S—($C_1$-$C_3$) alkyl, and —(CH$_2$)$_{n4}$S(O)$_2$—($C_1$-$C_3$) alkyl;

each $R^c$ is independently H or $C_1$-$C_3$ alkyl;

$R^f$ is H, —CHF$_2$, —CF$_3$, —C(O)—($C_1$-$C_3$ alkyl), —CO$_2$R$^g$, —C(O)N(R$^b$)$_2$, —CN, hydroxyl, —N(R$^h$)$_2$, —SO$_3$H, —($C_1$-$C_3$) alkoxy, —O(CH$_2$)$_{n3}$OH;

the subscript n1 is 0, 1, 2, or 3;

the subscript n2 is 0 or 1;

each subscript n3 is independently 2 or 3;

each subscript n4 is independently 1, 2 or 3; and

D. a moiety selected from the group consisting of halo, —S—($C_1$-$C_3$ alkyl), and —S(O)$_2$—($C_1$-$C_3$ alkyl);

each $R^g$ is independently selected from the group consisting of:

(i) H;

(ii) $C_1$-$C_8$ alkyl;

(iii) a group of the formula -M-R$^{CH}$, wherein

M is a bond or —(CH$_2$)$_{n6}$—, wherein the subscript n6 is 1 or 2;

R$^{CH}$ is (a) aryl or $C_3$-$C_6$ cycloalkyl optionally substituted with 1-3 groups independently selected from halo, $C_1$-$C_4$ alkyl, or $C_1$-$C_4$ alkoxy; or (b) a 5- to 6-membered monocyclic heterocycle containing 1 or 2 heteroatoms independently selected from the group consisting of N and O, wherein said heterocycle of R$^{CH}$ is optionally substituted with 1 or 2 groups independently selected from the group consisting of oxo and $C_{1-3}$ alkyl;

(iv) a group of the formula —(CH$_2$)$_{n6}$—R$^m$ or —(CH$_2$)$_2$—O—(CH$_2$)$_2$—R$^m$ wherein R$^m$ is —CO$_2$R$^{m1}$, —C(O)N(R$^{m2}$)$_2$, or —O(CO)R$^{m1}$;

R$^{m1}$ is $C_1$-$C_4$ alkyl; and

R$^{m2}$ is H or $C_1$-$C_4$ alkyl;

(v) a group of the formula —(CH$_2$)$_2$—R$^n$,

R$^n$ is —OH, —O—($C_1$-$C_4$ alkyl), —O—(CH$_2$)$_2$—O—($C_1$-$C_4$ alkyl), —NH$_2$, —N(H)($C_1$-$C_4$ alkyl) or —N($C_1$-$C_4$ alkyl)$_2$;

(vi) a group of the formula

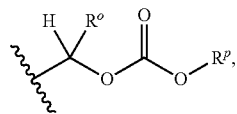

wherein

R$^o$ is H or $C_1$-$C_4$ alkyl; and

R$^p$ is $C_1$-$C_4$ alkyl, $C_3$-$C_6$ cycloalkyl, or phenyl; and, (vii) a group of the formula

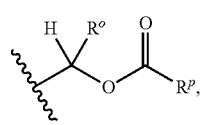

wherein R$^o$ and R$^p$ are as set forth above.

In embodiment no. 2, the invention provides a compound of Formula (I) wherein subscript t is 1 or 2 and at least one R$^{cy}$ is a group of the formula

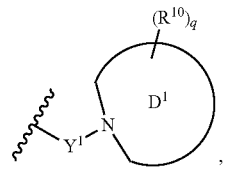

wherein $Y^1$, $D^1$, $R^{10}$, and q are as described in embodiment no. 1.

In embodiment no. 3, the invention provides a compound of Formula (I) wherein R$^{cy}$ is as set forth in embodiment no. 2, and $D^1$ is selected from the group consisting of the following:

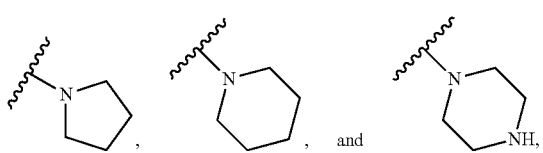

wherein $D^1$ is unsubstituted or substituted by 1 to 2 $R^{10}$ moieties.

In embodiment no. 4, the invention provides a compound of Formula (I), wherein R$^{cy}$ is as set forth in embodiment no. 2 or 3, wherein $Y^1$ is a direct bond, —S(O)$_2$—, —S(O)$_2$(CH$_2$)$_2$—, or —O(CH$_2$)$_2$—.

In embodiment no. 5, the invention provides a compound of Formula (I), wherein wherein t is 1 or 2 and at least one R$^{cy}$ is a group of the formula

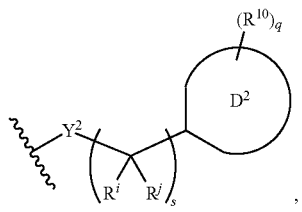

wherein $Y^2$, $D^2$, $R^i$, $R^j$, $R^{10}$, s and q are as set in embodiment no. 1.

In embodiment no. 6, the invention provides a compound of Formula (I) wherein $R^{cy}$ is as set forth in embodiment no. 5, and $D^2$ is selected from the group consisting of cyclopropyl, cyclobutyl, cyclopentyl, cyclohexyl, phenyl, napthyl, indanyl, tetrahydrofuryl, tetrahydropyranyl, piperidinyl, imidazolyl, furyl, triazolyl, tetrazolyl, pyridyl, and benzothienyl; wherein $D^2$ is unsubstituted or substituted by 1 to 3 $R^{10}$ moieties, and the remaining variables are as set forth in embodiment no. 1.

In embodiment no. 7, the invention provides a compound of Formula (I) wherein $R^{cy}$ is as set forth in embodiment no. 5, and $D^2$ is selected from the group consisting of cyclopropyl, cyclobutyl, cyclopentyl, cyclohexyl, phenyl, napthyl,

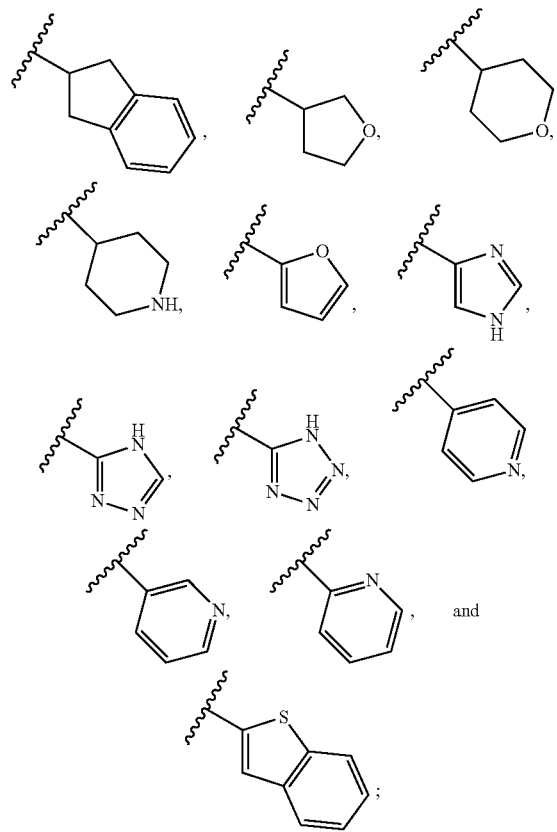

wherein D2 is unsubstituted or substituted by 1 to 2 $R^{10}$ moieties, and the remaining variables are as set forth in embodiment no. 1.

In embodiment no. 8, the invention provides a compound of Formula (I) wherein $R^{cy}$ is as set forth in embodiment nos. 5, 6, or 7, and the moiety

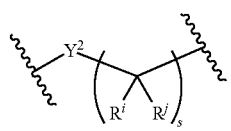

is a direct bond, —C(H)(OH)—, —O—, —OCH$_2$—, —O—CH$_2$CH$_2$—, —N(H)S(O)$_2$—, —N(H)S(O)$_2$CH$_2$—, —S(O)$_2$N(H)—, —S(O)$_2$N(H)CH$_2$—, or —S(O)$_2$N(H)CH$_2$CH$_2$—; and the remaining variables are as set forth in embodiment no. 1.

In embodiment. no. 9, the invention provides a compound of Formula (I), wherein wherein t is 1 or 2 and at least one $R^{cy}$ is a group of the formula

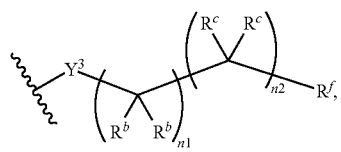

wherein $Y^3$, $R^b$, $R^c$, $R^r$, n1, and n2 are as set forth in embodiment no. 1.

In embodiment no. 10, the invention provides a compound of Formula (I), wherein $R^{cy}$ is —CO$_2$H, —NH$_2$, —CN, —CH$_2$CH$_2$CO$_2$H, —C(H)(OH)—C(H)F$_2$, —S(O)2N(H)CH$_2$CH$_2$CO$_2$H, —OCH$_2$CH$_2$F, —OCH$_3$, —O(CH$_2$)$_3$OH, or —O(CH$_2$)$_4$OH.

In embodiment no. 11, the invention provides a compound of Formula (I), wherein $R^{cy}$ is a moiety selected from the group consisting of halo, —S—(C$_1$-C$_3$ alkyl), —S(O)$_2$—(C$_1$-C$_3$ alkyl).

In embodiment no. 12, the invention provides a compound of Formula (I), wherein $R^{cy}$ is a moiety selected from the group consisting of fluro, chloro, —S—CH$_3$, —S(O)$_2$—CH$_3$.

In embodiment no 13, the invention provides a compound of Formula (IA)

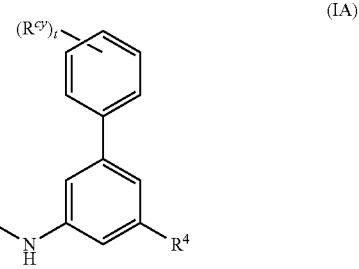

(IA)

wherein $R^1$ is selected from the group consisting of C$_1$-C$_3$ alkyl, C$_1$-C$_3$ fluoroalkyl, and C$_3$-C$_6$ cycloalkyl;

$R^4$ is H or methyl;

the subscript t is 1 or 2; and $R^{cy}$ is as set forth in any one of embodiment nos. 1-12.

In embodiment no. 14, the invention provides a compound of Formula (IA), wherein at least one $R^{cy}$ is —CO$_2$H.

In embodiment no. 15, the invention provides a compound of Formula (IA), wherein the group

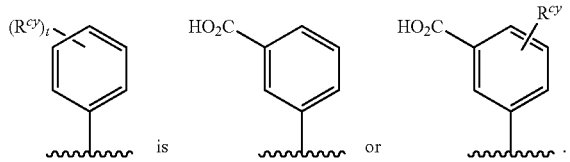

In embodiment no. 16, the invention provides a compound of Formula (IA), wherein the group

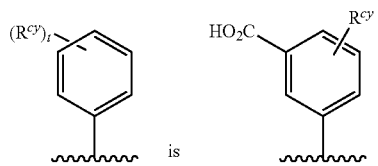

wherein $R^{cy}$ is selected from the group consisting of fluoro, chloro, —CN, phenyl, amino, —O(CH$_2$)$_2$F, —O(CH$_2$)$_3$OH, —O(CH$_2$)$_4$OH, —OCH$_2$C(H)(CH$_3$)$_2$,

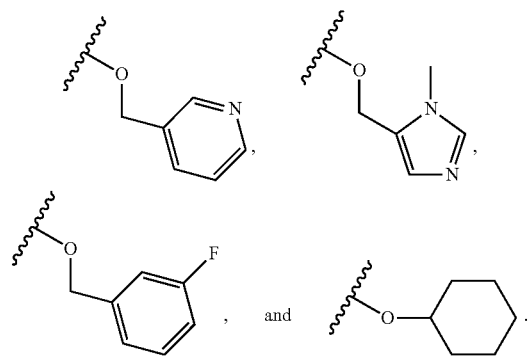

In embodiment no. 17, the invention provides a compound of Formula (IA), wherein $R^1$ is —CF$_3$.

In embodiment no. 18, the invention provides a compound having the Formula (IB),

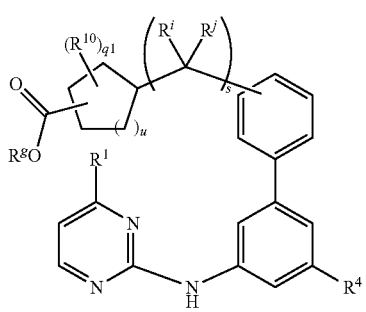

wherein
  $R^1$ is selected from the group consisting of C$_1$-C$_3$ alkyl, C$_1$-C$_3$ fluoroalkyl, and C$_3$-C$_6$ cycloalkyl;
  $R^4$ is selected from the group consisting of H, C$_1$-C$_3$ alkyl and C$_1$-C$_3$ fluoroalkyl;
  $R^i$ is H or hydroxyl;
  $R^j$ is H or C$_1$-C$_3$ alkyl;
  the subscript s is 0, 1, 2, or 3;
  $R^{10}$ is C$_1$-C$_3$ alkyl or hydroxyl;
  the subscript q1 is 0, 1, 2, or 3;
  the subscript u is 0, 1 or 2; and
  $R^g$ is as set forth in embodiment no. 1.

In embodiment no. 19, the invention provides a compound having the Formula (IB), wherein.
  $R^1$ is selected from the group consisting of methyl, —CF$_3$, and cyclopropyl;
  $R^4$ is selected from the group consisting of H and methyl;
  $R^i$ is H or hydroxyl;
  $R^j$ is H or methyl;
  the subscript s is 0 or 1;
  $R^{10}$ is methyl or hydroxyl; and
  q1, u, and $R^g$ is as set forth in embodiment no. 18.

In embodiment no. 20, the invention provides a compound having the Formula (IB), wherein the group

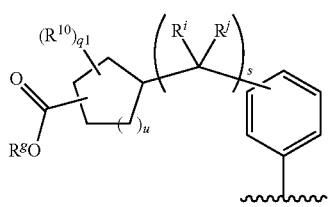

is a group of the formula

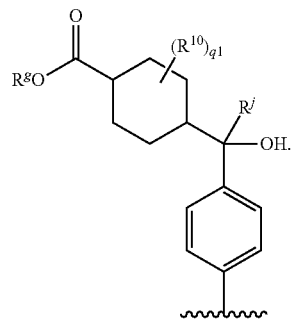

q1 and $R^j$ are as set forth in embodiment no. 18; and
$R^g$ is as set forth in embodiment no. 1.

In embodiment no. 21, the compound has the Formula (I), wherein $R^3$ is selected from the group consisting of H, C$_1$-C$_3$ alkyl, halo, and morpholinyl; and the remaining variables are as set forth in any one of embodiment nos. 1-12.

In embodiment no. 22, the compound has the Formula (I), wherein $R^3$ is H; and the remaining variables are as set forth in any one of embodiment nos. 1-12.

In embodiment no. 23, the compound has the Formula (I) wherein $R^4$ is selected from the group consisting of H, CH$_3$, or a a cyclic group selected from:

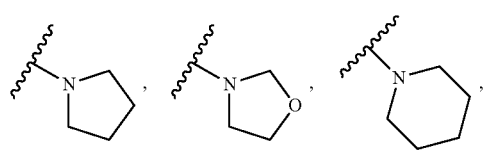

wherein said cyclic group of $R^4$ is unsubstituted or substituted by 1 to 2 $R^{4c2}$ moieties; and the remaining variables are as set forth in any one of embodiment nos. 1-12.

In embodiment no. 24, the compound has the Formula (I) wherein $R^4$ is selected from the group consisting of H and $CH_3$, and the remaining variables are as set forth in any one of embodiment nos. 1-12 and 21-23.

In embodiment no. 25, the compound has the Formula (I) wherein $R^4$ is H or methyl, and the remaining variables are as set forth in any one of embodiment nos. 1-12 and 21-23.

In embodiment no. 26, the invention provides a compound having the Formula (I), (IA), or (IB), wherein $R^g$ is H or $C_1$-$C_3$ alkyl; and wherein the remaining variables are as described in any one of embodiment nos. 1-25

In embodiment no. 27, the invention provides a compound having the Formula (I), (IA), or (IB), wherein $R^g$ is H; and wherein the remaining variables are as described in any one of embodiment nos. 1-25.

In embodiment no. 28, the compound is selected from any one of the compounds described in Examples 1-4.

In embodiment no. 29, the compound is selected from any one of the following compounds or a pharmaceutically acceptable salt thereof:

4-{[(3'-methyl-5'-{[4-(trifluoromethyl)pyrimidin-2-yl]amino}biphenyl-3-yl)sulfonyl]amino}benzoic acid;
4-methoxy-3'-methyl-5'-{[4-(trifluoromethyl)pyrimidin-2-yl]amino}biphenyl-3-carboxylic acid;
N-[(3'-methyl-5'-{[4-(trifluoromethyl)pyrimidin-2-yl]amino}biphenyl-3-yl)sulfonyl]-beta-alanine;
4-(2-fluoroethoxy)-3'-methyl-5'-{[4-(trifluoromethyl)pyrimidin-2-yl]amino}biphenyl-3-carboxylic acid;
4-{[(3'-methyl-5'-{[4-(trifluoromethyl)pyrimidin-2-yl]amino}biphenyl-3-yl)sulfonyl]amino}butanoic acid;
3'-methyl-4-(pyridin-3-ylmethoxy)-5'-{[4-(trifluoromethyl)pyrimidin-2-yl]amino}biphenyl-3-carboxylic acid;
3'-methyl-4-[(1-methyl-1H-imidazol-5-yl)methoxy]-5'-{[4-(trifluoromethyl)pyrimidin-2-yl]amino}biphenyl-3-carboxylic acid;
4-(4-hydroxybutoxy)-3'-methyl-5'-{[4-(trifluoromethyl)pyrimidin-2-yl]amino}biphenyl-3-carboxylic acid;
4-(3-hydroxypropoxy)-3'-methyl-5'-{[4-(trifluoromethyl)pyrimidin-2-yl]amino}biphenyl-3-carboxylic acid;
4-[(3-fluorobenzyl)oxy]-3'-methyl-5'-{[4-(trifluoromethyl)pyrimidin-2-yl]amino}biphenyl-3-carboxylic acid;
4-(cyclopropylmethoxy)-3'-methyl-5'-{[4-(trifluoromethyl)pyrimidin-2-yl]amino}biphenyl-3-carboxylic acid;
4-(benzyloxy)-3'-methyl-5'-{[4-(trifluoromethyl)pyrimidin-2-yl]amino}biphenyl-3-carboxylic acid;
4-(cyclohexyloxy)-3'-methyl-5'-{[4-(trifluoromethyl)pyrimidin-2-yl]amino}biphenyl-3-carboxylic acid;
3'-methyl-4-(2-methylpropoxy)-5'-{[4-(trifluoromethyl)pyrimidin-2-yl]amino}biphenyl-3-carboxylic acid;
trans-4-[1-hydroxy-1-(3'-methyl-5'-{[4-(trifluoromethyl)pyrimidin-2-yl]amino}biphenyl-4-yl)ethyl]cyclohexanecarboxylic acid;
(1R)-trans-4-[1-hydroxy-1-(3'-methyl-5'-{[4-(trifluoromethyl)pyrimidin-2-yl]amino}biphenyl-4-yl)ethyl]cyclohexanecarboxylic acid;
(1S)-trans-4-[1-hydroxy-1-(3'-methyl-5'-{[4-(trifluoromethyl)pyrimidin-2-yl]amino}biphenyl-4-yl)ethyl]cyclohexanecarboxylic acid;
3'-methyl-5'-{[4-(trifluoromethyl)pyrimidin-2-yl]amino}biphenyl-3-carboxylic acid;
5-cyano-3'-methyl-5'-{[4-(trifluoromethyl)pyrimidin-2-yl]amino}biphenyl-3-carboxylic acid;
5-fluoro-3'-methyl-5'-{[4-(trifluoromethyl)pyrimidin-2-yl]amino}biphenyl-3-carboxylic acid;
3-{3'-[(4-cyclopropylpyrimidin-2-yl)amino]-5'-methylbiphenyl-4-yl}propanoic acid;
4-chloro-3'-methyl-5'-{[4-(trifluoromethyl)pyrimidin-2-yl]amino}biphenyl-3-carboxylic acid;
4-amino-3'-methyl-5'-{[4-(trifluoromethyl)pyrimidin-2-yl]amino}biphenyl-3-carboxylic acid;
3''-methyl-5''-{[4-(trifluoromethyl)pyrimidin-2-yl]amino}-1,1':4',1''-terphenyl-2'-carboxylic acid;
3'-[(4-methoxypyrimidin-2-yl)amino]-5'-methylbiphenyl-3-carboxylic acid;
N-(4'-[(1R)-2,2-difluoro-1-hydroxyethyl]-5-{[4-(trifluoromethyl)pyrimidin-2-yl]amino}biphenyl-3-yl)acetamide;
3-{3'-[(4-cyclopropylpyrimidin-2-yl)amino]-5'-methylbiphenyl-3-yl}propanoic acid;
trans-4-(1-hydroxy-1-{3'-methyl-5'-[(4-methylpyrimidin-2-yl)amino]biphenyl-4-yl}ethyl)cyclohexanecarboxylic acid;
(1R)-trans-4-(1-hydroxy-1-{3'-methyl-5'-[(4-methylpyrimidin-2-yl)amino]biphenyl-4-yl}ethyl)cyclohexanecarboxylic acid;
(1S)-trans-4-(1-hydroxy-1-{3'-methyl-5'-[(4-methylpyrimidin-2-yl)amino]biphenyl-4-yl}ethyl)cyclohexanecarboxylic acid;
5-cyano-3'-{[4-(trifluoromethyl)pyrimidin-2-yl]amino}biphenyl-3-carboxylic acid;
3-(3'-methyl-5'-{[4-(trifluoromethyl)pyrimidin-2-yl]amino}biphenyl-4-yl)propanoic acid;
3-(3'-methyl-5'-{[4-(trifluoromethyl)pyrimidin-2-yl]amino}biphenyl-3-yl)propanoic acid;
3-(3'-methyl-5'-{[4-(trifluoromethyl)pyrimidin-2-yl]amino}biphenyl-4-yl)propanoic acid;
5-fluoro-3'-{[4-(trifluoromethyl)pyrimidin-2-yl]amino}biphenyl-3-carboxylic acid;
3-(3'-methyl-5'-{[4-(trifluoromethyl)pyrimidin-2-yl]amino}biphenyl-3-yl)propanoic acid;
3-{3'-[(4-methoxypyrimidin-2-yl)amino]-5'-methylbiphenyl-3-yl}propanoic acid;
1-(4'-[(1R)-2,2-difluoro-1-hydroxyethyl]-5-{[4-(trifluoromethyl)pyrimidin-2-yl]amino}biphenyl-3-yl)-3-ethylurea; and
(1R)-1-(3'-Amino-5'-{[4-(trifluoromethyl)pyrimidin-2-yl]amino}biphenyl-4-yl)-2,2-difluoroethanol.

The invention also provides a compound of Formula (I) or a pharmaceutically acceptable salt thereof in purified form.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, severe asthma, asthma exacerbations, airway hyperresponsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, cystic fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) singaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 mg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering Corporation), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity, will generally be in the range of 5 μg to 100 mg/kg body weight of recipient (patient) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. For the treatment of the inflammatory diseases, rheumatoid arthritis, psoriasis, inflammatory bowel disease, COPD, asthma and allergic rhinitis, these additional therapeutic agents include, but are not limited to: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/ or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate).

For the treatment of cancer a compound of Formula (I) may be combined with an one or more additional therapeutic agents which are anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anticancer agents include, but are not limited to, the following: (1) an estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) an androgen receptor modulator such as finasteride and other 5α-reductase inhibitors, nilutamide, flutamide, bicalutamide, liarozole, and abiraterone acetate; (4) a retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) an antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) a prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) an HMG-CoA reductase inhibitor such as lovastatin, simvastatin, pravastatin, atorvastatin, fluvastatin and rosuvastatin; (8) an angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanalane, 5-amino-1-[[3,5-dichloro-4-(4-chlorobenzoyl) phenyl]-methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)

methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697); (9) an inhibitor of inherent multidrug resistance including inhibitors of p-glycoprotein (P-gp), such as LY335979, XR9576, 0C144-093, R101922, VX853 and PSC833 (valspodar); (10) an inhibitor of cell proliferation and survival signaling such as inhibitors of EGFR (for example gefitinib and erlotinib), inhibitors of ERB-2 (for example trastuzumab), inhibitors of IGF 1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as disclosed in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) an agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; and (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable additional therapeutic agents used in cancer therapy that may be combined with compounds of Formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

These combinations are of particular interest in respiratory diseases and are conveniently adapted for inhaled or intranasal delivery.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the disease or condition mediated by Syk.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu=tert-butyl; Ph=phenyl, and Ac=acetyl μl=microliters
AcOH or HOAc=acetic acid
APCI=atmospheric-pressure chemical ionization
aq=aqueous
Bn=benzyl
Boc or BOC=tert-butoxycarbonyl
Bz=benzoyl
Boc=tert-butoxycarbonyl
Calc'd=calculated
Cbz=benyzloxycarbonyl
DCM=dichloromethane:
DMAP=4-Dimethylaminopyridine
DIBAL=diisobutylaluminum hydride
DIEA or Hünig's Base=N,N-diisopropylethylamine
DMA=1,2-dimethylacetamide
DMF=dimethylformamide
DMSO=dimethyl sulfoxide
DTT=dithiothreitol
EDC=1-ethyl-3-(3-dimethylaminopropyl)carbodiimide
EDTA=ethylenediamine tetraacetic acid
ESI=electrospray ionization
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl)uronium hexafluorophosphate
HEX=hexanes
HPLC=high-performance liquid chromatography
HOBt=1-hydroxybenzotriazole
LDA=lithium diisopropylamide
LCMS=liquid chromatography mass spectrometry
min=minute
mg=milligrams
mL=milliliters
mmol=millimoles
Me=methyl
MeOH: methanol
MS=mass spectrometry
NBS=N-bromosuccimide
NMR=nuclear magnetic resonance spectroscopy
Obsv'd=observed
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine ($Et_3N$)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
General Methods Compounds of the Formula (I) can be prepared according to one of the general synthetic schemes procedures set forth in Schemes 1-6 below, and/or by methods similar to those described in the Examples below.

Scheme 1

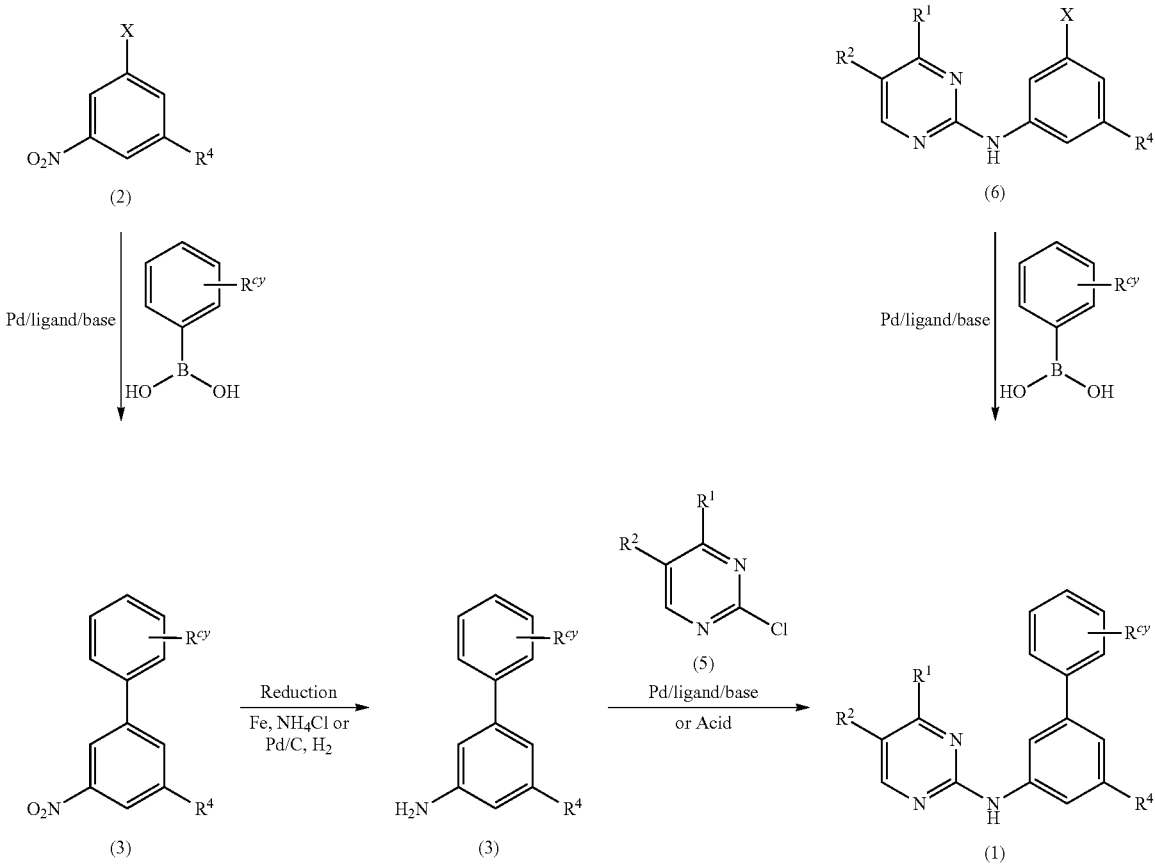

-continued

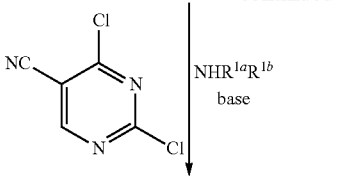

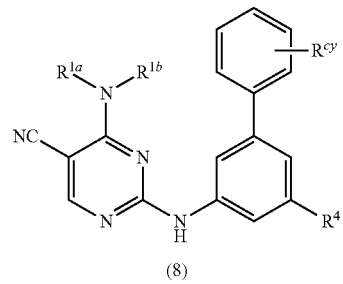

(8)

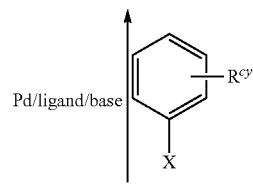

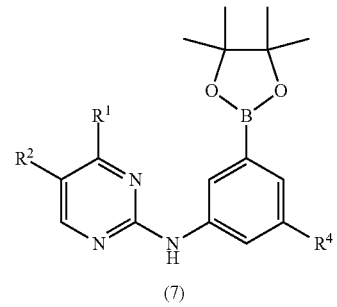

(7)

Preparation of the general core (1) in Scheme 1 begins with Suzuki coupling reaction of known or prepared boronic acids and phenyl halides (2) to yield biphenyl compound (3). Iron-mediated reduction of (3) gives aniline (4). Buchwald-Hartwig coupling or the acid-mediated $S_NAr$ reaction of aniline (4) with known or prepared pyrimidines provides compounds of the general structure of (1). Alternatively, the general core (1) is prepared by Suzuki coupling reaction of compound (6) with known or prepared phenyl boronic acids and also is prepared by Suzuki coupling reaction of boronic acids (7) with known or prepared aryl halides. Compounds (8) are prepared by one-pot $S_NAr$ reaction of aniline (4), 2,4-dichloropyrimidine-5-carbonitrile and known amines.

Scheme 2

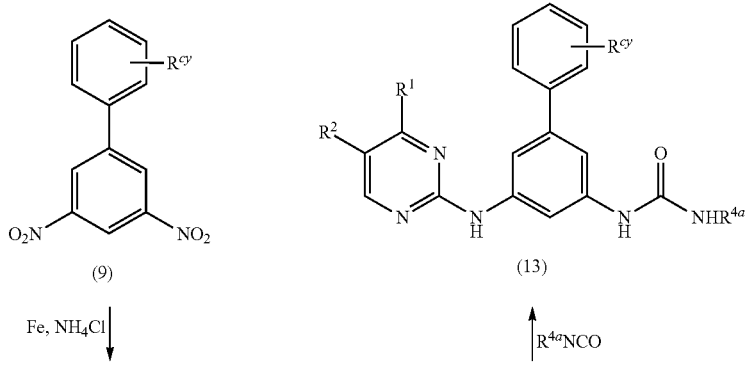

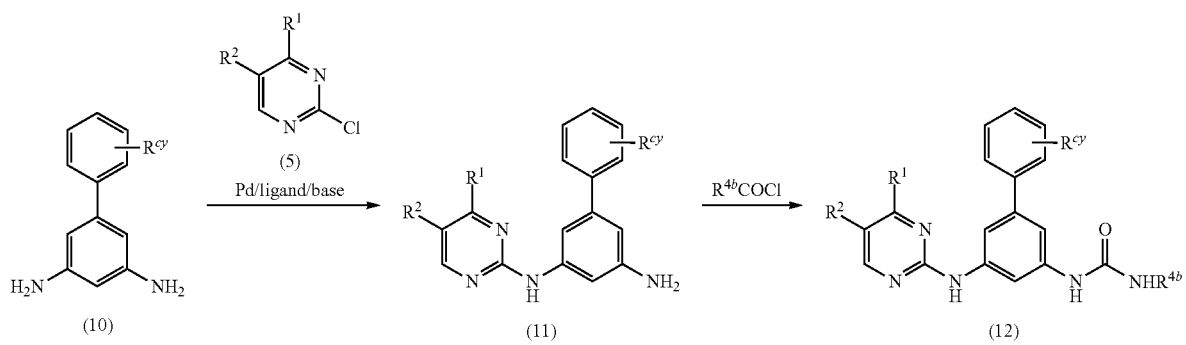

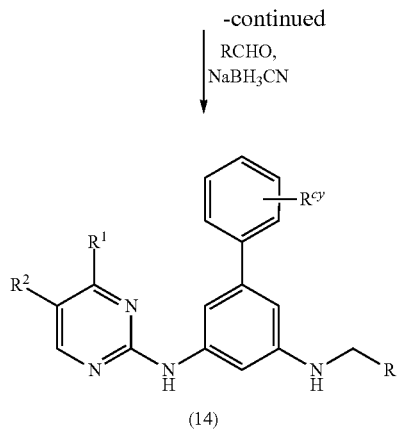
Preparation of the general core (11) in Scheme 2 begins with iron-mediated reduction of nitroarene (9) to provide diamine (10), followed by Buchwald-Hartwig reaction of 2-chloropyrimidine (5) and compound (10). Aniline (11) is then a key intermediate for the formation of compounds with the general structure of (12)-(14).
Scheme 3
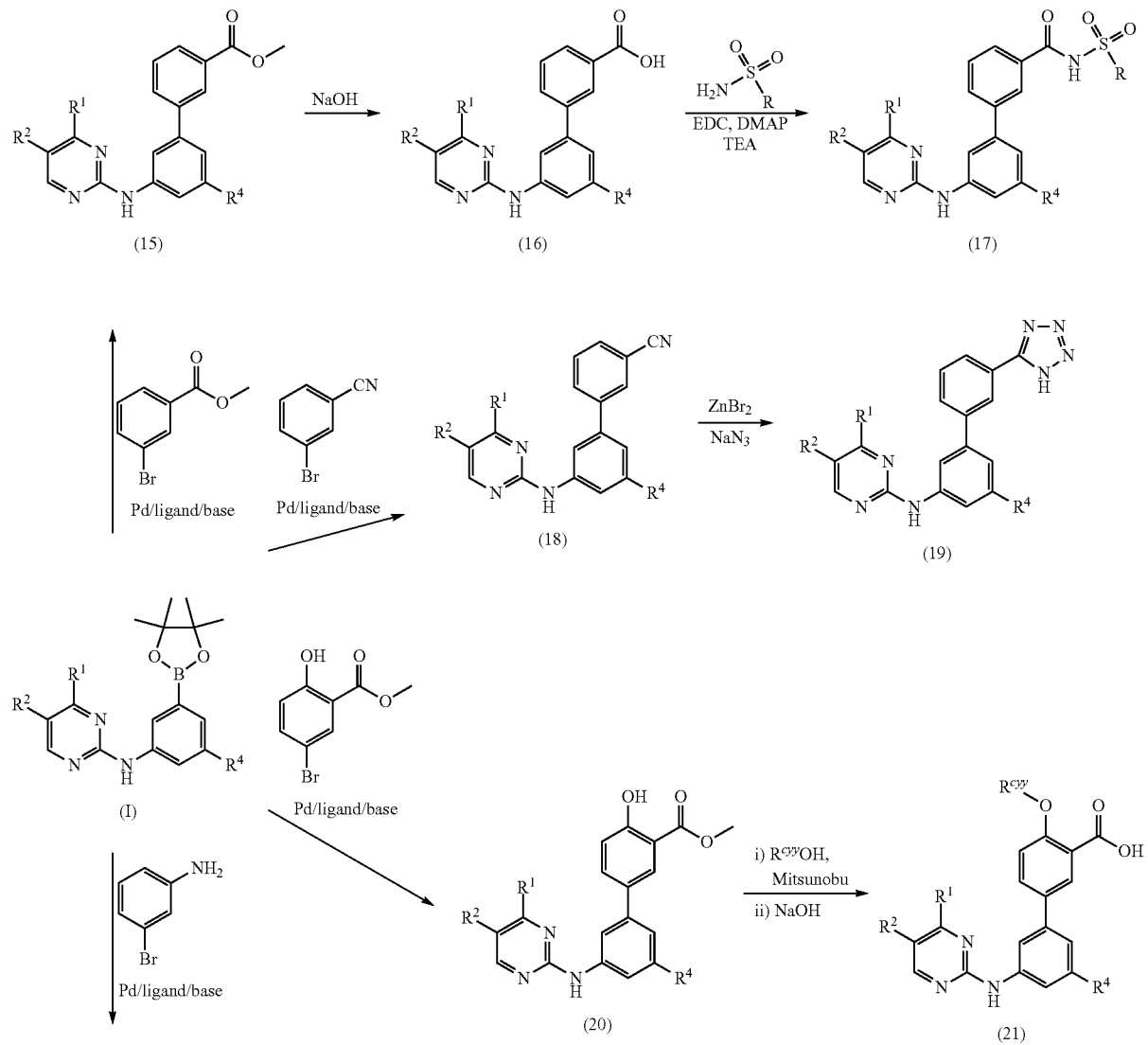

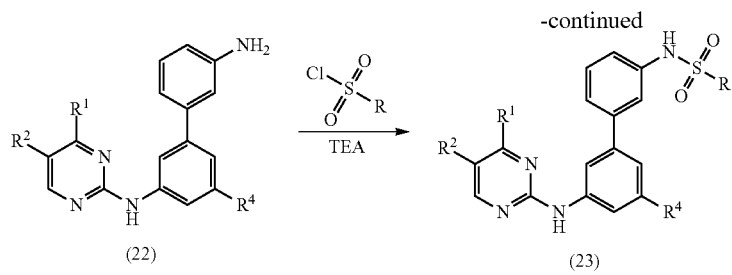

Compounds (15), (18), (20), and (22) are prepared by Suzuki coupling of Intermediate (I) with corresponding phenyl bromides. Ester hydrolysis of (15) followed by sulfonamide acylation of acid (16) yields compound (17). Zinc-mediated click chemistry reaction of nitrile (18) provides tetrazole (19). Mitsunobu O-alkylation followed by ester hydrolysis of phenol ester (20) affords compounds (21). Sulfonamides (23) are prepared by treatment of aniline (22) with known or prepared sulfonyl chlorides.

Scheme 4

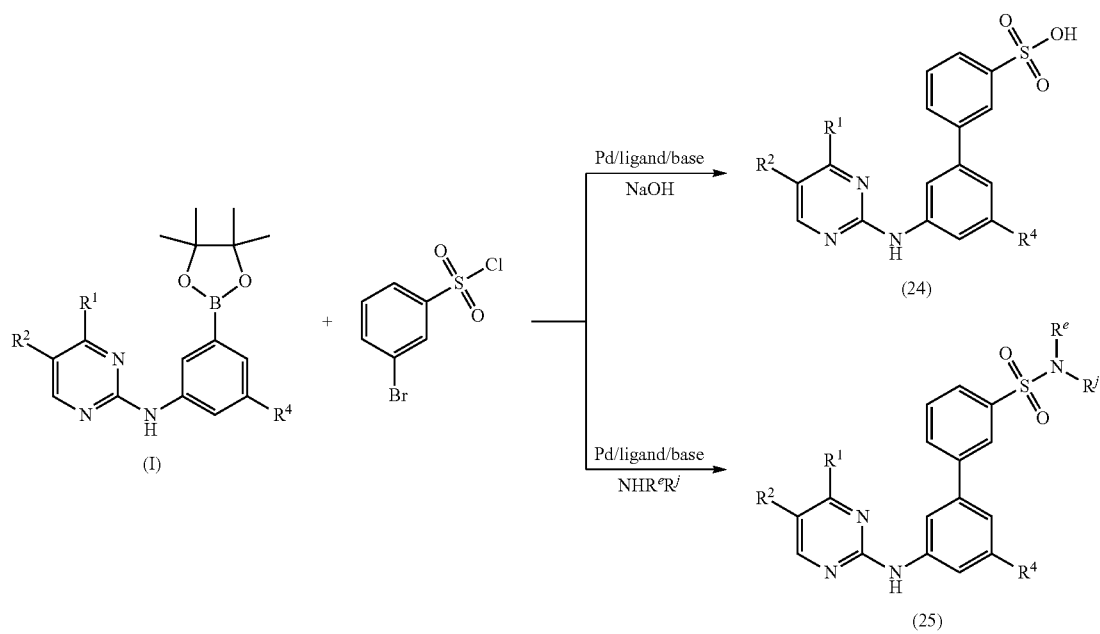

Compound (24) is prepared by Suzuki coupling reaction in the presence of sodium hydroxide. In a similar manner, sulfonamides (25) are prepared by Suzuki coupling in the presence of suitable amines.

Scheme 5
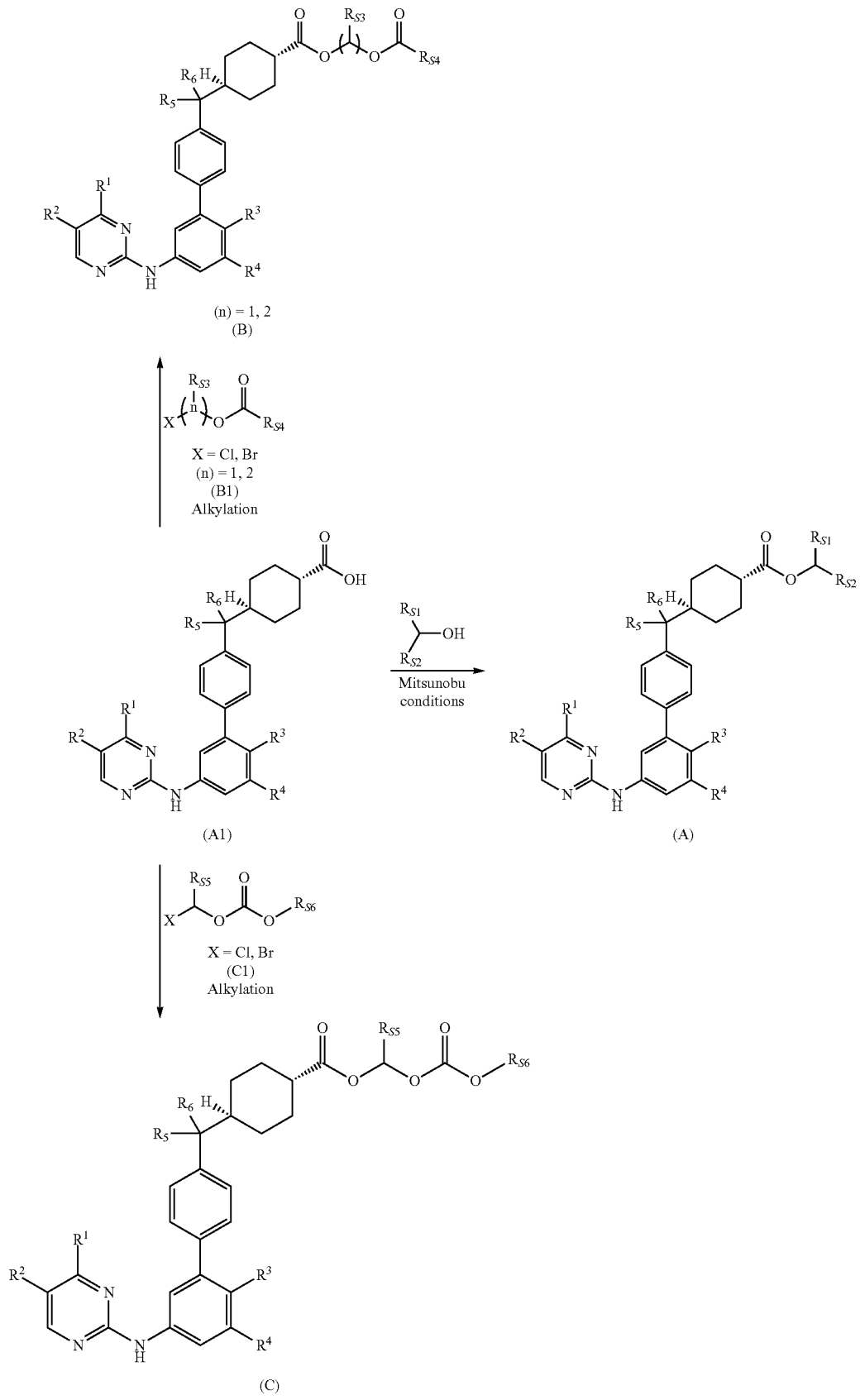

As shown in Scheme 5, compounds of structural subtype (A) are prepared from the trans-cyclohexane carboxylic acid (A1) by a Mitsunobu reaction with various primary and secondary alcohols. Compounds of structural subtype (B) are prepared by the alkylation of the trans-cyclohexane carboxylic acid (A1) by alkyl halides of formula (B1). Compounds of structural subtype (C) are prepared by the alkylation of the trans-cyclohexane carboxylic acid (A1) by alkyl halides of formula (C1).

Scheme 6

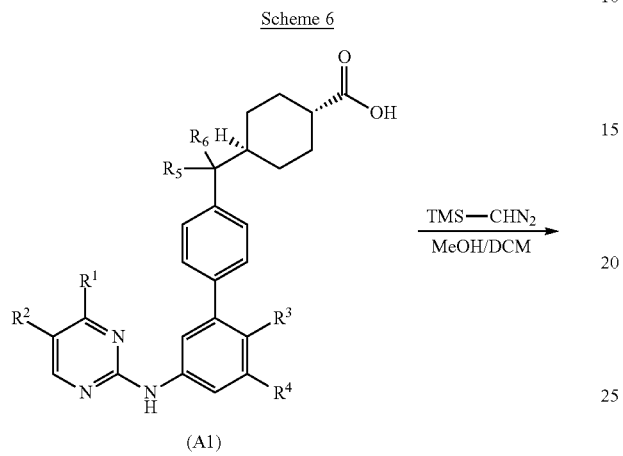

(A1)

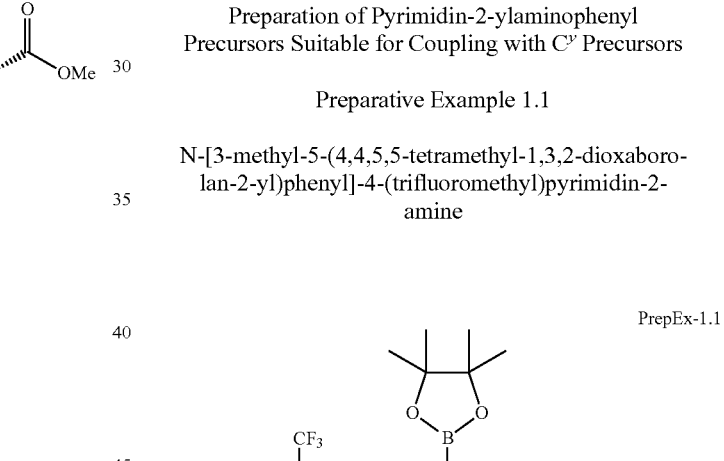

(D)

As shown in Scheme 6, compounds of structural subtype (D) are prepared by the reaction of the trans-cyclohexane carboxylic acid (A1) with trimethylsilyldiazomethane and methanol.

For ease of reference, various intermediates are referred in the Examples below as precursors of various moieties of Compounds of the Formula (I). These moieties are illustrated in the structural formula below.

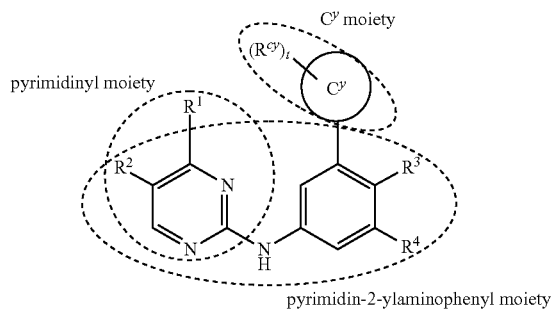

The starting materials and reagents used in preparing compounds described are either available from commercial suppliers or were prepared by literature methods known to those skilled in the art.

These examples are being provided to further illustrate the present invention. The examples provided below are for illustrative purposes only; the scope of the invention is not to be considered limited in any way thereby.

Where the compounds in the examples include the designations "(R) or (S)" or "(R or S)" for a given chiral center in the molecule such designations mean that the compounds were isolated as single enantiomers and the stereochemical configurations of such compounds were not determined Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies stationary phase such as OJ-H or OJ column (stationary phase with particle size of 5 or 10 micron) with a mobile phase of $CO_2$ and a lower alcohol such as methanol or isopropanol.

EXAMPLES

Preparative Example 1

Preparation of Pyrimidin-2-ylaminophenyl Precursors Suitable for Coupling with $C^y$ Precursors Preparative Example 1.1

N-[3-methyl-5-(4,4,5,5-tetramethyl-1,3,2-dioxaborolan-2-yl)phenyl]-4-(trifluoromethyl)pyrimidin-2-amine

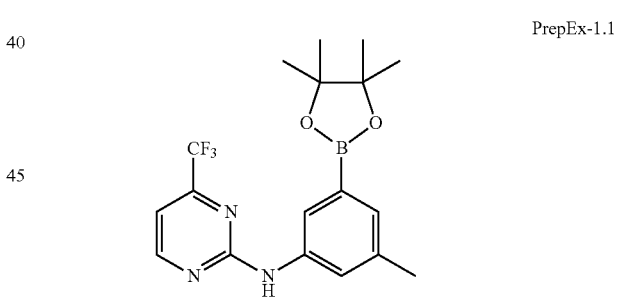

PrepEx-1.1

Step 1:

A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with 2 L of water, then adjusted to pH 7-8 with aqueous sodium bicarbonate solution, followed by extraction with EtOAc (2×2 L). The organic layers were combined, washed with water (2×2 L), dried over anhydrous sodium sulfate and concentrated in vacuo. This resulted in N-(3-bromo-5-methylphenyl)-4-(trifluoromethyl)pyrimidin-2-amine as a light yellow solid. MS(ESI): [M+3]$^+$ 334.0. $^1$H NMR (400 MHz, CDCl$_3$): δ 8.68 (d, J=4.9 Hz, 1H); 7.79 (s, 1H); 7.30 (s, 2H); 7.10-7.06 (m, 2H); 2.36 (s, 3H).

Step 2:

To a solution of N-(3-bromo-5-methylphenyl)-4-(trifluoromethyl)pyrimidin-2-amine (250 g, 753.01 mmol,) in 1,4-dioxane (3 L) was added 4,4,5,5-tetramethyl-2-(4,4,5,5-tetramethyl-1,3,2-dioxaborolan-2-yl)-1,3,2-dioxaborolane (225 g, 885.83 mmol), KOAc (225 g, 2.30 mol) and Pd(dppf)Cl$_2$ (19 g, 25.23 mmol). The resulting solution was heated to reflux overnight. The solid was filtered. The filtrate was decolorized by passing through a silica gel column. The fractions were collected and concentrated in vacuo. This resulted in 110 g pure and 150 g crude product. The crude product was decolorized again with active carbon. This resulted in N-[3-methyl-5-(4,4,5,5-tetramethyl-1,3,2-dioxaborolan-2-yl)phenyl]-4-(trifluoromethyl)pyrimidin-2-amine as a white solid. MS APCI: [M+H]$^+$ m/z 380. $^1$H NMR (400 MHz, CDCl$_3$, ppm): 1.350 (12H, s), 2.386 (3H, s), 6.993-7.006 (1H, d, J=5.2 Hz), 7.385-7.427 (2H, s), 7.636 (1H, s), 7.753 (1H, s), 8.608-8.621 (2H, d, J=5.2 Hz).

Preparative Example 1.2

N-(3-bromo-5-methylphenyl)-4-cyclopropylpyrimidin-2-amine

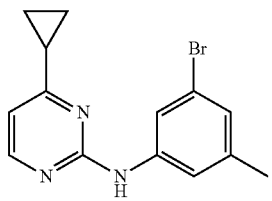

PrepEx 1.2

To a solution of 2-chloro-4-cyclopropyl-pyrimidine (12.5 g, 81 mmol) and 3-bromo-5-methylaniline (18.1 g, 97 mmol) in 1,4-dioxane (100 mL) was added pivalic acid (9.3 mL, 81 mmol). The resulting mixture was heated to reflux and left stirring for 10 hours. The mixture was allowed to cool to room temperature and hexanes were added (80 mL). The slurry was filtered and the filtrate was washed with MeOH to afford a portion of N-(3-bromo-5-methylphenyl)-4-cyclopropylpyrimidin-2-amine. The mother liquors were concentrated, absorbed on silica gel and purified by silica gel column chromatography (EtOAc/Hex) to afford additional N-(3-bromo-5-methylphenyl)-4-cyclopropylpyrimidin-2-amine as a white solid. MS ESI calcd. for C$_{14}$H$_{15}$BrN$_3$ [M+H]$^+$ 304 and 306. found 304 and 306.

Preparative Example 2

Preparation of Pyrimidinyl Precursor

Preparative Example 2.1 tert-Butyl 4-[(2-chloropyrimidin-4-yl)oxy]piperidine-1-carboxylate

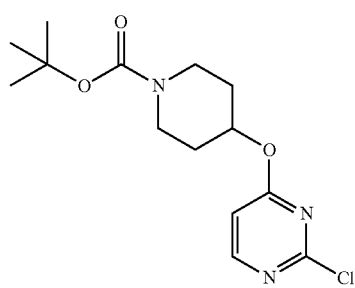

PrepEx 2.1 tert-Butyl 4-hydroxypiperidine-1-carboxylate (1.00 g, 4.97 mmol) was added to a suspension of sodium hydride (60 wt %, 0.238 g, 5.96 mmol) in DMF (16.56 mL) and stirred for 30 minutes at room temperature. 2,4-Dichloropyrimidine (1.11 g, 7.45 mmol) was added to the reaction mixture and stirred for 2 hours at room temperature. The mixture was then diluted with ethyl acetate (100 mL) and washed with 1:1 water:brine (3×). The combined organic layers were dried over sodium sulfate, filtered, and concentrated in vacuo. The residue was purified by silica gel column chromatography (ethyl acetate/hexanes) provided tert-butyl 4-[(2-chloropyrimidin-4-yl)oxy]piperidine-1-carboxylate as a colorless oil.

Preparative Example 3

Preparation of C$^y$ Precursors Suitable for Coupling with Pyrimidin-2-ylaminophenyl Precursors Preparative Example 3.1

Methyl trans-4-[1-(4-bromophenyl)-1-hydroxyethyl]cyclohexanecarboxylate

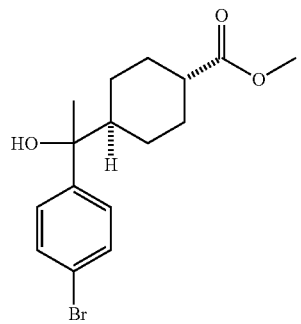

PrepEx 3.1

Isopropylmagnesium chloride-lithium chloride complex (8.35 mL, 10.9 mmol) was added to a cooled solution of 1-bromo-4-iodobenzene (3.07 g, 10.9 mmol) in THF (8 mL) and the resultant solution was stirred for 1 hour at 0° C. Methyl trans-4-acetylcyclohexanecarboxylate (1.00 g, 5.43 mmol) in THF (2 mL) was added to the reaction mixture, stirred for 1 hour at 0° C. and saturated aqueous ammonium chloride was added. The reaction mixture was extracted with ethyl acetate (2×), and then the combined organic layers were dried over Na$_2$SO$_4$, filtered, and concentrated in vacuo. The residue was purified via silica gel column chromatography (ethyl acetate/hexanes) gave methyl trans-4-[1-(4-bromophenyl)-1-hydroxyethyl]cyclohexanecarboxylate as a colorless oil. MS ESI calcd. for C$_{16}$H$_{22}$BrO$_3$[M+H]$^+$341 and 343. found 341 and 343. $^1$H NMR (500 MHz, CDCl$_3$) δ 7.44 (d, J=8.5 Hz, 2H), 7.26 (d, J=8.4 Hz, 2H), 3.63 (s, 3H), 2.16 (tt, J=12.3 Hz, 3.6 Hz, 1H), 2.03-1.91 (m, 2H), 1.84 (m, 1H), 1.60-1.53 (m, 2H), 1.52 (s, 3H), 1.36 (m, 2H), 1.11-0.98 (m, 2H).

Example 3.2

Methyl trans-4-{1-hydroxy-1-[4-(4,4,5,5-tetramethyl-1,3,2-dioxaborolan-2-yl)phenyl]ethyl}cyclohexanecarboxylate

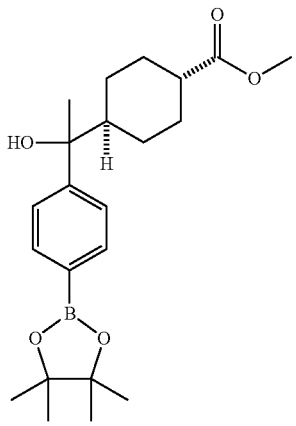

PrepEx 3.2

A mixture of methyl trans-4-[1-(4-bromophenyl)-1-hydroxyethyl]cyclohexanecarboxylate (250 mg, 0.733 mmol), bis(pinacolato)diboron (214 mg, 0.843 mmol), X-Phos (34.9 mg, 0.073 mmol), and $Pd_2(dba)_3$ (33.5 mg, 0.037 mmol) was degassed by sparging with Ar (5 minutes) and then dioxane (5 mL) was added. The reaction mixture was heated to 90° C. for 14 hours, then cooled to room temperature, filtered, and concentrated in vacuo. The residue was purified by silica gel column chromatography (ethyl acetate/hexanes) gave methyl trans-4-{1-hydroxy-1-[4-(4,4,5,5-tetramethyl-1,3,2-dioxaborolan-2-yl)phenyl]ethyl}cyclohexanecarboxylate as a colorless oil. MS ESI calcd. for $C_{22}H_{31}BO_4$ $[M+H-H_2O]^+$ 371, found 371.

Preparative Example 4

Preparation of Alkyl Ester Precursors

Preparative Example 4.1

Methyl N-[(3'-methyl-5'-{[4-(trifluoromethyl)pyrimidin-2-yl]amino}biphenyl-3-yl)carbonyl]glycinate

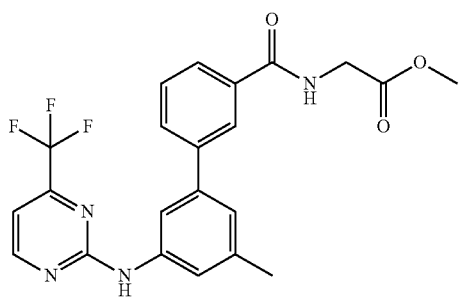

4.1

A suspension of 3'-methyl-5'-{[4-(trifluoromethyl)pyrimidin-2-yl]amino}biphenyl-3-carboxylic acid (80 mg, 0.178 mmol), glycine methyl ester hydrochloride (24.6 mg, 0.196 mmol), DMAP (2.2 mg, 0.018 mmol), EDC (47.7 mg, 0.249 mmol), and triethylamine (0.074 mL, 0.534 mmol) in DMF (4 mL) was stirred for 15 hours at ambient temperature and then heated to 60° C. for 90 minutes. The reaction mixture was cooled to ambient temperature and then charged with HOBT (12.0 mg, 0.078 mmol), glycine methyl ester hydrochloride (24.6 mg, 0.196 mmol), and triethylamine (0.074 mL, 0.534 mmol). The reaction mixture was heated to 60° C. for 5 hours, cooled to ambient temperature, and diluted with diethyl ether (10 mL), ethyl acetate (10 mL), aqueous hydrochloric acid (1 M, 10 mL), and water (5 mL). The layers were separated, and the organic layer was washed with aqueous hydrochloric acid (1 M, 10 mL), aqueous sodium hydroxide (2×10 mL), saturated aqueous sodium bicarbonate (10 mL), and brine (10 mL). The organic layer was dried over sodium sulfate, filtered, and concentrated under reduced pressure to give methyl N-[(3'-methyl-5'-{[4-(trifluoromethyl)pyrimidin-2-yl]amino}biphenyl-3-yl)carbonyl]glycinate which was used without further purification. MS ESI calc'd. for $C_{22}H_{20}F_3N_4O_3$ $[M+H]^+$ 445, found 445.

Example 1

Preparation of Compounds of Formula (I) using the General Methods Illustrated in Scheme 1

Example 1.1

N-(5-methylbiphenyl-3-yl)-4-(piperidin-4-yloxy)pyrimidin-2-amine

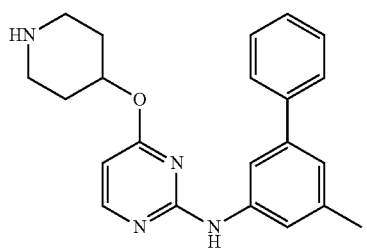

1.1

Step 1: A suspension of 1-bromo-3-methyl-5-nitrobenzene (500 mg, 2.31 mmol), phenyl boronic acid (423 mg, 3.47 mmol), sodium carbonate (491 mg, 4.63 mmol), palladium (II) acetate (26.0 mg, 0.116 mmol) and tri-o-tolylphosphine (70.4 mg, 0.231 mmol) in DME (1 mL) and water (4 mL) was heated to 110° C. for 30 minutes in the microwave reactor. Upon cooling to room temperature, the reaction mixture was diluted with ethyl acetate and filtered through CELITE. The filtrate was concentrated in vacuo, and the resulting residue was purified by silica gel chromatography (ethyl acetate/hexanes) to provide 3-methyl-5-nitrobiphenyl as a yellow solid. $^1$H NMR (400 MHz, $CDCl_3$) $^1$H NMR (400 MHz, $CDCl_3$) δ 8.27 (s, 1H), 8.04 (s, 1H), 7.74 (s, 1H), 7.63 (d, J=7.5 Hz, 2H), 7.51 (t, J=7.5 Hz, 2H), 7.44 (t, J=7.2 Hz, 1H), 2.55 (s, 3H).

Step 2:

Pd/C (10 wt %, 161 mg, 0.151 mmol) was added to a solution of 3-methyl-5-nitrobiphenyl (322 mg, 1.51 mmol) in ethyl acetate (10 mL) and acetic acid (1 mL). The reaction mixture was stirred under an atmosphere of $H_2$ (balloon) for 3 hours and then dichloromethane (5 mL) was added. The reaction mixture was filtered through CELITE, washed with ethyl acetate and concentrated in vacuo. The residue was purified by silica gel column chromatography (ethyl acetate/hexanes) provided 5-methylbiphenyl-3-amine as a brown oil. $^1$H NMR (400 MHz, CDCl$_3$) δ 7.58 (d, J=7.6 Hz, 2H), 7.43 (t, J=7.6 Hz, 2H), 7.34 (t, J=7.3 Hz, 1H), 6.85 (s, 1H), 6.75 (s, 1H), 6.55 (s, 1H), 2.35 (s, 3H).

Step 3:

A solution of tert-butyl 4-[(2-chloropyrimidin-4-yl)oxy]piperidine-1-carboxylate (62.8 mg, 0.2 mmol) and 5-methylbiphenyl-3-amine (36.6 mg, 0.2 mmol) in 0.1 M 1:1 TsOH:dioxane (2.0 mL) was heated to 100° C. overnight. Upon cooling to room temperature, the reaction mixture was concentrated in vacuo. The resulting light yellow solid was triturated in 1:1 dichloromethane:diethyl ether (10 mL). The solid was removed by filtration then dried under vacuum to provide N-(5-methylbiphenyl-3-yl)-4-(piperidin-4-yloxy)pyrimidin-2-amine as a tosylate salt as a light yellow solid. MS ESI calc'd. for $C_{22}H_{25}N_4O$ [M+H]$^+$ 361, found 362. $^1$H NMR (400 MHz, DMSO-d$_6$): δ 10.17 (s, 1H); 8.68 (s, 2H); 8.29 (d, J=6.4 Hz, 1H); 7.76 (s, 1H); 7.63 (d, J=7.9 Hz, 1H); 7.61-7.26 (m, 1H); 7.21 (s, 1H); 7.12 (d, J=8.1 Hz, 2H); 6.43 (d, J=6.4 Hz, 1H); 5.26 (s, 1H); 3.19 (s, 2H); 2.97 (s, 2H); 2.29 (s, 2H); 2.14 (s, 2H); 1.95 (s, 3H).

The following examples in Table 1.1 were prepared in an analogous manner to that described for Example 1.1 using prepared or known pyrimidines in step 3.

Example 1.5

N-[5-(Morpholin-4-yl)biphenyl-3-yl]-4-(trifluoromethyl)pyrimidin-2-amine

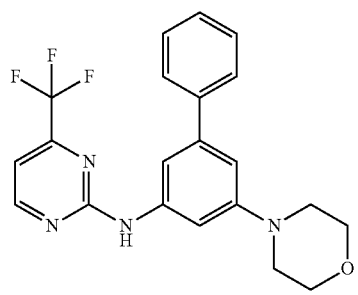

1.5

Step 1:

A suspension of 1-fluoro-3-iodo-5-nitrobenzene (11.0 g, 41.3 mmol), phenyl boronic acid (5.54 g, 45.4 mmol), tri-o-tolylphosphine (1.26 g, 4.13 mmol), Pd(OAc)$_2$ (0.463 g, 2.07 mmol), and sodium carbonate (6.57 g, 62.0 mmol) in 4:1 dimethoxyethane: water (80 mL) was heated to 100° C. in a sealed tube for 6 hours. Upon cooling to ambient temperature, the reaction mixture was diluted with ethyl acetate (500 mL) and filtered through CELITE. The organic layer was washed with brine (500 mL) and concentrated in vacuo. The residue was purified by silica gel column chromatography (ethyl acetate/hexanes) provided 3-fluoro-5-nitrobiphenyl as an off-white solid. $^1$H NMR (400 MHz, CDCl$_3$) δ 8.31 (s, 1H), 7.93 (dt, J=8.1 Hz, 2.1 Hz, 1H), 7.72-7.60 (m, 3H), 7.51 (ddd, J=10.9, 9.9, 5.6 Hz, 3H).

TABLE 1.1

| Ex. No. | R$^1$ | Name | [M + H]+ Calc'd | [M + H]+ Obsv'd | Form(s) |
|---|---|---|---|---|---|
| 1.2 | HN—⟨piperidinyl⟩—O— | N-(biphenyl-3-yl)-4-(piperidin-4-yloxy)pyrimidin-2-amine | 348 | 348 | TFA Salt |
| 1.3 | isopentyl | N-(biphenyl-3-yl)-4-(3-methylbutyl)pyrimidin-2-amine | 318 | 318 | Free Base |
| 1.4 | tert-butyl | N-(biphenyl-3-yl)-4-tert-butylpyrimidin-2-amine | 304 | 304 | Free Base |

Step 2:

A suspension of 1-fluoro-3-iodo-5-nitrobenzene (11.0 g, 41.3 mmol), phenyl boronic acid (5.54 g, 45.4 mmol), tri-o-tolylphosphine (1.26 g, 4.13 mmol), Pd(OAc)$_2$ (0.463 g, 2.07 mmol), and sodium carbonate (6.57 g, 62.0 mmol) in 4:1 dimethoxyethane:water (80 mL) was heated to 100° C. in a sealed tube for 6 hours. Upon cooling to ambient temperature, the reaction mixture was diluted with ethyl acetate (500 mL) and filtered through CELITE. The organic layer was washed with brine (500 mL) and concentrated in vacuo. The residue was purified by silica gel column chromatography (ethyl acetate/hexanes) provided 3-fluoro-5-nitrobiphenyl as an off-white solid. $^1$H NMR (400 MHz, CDCl$_3$) δ 8.31 (s, 1H), 7.93 (dt, J=8.1 Hz, 2.1 Hz, 1H), 7.72-7.60 (m, 3H), 7.51 (ddd, J=10.9, 9.9, 5.6 Hz, 3H).

Step 3:

Pd/C (53.9 mg, 0.051 mmol) was added to a solution of 4-(5-nitrobiphenyl-3-yl)morpholine (144 mg, 0.506 mmol) in ethyl acetate (5 mL) and acetic acid (0.5 mL). The reaction mixture was stirred under H$_2$ atmosphere (1 atm) for 2 hours at room temperature. The reaction mixture was diluted with dichloromethane and filtered through CELITE and washed with ethyl acetate. The resultant solution was concentrated in vacuo to provide 5-(morpholin-4-yl)biphenyl-3-amine as a grey solid which was used without further purification. $^1$H NMR (400 MHz, CDCl$_3$) δ 7.57 (d, J=5.7 Hz, 2H), 7.36 (dd, J=32.4, 26.2 Hz, 3H), 6.58 (s, 1H), 6.49 (s, 1H), 6.27 (s, 1H), 5.13 (s, 2H), 3.89 (s, 4H), 3.21 (s, 4H).

Step 4:

2-Chloro-4-(trifluoromethyl)pyrimidine (23 μL, 0.19 mmol) and TsOH—H$_2$O (29.9 mg, 0.157 mmol) were added to a solution of 5-(morpholin-4-yl)biphenyl-3-amine (40 mg, 0.157 mmol) in dioxane (1.5 mL) and then the reaction mixture was heated to 100° C. for 14 hours. The reaction mixture was diluted with ethyl acetate and washed with saturated NaHCO$_3$ (aq) followed by brine. The aqueous layers were extracted with ethyl acetate, then the combined organic extracts were dried over Na$_2$SO$_4$, filtered, and concentrated in vacuo. The residue was purified by silica gel column chromatography (ethyl acetate/hexanes) provided N-[5-(morpholin-4-yl)biphenyl-3-yl]-4-(trifluoromethyl)pyrimidin-2-amine as a light yellow solid. MS ESI calc'd. for C$_{21}$H$_{20}$F$_3$N$_4$O [M+H]$^+$ 401, found 401. $^1$H NMR (400 MHz, CDCl$_3$): δ 8.66 (d, J=4.9 Hz, 1H); 7.61 (d, J=7.6 Hz, 2H); 7.56 (s, 1H); 7.50-7.34 (m, 4H); 7.23 (s, 1H); 7.05 (d, J=4.9 Hz, 1H); 6.88 (s, 1H); 3.92 (t, J=4.5 Hz, 4H); 3.29 (t, J=4.5 Hz, 4H).

The following examples in Tables 1.2 and 1.3 were prepared in an analogous manner to that described for Example 1.5 using known or commercially available secondary amines or alcohols in step 2 or by using 1-iodo-3-nitrobenzene in step 1 and omitting step 2. In step 4, the pyrimidine moiety was commercially available or was prepared.

TABLE 1.2

| Ex. No. | R$^4$ | Name | [M + H]+ Calc'd | [M + H]+ Obsv'd | Form(s) |
|---|---|---|---|---|---|
| 1.6 | —H | N-biphenyl-3-yl-4-(trifluoromethyl)pyrimidin-2-amine | 316 | 316 | Free Base |
| 1.7 | 2,2-dimethylmorpholin-4-yl | N-[5-(2,2-dimethylmorpholin-4-yl)biphenyl-3-yl]-4-(trifluoromethyl)pyrimidin-2-amine | 429 | 429 | Free Base |
| 1.8 | 2-(methoxymethyl)morpholin-4-yl (racemic) | N-{5-[2-(methoxymethyl)morpholin-4-yl]biphenyl-3-yl}-4-(trifluoromethyl)pyrimidin-2-amine | 445 | 445 | Free Base |
| 1.9 | 2-methylmorpholin-4-yl (racemic) | N-[5-(2-methylmorpholin-4-yl)biphenyl-3-yl]-4-(trifluoromethyl)pyrimidin-2-amine | 415 | 415 | Free Base |

TABLE 1.2-continued

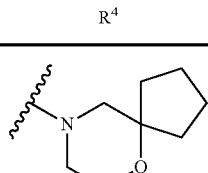

| Ex. No. | R⁴ | Name | [M + H]+ Calc'd | [M + H]+ Obsv'd | Form(s) |
|---|---|---|---|---|---|
| 1.10 | 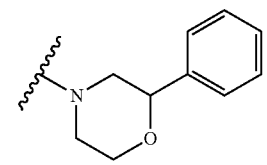 | N-[5-(6-oxa-9-azaspiro[4.5]dec-9-yl)biphenyl-3-yl]-4-(trifluoromethyl)pyrimidin-2-amine | 455 | 455 | Free Base |
| 1.11 | 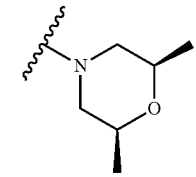 [SMILES: *N1C[C@@H](C)O[C@@H](C)C1]<br>racemic | N-[5-(2-phenylmorpholin-4-yl)biphenyl-3-yl]-4-(trifluoromethyl)pyrimidin-2-amine | 477 | 477 | Free Base |
| 1.12 | 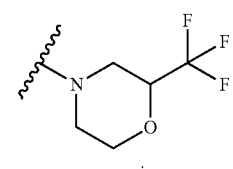 | N-{5-[(meso)-2,6-dimethylmorpholin-4-yl]biphenyl-3-yl}-4-(trifluoromethyl)pyrimidin-2-amine | 429 | 429 | Free Base |
| 1.13 | 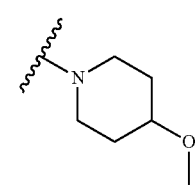 [SMILES: *N1CCC(OC)CC1]<br>racemic | 4-(trifluoromethyl)-N-{5-[2-(trifluoromethyl)morpholin-4-yl]biphenyl-3-yl}pyrimidin-2-amine | 469 | 469 | Free Base |
| 1.14 | 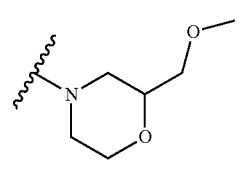 | N-[5-(4-methoxypiperidin-1-yl)biphenyl-3-yl]-4-(trifluoromethyl)pyrimidin-2-amine | 429 | 429 | Free Base |
| 1.15 | <br>(R) or (S)<br>Faster-eluting enantiomer | N-{5-[2-(methoxymethyl)morpholin-4-yl]biphenyl-3-yl}-4-(trifluoromethyl)pyrimidin-2-amine | 445 | 445 | Free Base |

TABLE 1.2-continued

| Ex. No. | R⁴ | Name | [M + H]+ Calc'd | [M + H]+ Obsv'd | Form(s) |
| --- | --- | --- | --- | --- | --- |
| 1.16 | (R) or (S) Slower-eluting enantiomer | N-{5-[2-(methoxymethyl)morpholin-4-yl]biphenyl-3-yl}-4-(trifluoromethyl)pyrimidin-2-amine | 445 | 445 | Free Base |
| 1.17 | | N-(5-thiomorpholin-4-ylbiphenyl-3-yl)-4-(trifluoromethyl)pyrimidin-2-amine | 417 | 417 | Free Base |
| 1.18 | racemic | N-(5-{3-[(dimethylamino)methyl]piperidin-1-yl}biphenyl-3-yl)-4-(trifluoromethyl)pyrimidin-2-amine | 456 | 456 | Free Base |
| 1.19 | | N-[5-(4-ethylpiperazin-1-yl)biphenyl-3-yl]-4-(trifluoromethyl)pyrimidin-2-amine | 428 | 428 | Free Base |
| 1.20 | racemic | N-{5-[(2-oxa-5-azabicyclo[2.2.1]hept-5-yl)biphenyl-3-yl]-4-(trifluoromethyl)pyrimidin-2-amine | 413 | 413 | Free Base |
| 1.21 | racemic | [4-(5-{[4-(trifluoromethyl)pyrimidin-2-yl]amino}biphenyl-3-yl)morpholin-2-yl]methyl acetate | 473 | 473 | Free Base |
| 1.22 | | N-[5-(1,4-oxazepan-4-yl)biphenyl-3-yl]-4-(trifluoromethyl)pyrimidin-2-amine | 415 | 415 | Free Base |

TABLE 1.2-continued

| Ex. No. | R⁴ | Name | [M + H]+ Calc'd | [M + H]+ Obsv'd | Form(s) |
|---|---|---|---|---|---|
| 1.23 | tetrahydro-2H-pyran-4-yloxy | N-[5-(tetrahydro-2H-pyran-4-yloxy)biphenyl-3-yl]-4-(trifluoromethyl)pyrimidin-2-amine | 416 | 416 | Free Base |
| 1.24 | piperidin-4-yloxy | N-[5-(piperidin-4-yloxy)biphenyl-3-yl]-4-(trifluoromethyl)pyrimidin-2-amine | 415 | 415 | Free Base |

TABLE 1.3

| Ex. No. | R¹ | R³ | R⁴ | Name | [M + H]+ Calc'd | [M + H]+ Obsv'd | Form(s) |
|---|---|---|---|---|---|---|---|
| 1.25 | —CF₃ | morpholin-4-yl | —H | N-(6-morpholin-4-ylbiphenyl-3-yl)-4-(trifluoromethyl)pyrimidin-2-amine | 401 | 401 | Free Base |
| 1.26 | piperidin-4-yloxy | morpholin-4-yl | —H | N-[6-(morpholin-4-yl)biphenyl-3-yl]-4-(piperidin-4-yloxy)pyrimidin-2-amine | 432 | 432 | Free Base |

TABLE 1.3-continued

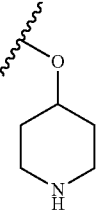

| Ex. No. | R¹ | R³ | R⁴ | Name | [M + H]+ Calc'd | [M + H]+ Obsv'd | Form(s) |
|---|---|---|---|---|---|---|---|
| 1.27 | 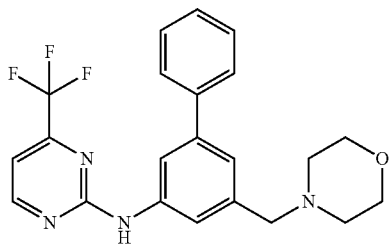 | —H | 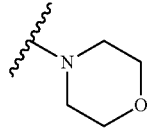 [SMILES: *N1CCOCC1] | N-[5-(morpholin-4-yl)biphenyl-3-yl]-4-(piperidin-4-yloxy)pyrimidin-2-amine | 432 | 432 | Free Base |

Example 1.28

N-[5-(Morpholin-4-ylmethyl)biphenyl-3-yl]-4-(trifluoromethyl)pyrimidin-2-amine 1.28

Step 1:
A suspension of 1-bromo-3-methyl-5-nitrobenzene (1.00 g, 4.63 mmol), phenylboronic acid (0.847 g, 6.94 mmol), sodium carbonate (0.981 g, 9.26 mmol), palladium(II) acetate (0.052 g, 0.231 mmol) and tri-o-tolylphosphine (0.141 g, 0.463 mmol) in DME (2 mL) and water (8 mL) was heated to 110° C. for 30 minutes in the microwave reactor. Upon coolingl to room temperature, the reaction mixture was diluted with ethyl acetate and filtered through CELITE. The solution was concentrated in vacuo, and the resulting residue was purified by silica gel column chromatography (ethyl acetate/hexanes) to provide 3-methyl-5-nitrobiphenyl as a yellow solid.

Step 2:
NBS (184 mg, 1.032 mmol) and AIBN (15.4 mg, 0.04 mmol) were added to a solution of 3-methyl-5-nitrobiphenyl (200 mg, 0.938 mmol) in carbon tetrachloride (1.88 mL) and then the reaction mixture was heated to 80° C. for 3 hours. Additional AIBN (15.4 mg, 0.04 mmol) was added to the reaction mixture and was heated for additional 1 hour. The mixture was purified directly by silica gel column chromatography (ethyl acetate/hexanes) to yield 3-(bromomethyl)-5-nitrobiphenyl.

Step 3:
Morpholine (0.204 mL, 2.345 mmol) was added to a solution of benzylbromide (137 mg, 0.47 mmol) in THF (4.69 mL) and then the reaction mixture was stirred for 14 hours at room temperature. The reaction mixture was diluted with ethyl acetate (30 mL) and washed with saturated aqueous NaHCO$_3$(aq) (30 mL) followed by brine (30 mL). The aqueous layers were further extracted with ethyl acetate (30 mL), then the combined organic extracts were dried over sodium sulfate, filtered, and concentrated in vacuo. The residue was purified by silica gel column chromatography (ethyl acetate/hexanes) provided 4-[(5-nitrobiphenyl-3-yl)methyl]morpholine as a colorless oil. $^1$H NMR (400 MHz, CDCl$_3$) δ 8.34 (s, 1H), 8.20 (s, 1H), 7.92 (s, 1H), 7.65 (s, 1H), 7.63 (s, 1H), 7.51 (t, J=7.5 Hz, 2H), 7.44 (t, J=7.2 Hz, 1H), 3.85-3.71 (m, 4H), 3.65 (s, 2H), 2.65-2.37 (m, 4H).

Step 4:
Palladium on carbon (10 wt %, 47.8 mg, 0.045 mmol) was added to a solution of 4-[(5-nitrobiphenyl-3-yl)methyl]morpholine in ethyl acetate (4.1 mL) and acetic acid (0.408 mL). The reaction mixture was fitted with a hydrogen balloon and stirred at room temperature for 3 hours. Dichloromethane was added to the reaction mixture, and then filtered through CELITE and washed with dichloromethane. The organic fractions were washed with saturated aqueous NaHCO$_3$, dried over sodium sulfate, filtered, and concentrated in vacuo to afford 5-(morpholin-4-ylmethyl)biphenyl-3-amine which was used without further purification. $^1$H NMR (400 MHz, CDCl$_3$) δ 7.58 (t, J=5.9 Hz, 2H), 7.43 (dd, J=9.5, 5.6 Hz, 2H), 7.35 (t, J=7.3 Hz, 1H), 6.97 (s, 1H), 6.83 (s, 1H), 6.71 (s, 1H), 3.92-3.61 (m, 4H), 3.49 (s, 2H), 2.50 (s, 4H).

Step 5:
p-Toluenesulfonic acid monohydrate (75 mg, 0.395 mmol) was added to a solution of 2-chloro-4-(trifluoromethyl)pyrimidine (36 mg, 0.198 mmol) and 5-(morpholin-4-ylmethyl)biphenyl-3-amine (53 mg, 0.198 mmol) in dioxane (1.98 mL) and heated to 80° C. for 14 hours, then allowed to cool to room temperature. The mixture was diluted with ethyl acetate (30 mL) and washed with saturate aqueous NaHCO$_3$ (30 mL) and 1:1 water: brine (2×30 mL). The organic extracts were dried over sodium sulfate, filtered, and concentrated in vacuo. The residue was purified by silica gel column chromatography (thyl acetate/hexanes) provided N-[5-(morpholin-4-ylmethyl)biphenyl-3-yl]-4-(trifluoromethyl)pyrimidin-2-amine. MS ESI calc'd. for $C_{22}H_{22}F_3N_4O$ [M+H]+ 415, found 415. $^1$H NMR (400 MHz, CDCl$_3$): δ 8.67 (d, J=4.9 Hz, 1H); 7.90 (s, 1H); 7.66 (d, J=7.7 Hz, 2H); 7.58 (s, 1H); 7.51-7.42 (m, 3H); 7.39 (t, J=7.4 Hz, 1H); 7.33 (s, 1H); 7.06 (d, J=4.9 Hz, 1H); 3.76 (t, J=4.5 Hz, 4H); 3.61 (s, 2H); 2.54 (t, J=4.2 Hz, 4H).

Example 1.29

Morpholin-4-yl(5-{[4-(trifluoromethyl)pyrimidin-2-yl]amino}biphenyl-3-yl)methanone

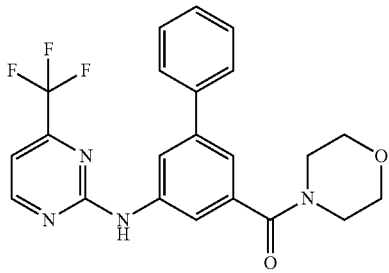

1.29

Step 1:
HATU (927 mg, 2.44 mmol), morpholine (0.212 mL, 2.44 mmol), and diisopropylethylamine (0.532 mL, 3.05 mmol) were added sequentially to a solution of 3-bromo-5-nitrobenzoic acid (500 mg, 2.03 mmol) in DMF (10 mL) at 0° C. The reaction mixture was stirred for 2 hours at 0° C., then the mixture was diluted with ethyl acetate (50 mL) and washed with saturated aqueous NaHCO$_3$ (50 mL) followed by 1:1 water: brine (2×30 mL). The organic layers were dried over sodium sulfate, filtered, and concentrated in vacuo. The residue was purified by silica gel column chromatography (ethyl acetate/hexanes) provided (3-bromo-5-nitrophenyl)(morpholin-4-yl)methanone as a white solid. $^1$H NMR (400 MHz, CDCl$_3$) δ 8.43 (t, J=1.9 Hz, 1H), 8.28-8.12 (m, 1H), 7.89 (t, J=1.5 Hz, 1H), 3.74 (br m, 8H).

Step 2:
A suspension of (3-bromo-5-nitrophenyl)(morpholin-4-yl)methanone (200 mg, 0.635 mmol), phenylboronic acid (101 mg, 0.825 mmol), sodium carbonate (101 mg, 0.952 mmol), tri-o-tolylphosphine (19.32 mg, 0.063 mmol) and palladium(II) acetate in DME (1.02 mL) and water (0.25 mL) was heated to 100° C. for 3 hours, then allowed to cool to room temperature. The mixture was diluted with ethyl acetate (50 mL), filtered through CELITE, and washed with brine (30 mL). The organic extracts were dried over sodium sulfate, filtered, and concentrated in vacuo. The residue was purified by silica gel column chromatography (ethyl acetate:hexanes) provided morpholin-4-yl(5-nitrobiphenyl-3-yl)methanone as a colorless, viscous oil. $^1$H NMR (400 MHz, CDCl$_3$) δ 8.53 (t, J=1.6 Hz, 1H), 8.25 (s, 1H), 7.98 (s, 1H), 7.65 (d, J=7.3 Hz, 2H), 7.61-7.43 (m, 3H), 3.69 (dd, J=65.5, 62.1 Hz, 8H).

Step 3:
Palladium on carbon (10 wt %, 67.5 mg, 0.063 mmol) was added to a solution of morpholin-4-yl(5-nitrobiphenyl-3-yl)methanone (198 mg, 0.634 mmol) in ethyl acetate (5.7 mL) and acetic acid (0.57 mL). The mixture was fitted with a hydrogen balloon and stirred for 3 hours at room temperature. Dichloromethane was added, and the mixture was filtered through CELITE, rinsed with dichloromethane rinse and washed with saturated aqueous NaHCO$_3$ (30 mL). The organic extracts were dried over sodium sulfate, filtered, and concentrated in vacuo to provide (5-aminobiphenyl-3-yl)(morpholin-4-yl)methanone as a white solid which was used without further purification. $^1$H NMR (400 MHz, CDCl$_3$) δ 7.61-7.51 (m, 2H), 7.44 (t, J=7.4 Hz, 2H), 7.37 (dd, J=8.4, 6.2 Hz, 1H), 6.97 (s, 1H), 6.96-6.91 (m, 1H), 6.75-6.63 (m, 1H), 3.89 (s, 2H), 3.85-3.37 (m, 8H).

Step 4:
A solution of 2-chloro-4-(trifluoromethyl)pyrimidine (34 mg, 0.186 mmol), (5-aminobiphenyl-3-yl)(morpholin-4-yl)methanone (63.1 mg, 0.224 mmol), sodium tert-butoxide, Pd$_2$(dba)$_3$ (9.64 mg, 0.009 mmol) and BINAP (11.6 mg, 0.019 mmol) in toluene (0.931 mL) was heated to 130° C. in a microwave reactor for 30 minutes, then allowed to cool to room temperature. The reaction mixture was diluted with ethyl acetate (30 mL) and was washed with 0.1 M HCl (30 mL) followed by brine (30 mL). The aqueous phases were further extracted with ethyl acetate (30 mL), then the combined organic extracts were dried over sodium sulfate, filtered, and concentrated in vacuo. The residue was purified by silica gel column chromatography (ethyl acetate/hexanes) provided morpholin-4-yl(5-{[4-(trifluoromethyl)pyrimidin-2-yl]amino}biphenyl-3-yl)methanone as a white solid. MS ESI calc'd. for $C_{22}H_{20}F_3N_4O_2$ [M+H]+ 429, found 429. $^1$H NMR (400 MHz, CDCl$_3$): δ 8.69 (d, J=4.9 Hz, 1H); 7.92 (s, 1H); 7.80 (s, 1H); 7.71 (s, 1H); 7.63 (d, J=7.6 Hz, 2H); 7.48 (t, J=7.5 Hz, 2H); 7.40 (d, J=6.8 Hz, 2H); 7.15-7.03 (m, 1H); 3.97-3.44 (m, 8H).

Example 1.30

N-{5-[4-(methylsulfonyl)piperazin-1-yl]biphenyl-3-yl}-4-(trifluoromethyl)pyrimidin-2-amine

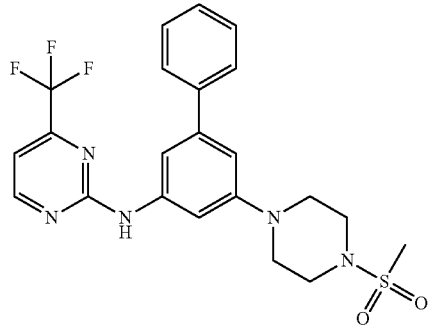

1.30

Step 1:
1-(methylsulfonyl)piperazine (627 mg, 3.82 mmol) was added to a solution of 1-fluoro-3-iodo-5-nitrobenzene (510 mg, 1.91 mmol) in dimethylsulfoxide (2 mL). The reaction was heated to 130° C. for 60 minutes in the microwave reaction, then allowed to cool to room temperature. The reaction mixture was diluted with ethyl acetate (30 mL) and washed with 1:1 water:brine (3×30 mL). The organic extracts were dried over sodium sulfate, filtered, and concentrated in vacuo. The residue was purified by silica gel column chromatography (ethyl acetate/hexanes) provided 1-(3-iodo-5-nitrophenyl)-4-(methylsulfonyl)piperazine as a bright yellow foam. $^1$H NMR (400 MHz, CDCl$_3$) δ 8.04 (s, 1H), 7.70 (s, 1H), 7.51 (s, 1H), 3.42 (s, 8H), 2.87 (s, 3H).

Step 2:

A suspension of 1-(3-iodo-5-nitrophenyl)-4-(methylsulfonyl)piperazine (50 mg, 0.122 mmol), phenylboronic acid (29.7 mg, 0.243 mmol), tri-o-tolylphosphine (3.7 mg, 0.012 mmol), Pd(OAc)$_2$ (1.37 mg, 0.006 mmol) and sodium carbonate (26 mg, 0.24 mmol) in 4:1 DME/water (5.13 mL) was heated to 100° C. in a sealed tube for 2 hours. The mixture was diluted ethyl acetate (20 mL), dried over sodium sulfate, and the mixture was filtered through CELITE. After concentration in vacuo, the residue was purified by silica gel column chromatography (ethyl acetate/hexanes) to provide 1-(5-{3-[4-(methylsulfonyl)piperazin-1-yl]-5-nitrophenyl}thiophen-2-yl)ethanone. $^1$H NMR (400 MHz, CDCl$_3$) δ 7.97 (t, J=1.6 Hz, 1H), 7.74 (t, J=2.1 Hz, 1H), 7.66-7.57 (m, 2H), 7.58-7.42 (m, 3H), 7.41 (dd, J=7.6, 6.1 Hz, 1H), 3.46 (s, 8H), 2.88 (s, 3H).

Step 3:

Palladium on carbon (10 wt %, 13 mg, 0.012 mmol) was added to a solution of 1-(methylsulfonyl)-4-(5-nitrobiphenyl-3-yl)piperazine (44.1 mg, 0.122 mmol) in ethyl acetate (1 mL) and acetic acid (0.1 mL) and the reaction mixture was stirred under an atmosphere of H$_2$ (balloon) for 90 minutes. Dichloromethane was added to the reaction mixture, and the mixture was filtered through CELITE, rinsed with ethyl acetate and concentrated in vacuo. The residue was purified by silica gel column chromatography (ethyl acetate/hexanes) to provide 5-[4-(methylsulfonyl)piperazin-1-yl]biphenyl-3-amine as a white foam. $^1$H NMR (400 MHz, Acetone) δ 9.18 (s, 1H), 8.82 (d, J=4.9 Hz, 1H), 7.77-7.63 (m, 3H), 7.47 (dd, J=10.4, 4.7 Hz, 2H), 7.37 (t, J=7.4 Hz, 1H), 7.23 (d, J=4.9 Hz, 1H), 7.02 (d, J=1.5 Hz, 1H), 3.43 (dd, J=12.4, 5.3 Hz, 8H), 2.91 (s, 3H).

Step 4:

p-Toluenesulfonic acid (21.46 mg, 0.113 mmol) and 2-chloro-4-(trifluoromethyl)pyrimidine (22.5 mg, 0.123 mmol) were added to a solution of 5-[4-(methylsulfonyl)piperazin-1-yl]biphenyl-3-amine (34 mg, 0.103 mmol) in dioxane (1 mL) and the reaction mixture was stirred for 14 hours at 100° C., then allowed to cool to room temperature. The reaction mixture was diluted with ethyl acetate (30 mL), then washed with saturated aqueous NaHCO$_3$ (30 mL) followed by brine (30 mL). The aqueous layers were extracted with ethyl acetate (30 mL), then the combined organic layers were dried over sodium sulfate, filtered, and concentrated in vacuo. The residue was purified by silica gel column chromatography (ethyl acetate/hexanes) provided N-{5-[4-(methylsulfonyl)piperazin-1-yl]biphenyl-3-yl}-4-(trifluoromethyl)pyrimidin-2-amine MS ESI calc'd. for C$_{22}$H$_{23}$F$_3$N$_5$O$_2$S [M+H]$^+$ 478, found 478. $^1$H NMR (400 MHz, Acetone): δ 9.18 (s, 1H); 8.82 (d, J=4.9 Hz, 1H); 7.71-7.66 (m, 4H); 7.47 (t, J=7.5 Hz, 2H); 7.37 (t, J=7.3 Hz, 1H); 7.23 (d, J=4.9 Hz, 1H); 7.02 (s, 1H); 3.43 (d, J=10.6 Hz, 8H); 2.91 (s, 3H).

The following examples in Tables 1.4 and 1.5 were prepared in an analogous manner to that described for Example 1.30.

TABLE 1.4

| Ex. No. | R$^4$ | R$^{cy}$ | Name | [M + H]+ Calc'd | [M + H]+ Obsv'd | Form(s) |
|---|---|---|---|---|---|---|
| 1.31 | —N(CH$_3$)$_2$ | F, F, OH (difluoroethanol group) | (1S)-1-[3'-(dimethylamino)-5'-{[4-(trifluoromethyl)pyrimidin-2-yl]amino}biphenyl-4-yl]-2,2-difluoroethanol | 439 | 439 | Free Base |
| 1.32 | morpholin-4-yl | F, F, OH (difluoroethanol group) | (1R)-2,2-difluoro-1-(3'-morpholin-4-yl-5'-{[4-(trifluoromethyl)pyrimidin-2-yl]amino}biphenyl-4-yl)ethanol | 481 | 481 | Free Base |
| 1.33 | morpholin-4-yl | tetrahydro-2H-pyran-4-ol | 4-(3'-morpholin-4-yl-5'-{[4-(trifluoromethyl)pyrimidin-2-yl]amino}biphenyl-4-yl)tetrahydro-2H-pyran-4-ol | 501 | 501 | Free Base |

TABLE 1.5

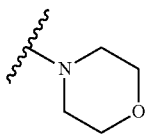 [SMILES: *N1CCOCC1]

| Ex. No. | R⁴ | R^cy | Name | [M + H]+ Calcd | [M + H]+ Obsvd | Form(s) |
|---|---|---|---|---|---|---|
| 1.34 | 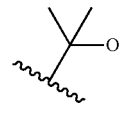 | 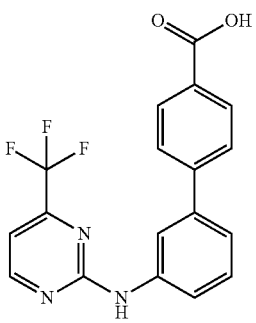 | 2-(3'-morpholin-4-yl-5'-{[4-(trifluoromethyl)pyrimidin-2-yl]amino}biphenyl-3-yl)propan-2-ol | 459 | 459 | Free Base |

Example 1.35

3'-{[4-(Trifluoromethyl)pyrimidin-2-yl]amino}biphenyl-4-carboxylic acid 1.35

Step 1:

Ethyl 4-bromobenzoate (73.2 mg, 0.301 mmol) was added to a mixture of N-[3-(4,4,5,5-tetramethyl-1,3,2-dioxaborolan-2-yl)phenyl]-4-(trifluoromethyl)pyrimidin-2-amine (100 mg, 0.274 mmol), PdCl₂(dppf)-CH₂Cl₂ adduct (22.4 mg, 0.027 mmol), DMF (5.5 mL), and aqueous K₂CO₃ (2 M, 0.411 mL, 0.822 mmol) and the reaction mixture was evacuated and back flushed with Argon. The reaction mixture was heated in the microwave reactor for 2 hours at 85° C. The reaction mixture was diluted with water, extracted with ethyl acetate, washed with brine, dried over sodium sulfate, filtered, and concentrated in vacuo. The residue was purified by silica gel column chromatography (ethyl acetate/hexanes) to afford ethyl 3'-{[4-(trifluoromethyl)pyrimidin-2-yl]amino}biphenyl-4-carboxylate as an off-white solid. MS ESI calc'd. for $C_{20}H_{17}F_3N_3O_2[M+H]^+$ 388, found 388. $^1$H NMR (500 MHz, CDCl₃): δ 8.67 (d, J=4.9 Hz, 1H); 7.96 (s, 1H); 7.61 (t, J=6.2 Hz, 3H); 7.55 (s, 1H); 7.47-7.40 (m, 1H); 7.40 (d, J=7.9 Hz, 2H); 7.35 (d, J=7.7 Hz, 1H); 7.06 (d, J=4.9 Hz, 1H); 4.22 (q, J=7.1 Hz, 2H); 1.31 (t, J=7.1 Hz, 3H).

Step 2:

Lithium hydroxide (2 M, 0.374 mL, 0.749 mmol) was added to a solution of ethyl 3'-{[4-(trifluoromethyl)pyrimidin-2-yl]amino}biphenyl-4-carboxylate in THF (1.99 mL) and methanol (0.99 mL) at room temperature, and then the mixture was heated at 45° C. for 6 hours. The reaction mixture was cooled to room temperature, neutralized with 10% aqueous HCl, diluted with brine, extracted with ethyl acetate (2×), dried over sodium sulfate, filtered and concentrated in vacuo. The residue was purified by silica gel column chromatography (ethyl acetate/hexanes+0.1% AcOH) to afford 3'-{[4-(trifluoromethyl)pyrimidin-2-yl]amino}biphenyl-4-carboxylic acid as an off-white solid MS ESI calc'd. for $C_{18}H_{13}F_3N_3O_2$ [M+H]⁺ 360, found 360. $^1$H NMR (500 MHz, CD₃OD): δ 8.74 (s, 1H); 8.17 (s, 1H); 8.12 (d, J=7.9 Hz, 2H); 7.81-7.73 (m, 3H); 7.45 (t, J=7.9 Hz, 1H); 7.42-7.36 (m, 1H); 7.15 (d, J=4.5 Hz, 1H).

The following examples in Tables 1.6-1.9 were prepared in an analogous manner to that described for Example 1.35. In some cases, step 2 was omitted. **APCI [M–H]⁻ m/z observed.

TABLE 1.6

| Ex. No. | R^cy | Name | [M + H]+ Calc'd | [M + H]+ Obsv'd | Form(s) |
|---|---|---|---|---|---|
| 1.36 | CF3-CH(NH2)- (racemic) | N-[4'-(1-amino-2,2,2-trifluoroethyl)biphenyl-3-yl]-4-(trifluoromethyl)pyrimidin-2-amine | 413 | 413 | Free Base |
| 1.37 | (CF3)2C(OH)- | 1,1,1,3,3,3-hexafluoro-2-(3'-{[4-(trifluoromethyl)pyrimidin-2-yl]amino}biphenyl-4-yl)propan-2-ol | 482 | 482 | Free Base |
| 1.38 | CHF2-CH(OH)- (1R) | (1R)-2,2-difluoro-1-(3'-{[4-(trifluoromethyl)pyrimidin-2-yl]amino}biphenyl-4-yl)ethanol | 396 | 396 | Free Base |
| 1.39 | 1-hydroxycyclopropyl | 1-(3'-{[4-(trifluoromethyl)pyrimidin-2-yl]amino}biphenyl-4-yl)cyclopropanol | 372 | 372 | Free Base |
| 1.40 | —Br | N-(4'-bromobiphenyl-3-yl)-4-(trifluoromethyl)pyrimidin-2-amine | 394 | 394 | Free Base |
| 1.41 | —CN | 3'-{[4-(trifluoromethyl)pyrimidin-2-yl]amino}biphenyl-4-carbonitrile | 341 | 341 | Free Base |
| 1.42 | —OCH3 | N-(4'-(methoxybiphenyl-3-yl)-4-(trifluoromethyl)pyrimidin-2-amine | 346 | 346 | Free Base |
| 1.43 | —SCH3 | N-[4'-(methylsulfanyl)biphenyl-3-yl]-4-(trifluoromethyl)pyrimidin-2-amine | 362 | 362 | Free Base |
| 1.44 | —C(O)CH3 | 1-(3'-{[4-(trifluoromethyl)pyrimidin-2-yl]amino}biphenyl-4-yl)ethanone | 358 | 358 | Free Base |
| 1.45 | —C(CH3)2OH | 2-(3'-{[4-(trifluoromethyl)pyrimidin-2-yl]amino}biphenyl-4-yl)propan-2-ol | 374 | 374 | Free Base |
| 1.46 | —NH2 | N~3~-[4-(trifluoromethyl)pyrimidin-2-yl]biphenyl-3,4'-diamine | 331 | 331 | Free Base |
| 1.47 | —NHC(O)CH3 | N-(3'-{[4-(trifluoromethyl)pyrimidin-2-yl]amino}biphenyl-4-yl)acetamide | 373 | 373 | Free Base |

TABLE 1.6-continued

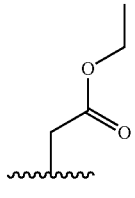

| Ex. No. | R<sup>cy</sup> | Name | [M + H]+ Calc'd | [M + H]+ Obsv'd | Form(s) |
|---|---|---|---|---|---|
| 1.48 | —S(O)₂CH₃ | N-[4'-(methylsulfonyl)biphenyl-3-yl]-4-(trifluoromethyl)pyrimidin-2-amine | 394 | 392** | Free Base |
| 1.49 | —S(O)₂NH₂ | 3'-{[4-(trifluoromethyl)pyrimidin-2-yl]amino}biphenyl-4-sulfonamide | 395 | 395 | Free Base |
| 1.50 | —OH | 3'-{[4-(trifluoromethyl)pyrimidin-2-yl]amino}biphenyl-4-ol | 332 | 332 | Free Base |
| 1.51 | 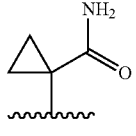 | ethyl (3'-{[4-(trifluoromethyl)pyrimidin-2-yl]amino}biphenyl-4-yl)acetate | 402 | 402 | Free Base |
| 1.52 | —C(O)NH₂ | 3'-{[4-(trifluoromethyl)pyrimidin-2-yl]amino}biphenyl-4-carboxamide | 359 | 359 | Free Base |
| 1.53 | 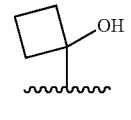 | 1-(3'-{[4-(trifluoromethyl)pyrimidin-2-yl]amino}biphenyl-4-yl)cyclopropanecarboxamide | 399 | 399 | Free Base |
| 1.54 | 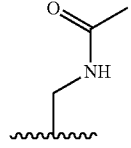 [SMILES: *CNC(C)=O] | 1-(3'-{[4-(trifluoromethyl)pyrimidin-2-yl]amino}biphenyl-4-yl)cyclobutanol | 386 | 386 | Free Base |
| 1.55 | 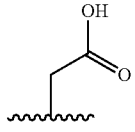 [SMILES: *CC(=O)O] | N-[(3'-{[4-(trifluoromethyl)pyrimidin-2-yl]amino}biphenyl-4-yl)methyl]acetamide | 387 | 387 | Free Base |
| 1.56 |  | (3'-{[4-(trifluoromethyl)pyrimidin-2-yl]amino}biphenyl-4-yl)acetic acid | 374 | 374 | Free Base |

TABLE 1.7

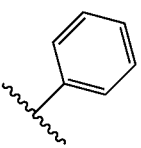 [SMILES: *c1ccccc1]

| Ex. No. | R<sup>cy</sup> | Name | [M + H]+ Calc'd | [M + H]+ Obsv'd | Form(s) |
|---|---|---|---|---|---|
| 1.57 | —C(O)OCH$_2$CH$_3$ | ethyl 3'-{[4-(trifluoromethyl)pyrimidin-2-yl]amino}biphenyl-3-carboxylate | 388 | 388 | Free Base |
| 1.58 | —S—CH$_3$ | N-[3'-(methylsulfanyl)biphenyl-3-yl]-4-(trifluoromethyl)pyrimidin-2-amine | 362 | 362 | Free Base |
| 1.59 | —Br | N-(3'-bromobiphenyl-3-yl)-4-(trifluoromethyl)pyrimidin-2-amine | 394 | 394 | Free Base |
| 1.60 | —CN | 3'-{[4-(trifluoromethyl)pyrimidin-2-yl]amino}biphenyl-3-carbonitrile | 341 | 341 | Free Base |
| 1.61 | 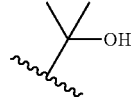 [SMILES: *C(C)(C)O] | N-1,1':3',1''-terphenyl-3-yl-4-(trifluoromethyl)pyrimidin-2-amine | 392 | 392 | Free Base |
| 1.62 | —OCH$_3$ | N-(3'-methoxybiphenyl-3-yl)-4-(trifluoromethyl)pyrimidin-2-amine | 346 | 346 | Free Base |
| 1.63 | —C(O)CH$_3$ | 1-(3'-{[4-(trifluoromethyl)pyrimidin-2-yl]amino}biphenyl-3-yl)ethanone | 358 | 358 | Free Base |
| 1.64 | 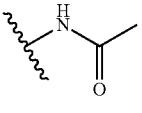 | 2-(3'-{[4-(trifluoromethyl)pyrimidin-2-yl]amino}biphenyl-3-yl)propan-2-ol | 374 | 374 | Free Base |
| 1.65 | —NH$_2$ | N-[4-(trifluoromethyl)pyrimidin-2-yl]biphenyl-3,3'-diamine | 331 | 331 | Free Base |
| 1.66 | 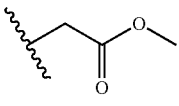 [SMILES: *CC(=O)OC] | N-(3'-{[4-(trifluoromethyl)pyrimidin-2-yl]amino}biphenyl-3-yl)acetamide | 373 | 373 | Free Base |
| 1.67 | —S(O)$_2$CH$_3$ | N-[3'-(methylsulfonyl)biphenyl-3-yl]-4-(trifluoromethyl)pyrimidin-2-amine | 394 | 394 | Free Base |
| 1.68 | —S(O)$_2$NH$_2$ | 3'-{[4-(trifluoromethyl)pyrimidin-2-yl]amino}biphenyl-3-sulfonamide | 395 | 395 | Free Base |
| 1.69 | —OH | 3'-{[4-(trifluoromethyl)pyrimidin-2-yl]amino} biphenyl-3-ol | 332 | 332 | Free Base |
| 1.70 | 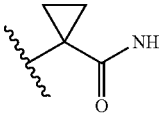 | methyl (3'-{[4-(trifluoromethyl)pyrimidin-2-yl]amino}biphenyl-3-yl)acetate | 388 | 388 | Free Base |
| 1.71 | —C(O)NH$_2$ | 3'-{[4-(trifluoromethyl)pyrimidin-2-yl]amino}biphenyl-3-carboxamide | 359 | 359 | Free Base |
| 1.72 |  | 1-(3'-{[4-(trifluoromethyl)pyrimidin-2-yl]amino}biphenyl-3-yl)cyclopropanecarboxamide | 399 | 399 | Free Base |

TABLE 1.7-continued

[Structure: 4-(trifluoromethyl)pyrimidin-2-yl amino linked to biphenyl with R^cy at 3' position]

| Ex. No. | R^cy | Name | [M + H]+ Calc'd | [M + H]+ Obsv'd | Form(s) |
|---|---|---|---|---|---|
| 1.73 | cyclobutanol-OH | 1-(3'-{[4-(trifluoromethyl)pyrimidin-2-yl]amino}biphenyl-3-yl)cyclobutanol | 386 | 386 | Free Base |
| 1.74 | -CH₂NHC(O)CH₃ | N-[(3'-{[4-(trifluoromethyl)pyrimidin-2-yl]amino}biphenyl-3-yl)methyl]acetamide | 387 | 387 | Free Base |
| 1.75 | —CO₂H | 3'-{[4-(trifluoromethyl)pyrimidin-2-yl]amino}biphenyl-3-carboxylic acid | 360 | 360 | Free Base |
| 1.76 | -CH₂CO₂H | (3'-{[4-(trifluoromethyl)pyrimidin-2-yl]amino}biphenyl-3-yl)acetic acid | 374 | 374 | Free Base |
| 1.77 | -CH₂NH₂ | N-[3'-(aminomethyl)biphenyl-3-yl]-4-(trifluoromethyl)pyrimidin-2-amine | 345 | 343** | Free Base |

TABLE 1.8

[Structure: 4-(trifluoromethyl)pyrimidin-2-yl amino linked to phenyl with R^4 and C^y substituents]

| Ex. No. | R^4 | C^y | Name | [M + H]+ Calc'd | [M + H]+ Obsv'd | Form(s) |
|---|---|---|---|---|---|---|
| 1.78 | —CH₃ | 3-carboxyphenyl | 3'-methyl-5'-{[4-(trifluoromethyl)pyrimidin-2-yl]amino}biphenyl-3-carboxylic acid | 374 | 374 | Free Base |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.79 | —CH₃ | | N-[(3'-methyl-5'-{[4-(trifluoromethyl)pyrimidin-2-yl]amino}biphenyl-3-yl)carbonyl]glycine | 431 | 431 | Free Base |
| 1.80 | —CH₃ | racemic | trans-4-[1-hydroxy-1-(3'-methyl-5'-{[4-(trifluoromethyl)pyrimidin-2-yl]amino}biphenyl-4-yl)ethyl]cyclohexanecarboxylic acid | 500 | 500 | TFA Salt |
| 1.81 | —H | | ethyl 3-(3'-{[4-(trifluoromethyl)pyrimidin-2-yl]amino}biphenyl-3-yl)propanoate | 416 | 416 | Formate Salt |
| 1.82 | —H | | 3-(3'-{[4-(trifluoromethyl)pyrimidin-2-yl]amino}biphenyl-4-yl)propanoic acid | 388 | 388 | Formate Salt |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.83 | —CH₃ | (3-carboxyethyl-phenyl) | 3-(3'-methyl-5'-{[4-(trifluoromethyl)pyrimidin-2-yl]amino}biphenyl-3-yl)propanoic acid | 402 | 402 | Formate Salt, Ammonium Salt |
| 1.84 | —CH₃ | (4-carboxyethyl-phenyl) | 3-(3'-methyl-5'-{[4-(trifluoromethyl)pyrimidin-2-yl]amino}biphenyl-4-yl)propanoic acid | 402 | 402 | Formate Salt, Ammonium Salt |
| 1.85 | —H | (3-carboxyethyl-phenyl) | 3-(3'-{[4-(trifluoromethyl)pyrimidin-2-yl]amino}biphenyl-3-yl)propanoic acid | 388 | 388 | Ammonium Salt |
| 1.86 | —CH₃ | (3-cyanophenyl) | 3'-methyl-5'-{[4-(trifluoromethyl)pyrimidin-2-yl]amino}biphenyl-3-carbonitrile | 355 | 355 | Free Base |
| 1.87 | —CH₃ | (3-methoxycarbonyl-phenyl) | methyl 3'-methyl-5'-{[4-(trifluoromethyl)pyrimidin-2-yl]amino}biphenyl-3-carboxylate | 388 | 388 | Free Base |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.88 | —CH₃ | | 3''-methyl-5''-{[4-(trifluoromethyl)pyrimidin-2-yl]amino}-1,1':4',1''-terphenyl-2'-carboxylic acid | 450 | 450 | Formate Salt |
| 1.89 | —CH₃ | | 2-(difluoromethoxy)-3'-methyl-5'-{[4-(trifluoromethyl)pyrimidin-2-yl]amino}biphenyl-3-carboxylic acid | 440 | 440 | Formate Salt |
| 1.90 | —CH₃ | | 6-(difluoromethyl)-3'-methyl-5'-{[4-(trifluoromethyl)pyrimidin-2-yl]amino}biphenyl-3-carboxylic acid | 424 | 424 | Formate Salt |
| 1.91 | —CH₃ | | 3'-methyl-2-propyl-5'-{[4-(trifluoromethyl)pyrimidin-2-yl]amino}biphenyl-3-carboxylic acid | 416 | 416 | Formate Salt |
| 1.92 | —CH₃ | | 2-ethyl-3'-methyl-5'-{[4-(trifluoromethyl)pyrimidin-2-yl]amino}biphenyl-3-carboxylic acid | 402 | 402 | Formate Salt |
| 1.93 | —CH₃ | | 6-cyano-3'-methyl-5'-{[4-(trifluoromethyl)pyrimidin-2-yl]amino}biphenyl-3-carboxylic acid | 399 | 399 | Formate Salt |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.94 | —CH₃ | (3-carboxy-6-difluoromethoxyphenyl with OH and OCHF₂) | 6-(difluoromethoxy)-3'-methyl-5'-{[4-(trifluoromethyl)pyrimidin-2-yl]amino}biphenyl-3-carboxylic acid | 440 | 440 | Formate Salt |
| 1.95 | —CH₃ | (3-carboxy-6-trifluoromethoxyphenyl with OH and OCF₃) | 3'-methyl-6-(trifluoromethoxy)-5'-{[4-(trifluoromethyl)pyrimidin-2-yl]amino}biphenyl-3-carboxylic acid | 458 | 458 | Formate Salt |
| 1.96 | —CH₃ | (5-cyano-3-carboxyphenyl) | 5-cyano-3'-methyl-5'-{[4-(trifluoromethyl)pyrimidin-2-yl]amino}biphenyl-3-carboxylic acid | 399 | 399 | Formate Salt |
| 1.97 | —CH₃ | (2-methyl-3-carboxyphenyl) | 2,3'-dimethyl-5'-{[4-(trifluoromethyl)pyrimidin-2-yl]amino}biphenyl-3-carboxylic acid | 388 | 388 | Formate Salt |
| 1.98 | —CH₃ | (5-fluoro-3-carboxyphenyl) | 5-fluoro-3'-methyl-5'-{[4-(trifluoromethyl)pyrimidin-2-yl]amino}biphenyl-3-carboxylic acid | 392 | 392 | Formate Salt |
| 1.99 | —CH₃ | (4-amino-3-carboxyphenyl) | 4-amino-3'-methyl-5'-{[4-(trifluoromethyl)pyrimidin-2-yl]amino}biphenyl-3-carboxylic acid | 389 | 389 | Formate Salt |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.100 | —CH₃ | 2-hydroxy-5-substituted benzoic acid | 4-hydroxy-3'-methyl-5'-{[4-(trifluoromethyl)pyrimidin-2-yl]amino}biphenyl-3-carboxylic acid | 390 | 390 | Formate Salt |
| 1.101 | —CH₃ | 3-amino-5-substituted benzoic acid | 5-amino-3'-methyl-5'-{[4-(trifluoromethyl)pyrimidin-2-yl]amino}biphenyl-3-carboxylic acid | 389 | 389 | Formate Salt |
| 1.102 | —CH₃ | 2-chloro-5-substituted benzoic acid | 4-chloro-3'-methyl-5'-{[4-(trifluoromethyl)pyrimidin-2-yl]amino}biphenyl-3-carboxylic acid | 408 | 408 | Formate Salt |
| 1.103 | —CH₃ | 2-methoxy-5-substituted benzoic acid | 4-methoxy-3'-methyl-5'-{[4-(trifluoromethyl)pyrimidin-2-yl]amino}biphenyl-3-carboxylic acid | 404 | 404 | Formate Salt |
| 1.104 | —H | 2-phenyl-5-substituted benzoic acid | 3''-{[4-(trifluoromethyl)pyrimidin-2-yl]amino}-1,1':4',1''-terphenyl-2'-carboxylic acid | 436 | 436 | Formate Salt |
| 1.105 | —H | 2-(difluoromethoxy)-3-substituted benzoic acid | 2-(difluoromethoxy)-3'-{[4-(trifluoromethyl)pyrimidin-2-yl]amino}biphenyl-3-carboxylic acid | 426 | 426 | Formate Salt |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.106 | —H | (3-carboxy-4-difluoromethyl-phenyl) | 6-(difluoromethyl)-3'-{[4-(trifluoromethyl)pyrimidin-2-yl]amino}biphenyl-3-carboxylic acid | 410 | 410 | Formate Salt |
| 1.107 | —H | (3-carboxy-2-propyl-phenyl) | 2-propyl-3'-{[4-(trifluoromethyl)pyrimidin-2-yl]amino}biphenyl-3-carboxylic acid | 402 | 402 | Formate Salt |
| 1.108 | —H | (3-carboxy-2-ethyl-phenyl) | 2-ethyl-3'-{[4-(trifluoromethyl)pyrimidin-2-yl]amino}biphenyl-3-carboxylic acid | 388 | 388 | Formate Salt |
| 1.109 | —H | (3-carboxy-4-cyano-phenyl) | 6-cyano-3'-{[4-(trifluoromethyl)pyrimidin-2-yl]amino}biphenyl-3-carboxylic acid | 385 | 385 | Formate Salt |
| 1.110 | —H | (3-carboxy-4-difluoromethoxy-phenyl) | 6-(difluoromethoxy)-3'-{[4-(trifluoromethyl)pyrimidin-2-yl]amino}biphenyl-3-carboxylic acid | 426 | 426 | Formate Salt |
| 1.111 | —H | (3-carboxy-4-trifluoromethoxy-phenyl) | 6-(trifluoromethoxy)-3'-{[4-(trifluoromethyl)pyrimidin-2-yl]amino}biphenyl-3-carboxylic acid | 444 | 444 | Formate Salt |

TABLE 1.8-continued

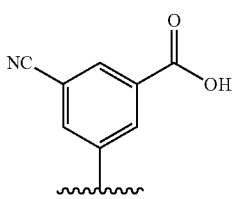 [SMILES: *c1cc(C#N)cc(C(=O)O)c1]

| Ex. No. | R⁴ | Cʸ | Name | [M + H]+ Calc'd | [M + H]+ Obsv'd | Form(s) |
|---|---|---|---|---|---|---|
| 1.112 | —H | 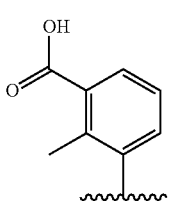 [SMILES: *c1cccc(C(=O)O)c1C] | 5-cyano-3'-{[4-(trifluoromethyl)pyrimidin-2-yl]amino}biphenyl-3-carboxylic acid | 385 | 385 | Formate Salt |
| 1.113 | —H | 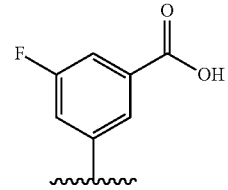 [SMILES: *c1cc(F)cc(C(=O)O)c1] | 2-methyl-3'-{[4-(trifluoromethyl)pyrimidin-2-yl]amino}biphenyl-3-carboxylic acid | 374 | 374 | Formate Salt |
| 1.114 | —H | 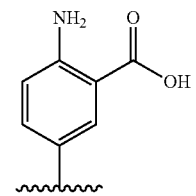 [SMILES: *c1ccc(N)c(C(=O)O)c1] | 5-fluoro-3'-{[4-(trifluoromethyl)pyrimidin-2-yl]amino}biphenyl-3-carboxylic acid | 378 | 378 | Formate Salt |
| 1.115 | —H | 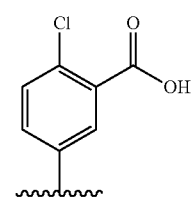 [SMILES: *c1ccc(Cl)c(C(=O)O)c1] | 4-amino-3'-{[4-(trifluoromethyl)pyrimidin-2-yl]amino}biphenyl-3-carboxylic acid | 375 | 375 | Formate Salt |
| 1.116 | —H | 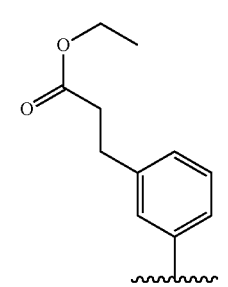 [SMILES: *c1cccc(CCC(=O)OCC)c1] | 4-chloro-3'-{[4-(trifluoromethyl)pyrimidin-2-yl]amino}biphenyl-3-carboxylic acid | 394 | 394 | Formate Salt |
| 1.117 | —CH₃ |  | ethyl 3-(3'-methyl-5'-{[4-(trifluoromethyl)pyrimidin-2-yl]amino}biphenyl-3-yl)propanoate | 430 | 430 | Formate Salt |

TABLE 1.8-continued

| Ex. No. | R⁴ | Cʸ | Name | [M + H]+ Calc'd | [M + H]+ Obsv'd | Form(s) |
|---|---|---|---|---|---|---|
| 1.118 | —CH₃ | (ethyl 3-(4-phenyl)propanoate group) | ethyl 3-(3'-methyl-5'-{[4-(trifluoromethyl)pyrimidin-2-yl]amino}biphenyl-4-yl)propanoate | 430 | 430 | Formate Salt |

TABLE 1.9

| Ex. No. | R¹ | Cʸ | Name | [M + H]+ Calc'd | [M + H]+ Obsv'd | Form(s) |
|---|---|---|---|---|---|---|
| 1.119 | —CH₃ | (trans-4-(1-hydroxy-1-phenylethyl)cyclohexanecarboxylic acid group) | trans-4-(1-hydroxy-1-{3'-methyl-5'-[(4-methylpyrimidin-2-yl)amino]biphenyl-4-yl}ethyl)cyclohexane carboxylic acid | 446 | 446 | TFA Salt |
| 1.120 | —cPr | (3-phenylpropanoic acid group) | 3-{3'-[(4-cyclopropylpyrimidin-2-yl)amino]-5'-methylbiphenyl-4-yl}propanoic acid | 374 | 374 | Formate Salt |

TABLE 1.9-continued

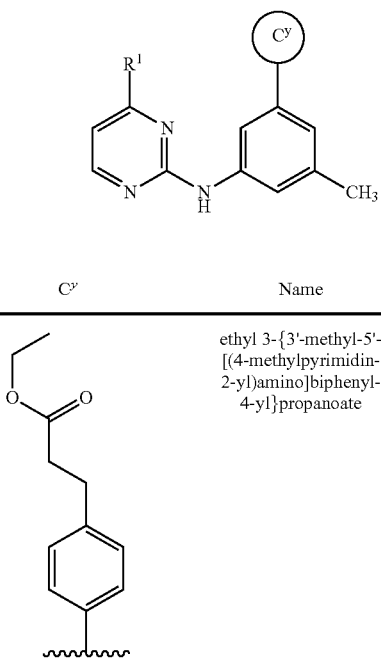

| Ex. No. | R¹ | C^y | Name | [M + H]+ Calc'd | [M + H]+ Obsv'd | Form(s) |
|---|---|---|---|---|---|---|
| 1.121 | —CH₃ | 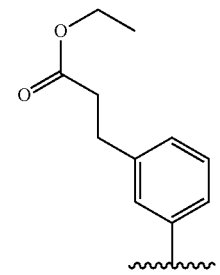 | ethyl 3-{3'-methyl-5'-[(4-methylpyrimidin-2-yl)amino]biphenyl-4-yl}propanoate | 376 | 376 | Free Base, Formate Salt |
| 1.122 | —OCH₃ | 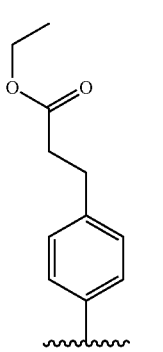 [SMILES: *c1ccc(CCC(=O)OCC)cc1] | ethyl 3-{3'-[(4-methoxypyrimidin-2-yl)amino]-5'-methylbiphenyl-3-yl}propanoate | 392 | 392 | Formate Salt |
| 1.123 | —OCH₃ | 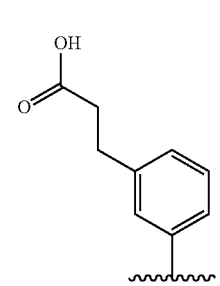 [SMILES: *c1cccc(CCC(=O)O)c1] | ethyl 3-{3'-[(4-methoxypyrimidin-2-yl)amino]-5'-methylbiphenyl-4-yl}propanoate | 392 | 392 | Formate Salt |
| 1.124 | —OCH₃ |  | 3-{3'-[(4-methoxypyrimidin-2-yl)amino]-5'-methylbiphenyl-3-yl}propanoic acid | 364 | 364 | Formate Salt |

TABLE 1.9-continued

| Ex. No. | R¹ | C^y | Name | [M + H]+ Calc'd | [M + H]+ Obsv'd | Form(s) |
|---|---|---|---|---|---|---|
| 1.125 | —OCH₃ | | 3-{3'-[(4-methoxypyrimidin-2-yl)amino]-5'-methylbiphenyl-4-yl}propanoic acid | 364 | 364 | Formate Salt |
| 1.126 | —CH₃ | | 3-{3'-methyl-5'-[(4-methylpyrimidin-2-yl)amino]biphenyl-4-yl}propanoic acid | 348 | 348 | Formate Salt |
| 1.127 | —cPr | | ethyl 3-{3'-[(4-cyclopropylpyrimidin-2-yl)amino]-5'-methylbiphenyl-3-yl}propanoate | 402 | 402 | Formate Salt |
| 1.128 | —CH₃ | | ethyl 3-{3'-methyl-5'-[(4-methylpyrimidin-2-yl)amino]biphenyl-3-yl}propanoate | 376 | 376 | Formate Salt |

TABLE 1.9-continued

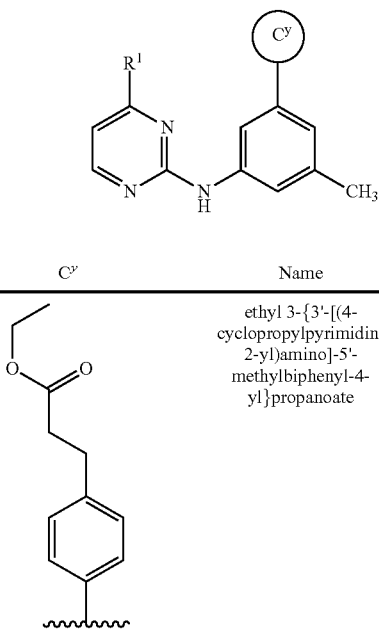

| Ex. No. | R¹ | C^y | Name | [M + H]+ Calc'd | [M + H]+ Obsv'd | Form(s) |
|---|---|---|---|---|---|---|
| 1.129 | —cPr | 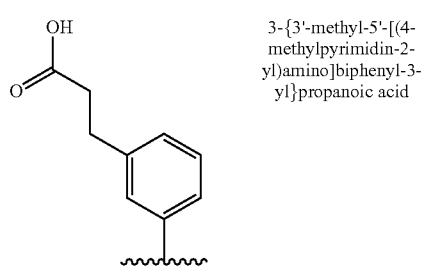 | ethyl 3-{3'-[(4-cyclopropylpyrimidin-2-yl)amino]-5'-methylbiphenyl-4-yl}propanoate | 402 | 402 | Formate Salt |
| 1.130 | —CH₃ | 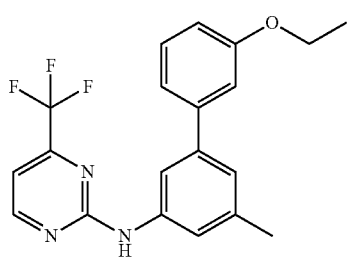 | 3-{3'-methyl-5'-[(4-methylpyrimidin-2-yl)amino]biphenyl-3-yl}propanoic acid | 348 | 348 | Formate Salt |

Example 1.131

N-(3'-ethoxy-5-methylbiphenyl-3-yl)-4-(trifluoromethyl)pyrimidin-2-amine 1.131

A mixture of N-(3-bromo-5-methylphenyl)-4-(trifluoromethyl)pyrimidin-2-amine (70 mg, 0.211 mmol), (3-ethoxyphenyl)boronic acid (70.1 mg, 0.422 mmol), PdCl₂(dppf)-CH₂Cl₂ adduct (34.4 mg, 0.042 mmol), aqueous sodium carbonate (2 M, 211 µL, 0.422 mmol), and 2-methyltetrahydrofuran (1054 µl) was heated to 60° C. for 14 hours. Upon cooling to room temperature, Si-Dimercaptotriazine (222 mg, 0.126 mmol) and acetonitrile (3 mL) were added to reaction mixture and stirred for 4 hours at room temperature. The reaction mixture was filtered and concentrated in vacuo. The residue was purified by mass triggered reverse phase HPLC (57-91% acetonitrile in water+0.1% formic acid) to afford N-(3'-ethoxy-5-methylbiphenyl-3-yl)-4-(trifluoromethyl)pyrimidin-2-amine MS ESI calc'd. for $C_{20}H_{19}F_3N_3O$ [M+H]⁺ 374, found 374. ¹H NMR (600 MHz, DMSO) δ 10.17 (s, 1H), 8.79 (d, J=4.8 Hz, 1H), 7.89 (s, 1H), 7.48 (s, 1H), 7.32 (t, J=7.9 Hz, 1H), 7.23 (d, J=4.8 Hz, 1H), 7.14 (d, J=7.8 Hz, 1H), 7.12 (s, 1H), 7.09 (d, J=2.0 Hz, 1H), 6.88 (dd, J=2.2 Hz, 8.1 Hz, 1H), 4.05 (t, J=7.0 Hz, 2H), 2.32 (s, 3H), 1.32 (t, J=7.0 Hz, 3H).

The following examples in Tables 1.10 and 1.11 were prepared in an analogous manner to that described for Example 1.131.

TABLE 1.10

| Ex. No. | R⁴ | C^y | Name | [M + H]+ Calc'd | [M + H]+ Obsv'd | Form(s) |
|---|---|---|---|---|---|---|
| 1.132 | —CF₃ | (structure: 2,2-difluoro-1-hydroxyethyl phenyl) | (1R)-2,2-difluoro-1-[3'-(trifluoromethyl)-5'-{[4-(trifluoromethyl)pyrimidin-2-yl]amino}biphenyl-4-yl]ethanol | 464 | 464 | Free Base |
| 1.133 | —CH₃ | (structure: 3-(dimethylamino)phenyl) | N~3~',N~3',5-trimethyl-N~3~-[4-(trifluoromethyl)pyrimidin-2-yl]biphenyl-3,3'-diamine | 373 | 373 | Formate Salt |
| 1.134 | —CH₃ | (structure: 3-ethoxyphenyl) | N-(3'-ethoxy-5-methylbiphenyl-3-yl)-4-(trifluoromethyl)pyrimidin-2-amine | 374 | 374 | Formate Salt |
| 1.135 | —CH₃ | (structure: 3-acetamidophenyl) | N-(3'-methyl-5'-{[4-(trifluoromethyl)pyrimidin-2-yl]amino}biphenyl-3-yl)acetamide | 387 | 387 | Formate Salt |
| 1.136 | —CH₃ | (structure: 3-(methylsulfonyl)phenyl) | N-[5-methyl-3'-(methylsulfonyl)biphenyl-3-yl]-4-(trifluoromethyl)pyrimidin-2-amine | 408 | 408 | Formate Salt |
| 1.137 | —CH₃ | (structure: 3-(benzyloxy)phenyl) | N-[3'-(benzyloxy)-5-methylbiphenyl-3-yl]-4-(trifluoromethyl)pyrimidin-2-amine | 436 | 436 | Formate Salt |

TABLE 1.10-continued

[Structure: 4-(trifluoromethyl)pyrimidin-2-yl linked via NH to a phenyl ring bearing R⁴ and Cʸ substituents]

| Ex. No. | R⁴ | Cʸ | Name | [M + H]+ Calc'd | [M + H]+ Obsv'd | Form(s) |
|---|---|---|---|---|---|---|
| 1.138 | —CH₃ | H₂N-phenyl (3-aminophenyl) | 5-methyl-N~3~-[4-(trifluoromethyl)pyrimidin-2-yl]biphenyl-3,3'-diamine | 345 | 345 | Formate Salt |
| 1.139 | —CH₃ | 3-acetylphenyl | 1-(3'-methyl-5'-{[4-(trifluoromethyl)pyrimidin-2-yl]amino}biphenyl-3-yl)ethanone | 372 | 372 | Formate Salt |

TABLE 1.11

[Structure: 4-R¹-pyrimidin-2-yl linked via NH to a 3-methyl-5-Cʸ-phenyl ring]

| Ex. No. | R¹ | Cʸ | Name | [M + H]+ Calc'd | [M + H]+ Obsv'd | Form(s) |
|---|---|---|---|---|---|---|
| 1.140 | —cPr | 3-(2-carboxyethyl)phenyl | 3-{3'-[(4-cyclopropylpyrimidin-2-yl)amino]-5'-methylbiphenyl-3-yl}propanoic acid | 374 | 374 | Ammonium Salt |
| 1.141 | —OCH₃ | 3-carboxyphenyl | 3'-[(4-methoxypyrimidin-2-yl)amino]-5'-methylbiphenyl-3-carboxylic acid | 336 | 336 | Free Base |

TABLE 1.11-continued

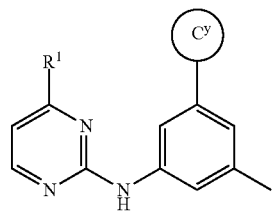

| Ex. No. | R¹ | C^y | Name | [M + H]+ Calc'd | [M + H]+ Obsv'd | Form(s) |
|---|---|---|---|---|---|---|
| 1.142 | —CH₃ | ![benzoic acid] | 3'-methyl-5'-[(4-methylpyrimidin-2-yl)amino]biphenyl-3-carboxylic acid | 320 | 320 | Free Base |

Example 1.143

2-(Biphenyl-3-ylamino)-4-(2,8-diazaspiro[4.5]dec-8-yl)pyrimidine-5-carbonitrile

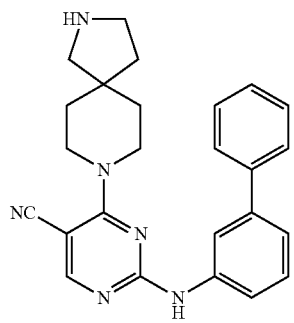

1.143

Step 1:

tert-Butyl 2,8-diazaspiro[4.5]decane-2-carboxylate (69 mg, 0.287 mol) was added to a cooled solution of the 2,4-dichloropyrimidine-5-carbonitrile (50 mg, 0.287 mmol) and Hunig's base (50 uL, 0.287 mmol) in $CH_2Cl_2$ (1.5 mL) and the reaction mixture was stirred for 3 hours at 0° C. The solvent was removed under reduced pressure, then the mixture was diluted with $CH_3CN$ (2 mL) and the biphenyl-3-amine (97 mg, 0.575 mol) was added. The mixture was then heated to 80° C. overnight. Upon cooling, the reaction mixture was diluted with ethyl acetate, washed with $H_2O$ and then brine and the organic extracts were dried ($Na_2SO_4$), filtered and concentrated in vacuo. The residue was purified by silica gel chromatography (ethyl acetate/hexanes) provided a mixture of the two possible isomers which was separated by the reverse phase chromatography to afford tert-butyl 8-[2-(biphenyl-3-ylamino)-5-cyanopyrimidin-4-yl]-2,8-diazaspiro[4.5]decane-2-carboxylate. MS ESI calcd. for $C_{30}H_{35}N_6O_2$ [M+H]⁺ 511, found 511.

Step 2:

TFA (1 mL) was added to a solution of the tert-butyl 8-[2-(biphenyl-3-ylamino)-5-cyanopyrimidin-4-yl]-2,8-diazaspiro[4.5]decane-2-carboxylate (24 mg, 0.047 mmol) in $CH_2Cl_2$ (1 mL) was added and stirred at room temperature for 1 hour. The reaction mixture was concentrated in vacuo to afford 2-(biphenyl-3-ylamino)-4-(2,8-diazaspiro[4.5]dec-8-yl)pyrimidine-5-carbonitrile as a white solid. MS ESI calcd. for $C_{25}H_{27}N_6$ [M+H]⁺ 411, found 411. ¹H NMR (400 MHz, DMSO) δ 10.25 (s, 1H), 9.08 (s, 1H), 8.72 (s, 1H), 8.32 (s, 1H), 7.87 (d, 7.9 Hz, 2H), 7.85 (s, 1H), 7.74 (t, J=7.6 Hz, 2H), 7.69-7.59 (m, 2H), 7.57 (d, J=7.8 Hz, 1H), 4.31-4.14 (m, 2H), 4.14-4.04 (m, 2H), 3.65-3.43 (m, 2H), 3.32 (t, J=5.6 Hz, 2H), 2.13 (t, J=7.4 Hz, 2H), 1.94-1.92 (br m, 4H).

Example 1.144

(1S)-2,2-Difluoro-1-(3'-fluoro-5'-{[4-(trifluoromethyl)pyrimidin-2-yl]amino}biphenyl-4-yl)ethanol

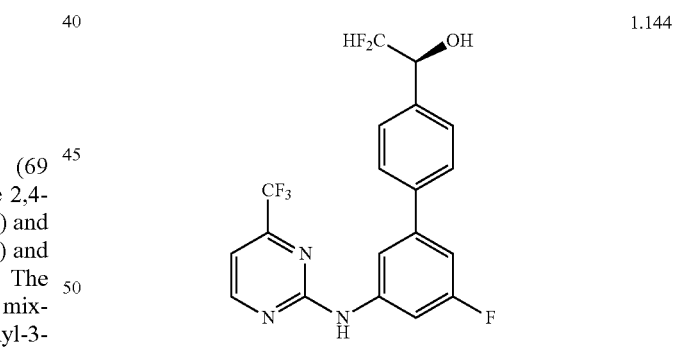

1.144

Step 1:

A mixture of $PdCl_2$ (dppf)—dichloromethane adduct (40.8 mg, 0.050 mmol), 1-fluoro-3-iodo-5-nitrobenzene (267 mg, 1.00 mmol), {4-[(1S)-2,2-difluoro-1-hydroxyethyl]phenyl}boronic acid (222 mg, 1.10 mmol), sodium carbonate (1.50 mL, 3.00 mmol) and DMF (5 mL) was degassed by sparging with nitrogen and then heated to 85° C. for 3 hours. Upon cooling to room temperature, the reaction mixture was diluted with water, and aqueous $NH_4Cl$, extracted with ethyl acetate, washed with brine, dried over sodium sulfate, filtered, and concentrated in vacuo. The residue was purified by silica gel column chromatography (ethyl acetate/hexanes) to give (1S)-2,2-difluoro-1-(3'-fluoro-5'-nitrobiphenyl-4-yl)ethanol. MS ESI calc'd. for $C_{14}H_{11}F_3NO_3$[M+H]⁺ 298, found 298.

Step 2:

Ammonium chloride (24.2 mg, 0.453 mmol) was added to a mixture of (1S)-2,2-difluoro-1-(3'-fluoro-5'-nitrobiphenyl-4-yl)ethanol (269 mg, 0.905 mmol) and iron (253 mg, 4.53 mmol) in ethanol (6 mL) and water (3 mL). The mixture was heated to reflux for 1.5 hours. Upon cooling to room temperature, the reaction mixture was filtered through CELITE and washed with ethyl acetate. The filtrate was washed with saturated aqueous $NaHCO_3$ and brine, dried over sodium sulfate, filtered, and concentrated in vacuo. The residue was purified by silica gel chromatography (ethyl acetate/hexanes) to yield (1S)-1-(3'-amino-5'-fluorobiphenyl-4-yl)-2,2-difluoroethanol. MS ESI calc'd. for $C_{14}H_{13}F_3NO$ $[M+H]^+$ 268, found 268.

Step 3:

Palladium(II) acetate (33.5 mg, 0.149 mmol) was added to a mixture of (1S)-1-(3'-amino-5'-fluorobiphenyl-4-yl)-2,2-difluoroethanol (222 mg, 0.747 mmol), cesium carbonate (487 mg, 1.494 mmol), and 2-chloro-4-(trifluoromethyl)pyrimidine (143 mg, 0.784 mmol) in degassed (by sparging with Argon) dioxane (8 mL). The mixture was heated to 110° C. for 5 hours. Upon cooling to room temperature, the reaction mixture was diluted with saturated aqueous $NaHCO_3$, extracted with ethyl acetate, washed with brine, dried over sodium sulfate, filtered, and concentrated in vacuo. The residue was purified by silica gel column chromatography (ethyl acetate/toluene) to afford (1S)-2,2-difluoro-1-(3'-fluoro-5'-{[4-(trifluoromethyl)pyrimidin-2-yl]amino}biphenyl-4-yl)ethanol. MS ESI calc'd. for $C_{19}H_{14}F_6N_3O$ $[M+H]^+$ 414, found 414. $^1H$ NMR (500 MHz, Acetone-$d_6$): δ 9.48 (s, 1H); 8.89 (d, J=4.9 Hz, 1H); 8.02 (d, J=2.1 Hz, 1H); 7.89 (dd, J=11.4, 2.4 Hz, 1H); 7.76 (d, J=8.0 Hz, 2H); 7.63 (d, J=8.0 Hz, 2H); 7.32 (d, J=4.9 Hz, 1H); 7.19-7.15 (m, 1H); 6.01 (td, J=55.9, 4.3 Hz, 1H); 5.37 (d, J=4.9 Hz, 1H); 5.00-4.93 (m, 1H).

The following examples in Table 1.12 were prepared in an analogous manner to that described for Example 1.144.

Example 2

Preparation of Compounds of Formula (I) Using the General Methods Illustrated in Scheme 2

Example 2.1

(1R)-1-(3'-Amino-5'-{[4-(trifluoromethyl)pyrimidin-2-yl]amino}biphenyl-4-yl)-2,2-difluoroethanol

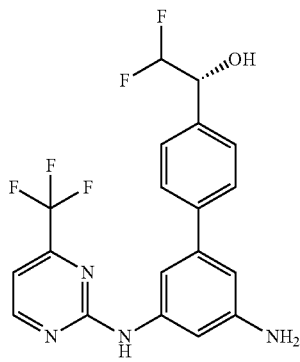

Step 1:

A mixture of 1-bromo-3,5-dinitrobenzene (5 g, 19.6 mmol), $PdCl_2$(dppf)-dichloromethane adduct (0.802 g, 0.982 mmol), {4-[(1R)-2,2-difluoro-1-hydroxyethyl]phenyl}boronic acid (4.36 g, 21.6 mmol), and aqueous sodium carbonate (2 M, 29.5 mL, 58.9 mmol) in dioxane (65.6 mL) was degassed by sparging with nitrogen. The mixture was heated to 85° C. for 2 hours, and then allowed to cool to room temperature. The mixture was diluted with water,

TABLE 1.12

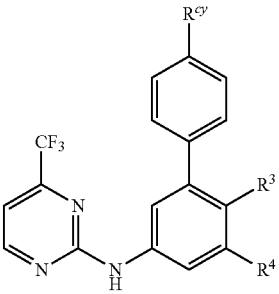

| Ex. No. | $R^3$ | $R^4$ | $R^{Cy'}$ | Name | $[M+H]^+$ Calc'd | $[M+H]^+$ Obsv'd | Form(s) |
|---|---|---|---|---|---|---|---|
| 1.145 | —H | —OCH$_2$CH$_3$ | (F, F, OH structure) | (1R)-1-(3'-ethoxy-5'-{[4-(trifluoromethyl)pyrimidin-2-yl]amino}biphenyl-4-yl)-2,2-difluoroethanol | 440 | 440 | Free Base |
| 1.146 | —F | —H | (F, F, OH structure) | (1R)-2,2-difluoro-1-(2'-fluoro-5'-{[4-(trifluoromethyl)pyrimidin-2-yl]amino}biphenyl-4-yl)ethanol | 414 | 414 | Free Base | extracted with ethyl acetate, washed with brine, dried over sodium sulfate, filtered and concentrated in vacuo. The residue was purified by silica gel column chromatography (ethyl acetate/hexanes) to give (1R)-1-(3',5'-dinitrobiphenyl-4-yl)-2,2-difluoroethanol as an off-white solid. MS ESI calc'd. for $C_{14}H_9F_2N_2O_4[M+H-H_2O]^+$ 307, found 307.

Step 2:

Ammonium chloride (102 mg, 1.91 mmol) was added to a stirred (room temperature) mixture of (1R)-1-(3',5'-dinitrobiphenyl-4-yl)-2,2-difluoroethanol (517 mg, 1.60 mmol) and iron (1070 mg, 19.1 mmol) in ethanol (5.32 mL) and water (2.66 mL), and then the reaction mixture was stirred at 80° C. for 2 hours. The reaction mixture was filtered over CELITE while still warm. The filtrate was concentrated in vacuo, diluted with water, extracted with ethyl acetate, washed with brine, dried over magnesium sulfate, filtered, and concentrated in vacuo. The residue was purified by silica gel column chromatography (ethyl acetate/hexanes) afforded (1R)-1-(3', 5'-diaminobiphenyl-4-yl)-2,2-difluoroethanol. MS ESI calc'd. for $C_{14}H_{15}F_2N_2O$ $[M+H]^+$ 265, found 265.

Step 3:

A mixture of 2-chloro-4-(trifluoromethyl)pyrimidine (76 mg, 0.416 mmol), Xantphos (65.7 mg, 0.114 mmol), palladium(II) acetate (17.0 mg, 0.076 mmol), and cesium carbonate (247 mg, 0.757 mmol) in dioxane (1.89 mL) was degassed by sparging with nitrogen and heated to 105° C. for 2 hours. The mixture was allowed to cool to room temperature, diluted with ethyl acetate (20 mL), and partitioned with water. The organic layer was concentrated under reduced pressure, and the resultant residue was purified by silica gel column chromatography (ethyl acetate/hexanes) to give (1R)-1-(3'-amino-5'-{[4-(trifluoromethyl)pyrimidin-2-yl]amino}biphenyl-4-yl)-2,2-difluoroethanol as a dark beige solid. MS ESI calc'd. for $C_{19}H_{16}F_5N_4O$ $[M+H]^+$ 411, found 411. $^1$H NMR (400 MHz, DMSO-d$_6$): δ 10.02 (s, 1H); 8.79 (d, J=4.8 Hz, 1H); 7.57-7.44 (m, 4H); 7.30 (s, 1H); 7.22 (d, J=4.8 Hz, 1H); 6.94 (s, 1H); 6.55 (s, 1H); 6.23-6.03 (m, 2H); 5.19 (s, 2H); 4.79 (s, 1H).

Example 2.2

3-(4'-[(1R)-2,2-difluoro-1-hydroxyethyl]-5-{[4-(trifluoromethyl)pyrimidin-2-yl]amino}biphenyl-3-yl)-1, 3-oxazolidin-2-one

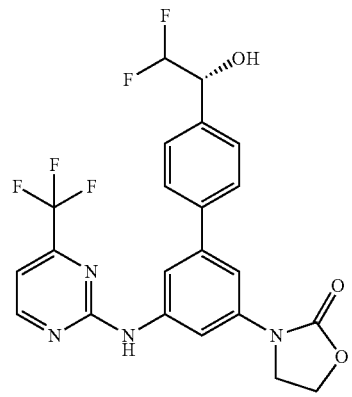

2.2

2-Chloroethyl chloroformate (12.58 μL, 0.122 mmol) was slowly added to a stirred, cooled (0° C.) mixture of (1R)-1-(3'-amino-5'-{[4-(trifluoromethyl)pyrimidin-2-yl]amino}biphenyl-4-yl)-2,2-difluoroethanol (40 mg, 0.097 mmol) and potassium carbonate (33.7 mg, 0.244 mmol) in acetonitrile (0.5 mL). The mixture was stirred at room temperature for 1 hour. The mixture was then heated and stirred at 80° C. for 3 hours, then allowed to cool to room temperature. The mixture was diluted with ethyl acetate and concentrated in vacuo. Purification via silica gel column chromatography (20-80% ethyl acetate in hexanes) to give 3-(4'-[(1R)-2,2-difluoro-1-hydroxyethyl]-5-{[4-(trifluoromethyl)pyrimidin-2-yl]amino}biphenyl-3-yl)-1,3-oxazolidin-2-one as a colorless solid. MS ESI calc'd. for $C_{22}H_{18}F_5N_4O_3$ $[M+H]^+$ 481, found 481. $^1$H NMR (500 MHz, DMSO-d$_6$): δ 10.39 (s, 1H); 8.85 (d, J=4.9 Hz, 1H); 8.01 (s, 1H); 7.88 (s, 1H); 7.64 (d, J=7.8 Hz, 2H); 7.55 (t, J=8.9 Hz, 3H); 7.31 (d, J=4.8 Hz, 1H); 6.27 (d, J=4.8 Hz, 1H); 6.07 (td, J=55.5, 3.9 Hz, 1H); 4.83 (s, 1H); 4.48 (t, J=7.8 Hz, 2H); 4.13 (t, J=7.9 Hz, 2H).

The following examples in Table 2 were prepared in an analogous manner to that described for Example 2.2 using triethylamine as a base and dichloromethane as a solvent.

TABLE 2

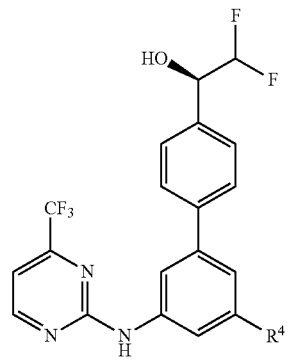

| Ex. No. | R$^4$ | Name | [M + H]+ Calc'd | [M + H]+ Obsv'd | Form(s) |
|---|---|---|---|---|---|
| 2.3 | —N(H)C(O)CH$_3$ | N-(4'-[(1R)-2,2-difluoro-1-hydroxyethyl]-5-{[4-(trifluoromethyl)pyrimidin-2-yl]amino}biphenyl-3-yl)acetamide | 453 | 453 | Free Base |

TABLE 2-continued

| Ex. No. | R⁴ | Name | [M + H]+ Calc'd | [M + H]+ Obsv'd | Form(s) |
|---|---|---|---|---|---|
| 2.4 | -NH-C(=O)-C₆H₄-Cl (4-chlorobenzamide) | 4-chloro-N-(4'-[(1R)-2,2-difluoro-1-hydroxyethyl]-5-{[4-(trifluoromethyl)pyrimidin-2-yl]amino}biphenyl-3-yl)benzamide | 549 | 549 | Free Base |
| 2.5 | -NH-SO₂-C₆H₄-Cl (4-chlorobenzenesulfonamide) | 4-chloro-N-(4'-[(1R)-2,2-difluoro-1-hydroxyethyl]-5-{[4-(trifluoromethyl)pyrimidin-2-yl]amino}biphenyl-3-yl)benzenesulfonamide | 585 | 585 | Free Base |
| 2.6 | -NH-SO₂-CH₃ | N-(4'-[(1R)-2,2-difluoro-1-hydroxyethyl]-5-{[4-(trifluoromethyl)pyrimidin-2-yl]amino}biphenyl-3-yl)methanesulfonamide | 489 | 489 | Free Base |
| 2.7 | -NH-C(=O)-NH-SO₂-C₆H₄-Cl | 4-chloro-N-[(4'-[(1R)-2,2-difluoro-1-hydroxyethyl]-5-{[4-(trifluoromethyl)pyrimidin-2-yl]amino}biphenyl-3-yl)carbamoyl]benzenesulfonamide | 628 | 628 | Free Base |
| 2.8 | -NH-C(=O)-NH-CH₂CH₃ | 1-(4'-[(1R)-2,2-difluoro-1-hydroxyethyl]-5-{[4-(trifluoromethyl)pyrimidin-2-yl]amino}biphenyl-3-yl)-3-ethylurea | 482 | 482 | Free Base |
| 2.9 | -NH-C(=O)-NH-C₆H₄-Cl | 1-(4-chlorophenyl)-3-(4'-[(1R)-2,2-difluoro-1-hydroxyethyl]-5-{[4-(trifluoromethyl)pyrimidin-2-yl]amino}biphenyl-3-yl)urea | 564 | 564 | Free Base |

Example 2.10

(1R)-2,2-Difluoro-1-(3'-[(2,2,2-trifluoroethyl)amino]-5'-{[4-(trifluoromethyl)pyrimidin-2-yl]amino}biphenyl-4-yl)ethanol

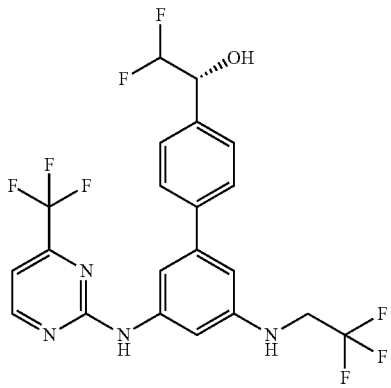

2.10

Trifluoroacetic acid (0.5 mL) was added to a cooled (0° C.) mixture of (1R)-1-(3'-amino-5'-{[4-(trifluoromethyl)pyrimidin-2-yl]amino}biphenyl-4-yl)-2,2-difluoroethanol (100 mg, 0.244 mmol) and sodium cyanoborohydride (30.6 mg, 0.487 mmol) in dichloromethane (0.5 mL) at 0° C. Trifluoroacetaldehyde (85 mg, 0.731 mmol) was added to the reaction mixture, and then stirred at room temperature for 3 hours. Aqueous sodium carbonate was added to the reaction mixture, extracted with ethyl acetate and the combined organic layers were concentrated under reduced pressure. The residue was purified by silica gel column chromatography (ethyl acetate/hexanes) to give (1R)-2,2-difluoro-1-(3'-[(2,2,2-trifluoroethyl)amino]-5'-{[4-(trifluoromethyl)pyrimidin-2-yl]amino}biphenyl-4-yl)ethanol as a yellow solid. MS ESI calc'd. for $C_{21}H_{17}F_8N_4O$ [M+H] 493. found 493. $^1$H NMR (400 MHz, CDCl$_3$): δ 8.66 (d, J=5.0 Hz, 1H); 7.70 (s, 1H); 7.63 (d, J=8.0 Hz, 2H); 7.52 (d, J=8.0 Hz, 2H); 7.39 (s, 1H); 7.13 (s, 1H); 7.08 (d, J=5.0 Hz, 1H); 6.65 (s, 1H); 5.83 (td, J=56.0, 4.8 Hz, 1H); 4.91 (td, J=10.1, 4.8 Hz, 1H); 3.87 (q, J=8.9 Hz, 2H).

Example 3

Preparation of Compounds of Formula (I) using the General Methods Illustrated in Scheme 3

Example 3.1

3'-Methyl-N-(methylsulfonyl)-5'-{[4-(trifluoromethyl)pyrimidin-2-yl]amino}biphenyl-3-carboxamide

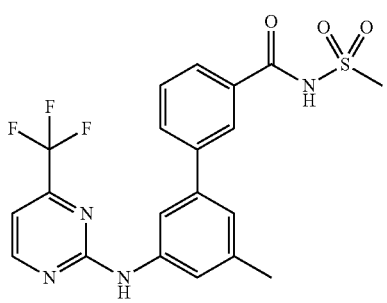

3.1

Step 1:
A suspension of N-[3-methyl-5-(4,4,5,5-tetramethyl-1,3,2-dioxaborolan-2-yl)phenyl]-4-(trifluoromethyl)pyrimidin-2-amine (1.00 g, 2.64 mmol), methyl 3-bromobenzoate (0.581 g, 2.70 mmol), 1,1'-bis(diphenylphosphino)ferrocene-palladium(II)dichloride dichloromethane complex (0.054 g, 0.066 mmol), 1,4-dioxane (10 mL), and aqueous sodium carbonate (2 M, 2.64 mL, 5.27 mmol) was placed under an argon atmosphere by performing 6 vacuum/argon cycles. The reaction mixture was then heated to 160° C. for 10 minutes in a microwave reactor. The resulting suspension was diluted with ethyl acetate (75 mL) and saturated aqueous sodium bicarbonate solution (25 mL). The layers were separated, and the organic layer was washed with water (10 mL) and then brine (25 mL), dried over sodium sulfate, filtered, and concentrated under reduced pressure. The residue was purified by chromatography on silica gel (ethyl acetate/hexanes) to afford methyl 3'-methyl-5'-{[4-(trifluoromethyl)pyrimidin-2-yl]amino}biphenyl-3-carboxylate. MS ESI calc'd. for $C_{20}H_{17}F_3N_3O_2$ [M+H]$^+$ 388, found 388.

Step 2:
A suspension of methyl 3'-methyl-5'-{[4-(trifluoromethyl)pyrimidin-2-yl]amino}biphenyl-3-carboxylate (550 mg, 1.420 mmol) and aqueous sodium hydroxide (1 M, 1.63 mL, 1.63 mmol) in methanol (9 mL) was heated to 110° C. for 10 minutes in a microwave reactor. The reaction mixture was then diluted with aqueous hydrochloric acid (2 M, 0.89 mL, 1.78 mmol), brine (20 mL), and ethyl acetate (50 mL). The layers were separated and the aqueous layer was extracted with ethyl acetate (15 mL). The combined organic layers were washed with brine (20 mL), dried over sodium sulfate, filtered, and concentrated under reduced pressure to yield 3'-methyl-5'-{[4-(trifluoromethyl)pyrimidin-2-yl]amino}biphenyl-3-carboxylic acid. MS ESI calc'd. for $C_{19}H_{15}F_3N_3O_2$ [M+H]$^+$ 374, found 374.

Step 3:
A cloudy solution of 3'-methyl-5'-{[4-(trifluoromethyl)pyrimidin-2-yl]amino}biphenyl-3-carboxylic acid (100 mg, 0.222 mmol), methanesulfonamide (24.3 mg, 0.256 mmol), DMAP (5.4 mg, 0.044 mmol), EDC (59.7 mg, 0.311 mmol), and triethylamine (0.043 mL, 0.31 mmol) in DMF (4 mL) was stirred for 14 hours at room temperature. The reaction mixture was purified directly via reverse phase HPLC (CH$_3$CN: H$_2$O with 0.1% TFA) to give 3'-methyl-N-(methylsulfonyl)-5'-{[4-(trifluoromethyl)pyrimidin-2-yl]amino}biphenyl-3-carboxamide. MS ESI calc'd. for $C_{20}H_{18}F_3N_4O_3S$ [M+H]$^+$ 451, found 451. $^1$H NMR (500 MHz, DMSO-d$_6$) δ 12.26 (s, 1H), 10.26 (s, 1H), 8.82 (d, J=4.9 Hz, 1H), 8.18 (s, 1H), 7.95 (s, 1H), 7.90 (d, J=7.8 Hz, 1H), 7.87 (d, J=7.9 Hz, 1H), 7.61 (t, J=7.8 Hz, 1H), 7.57 (s, 1H), 7.26 (d, J=5.0 Hz, 1H), 7.24 (s, 1H), 3.39 (s, 3H), 2.38 (s, 3H).

Example 3.2

N-[5-Methyl-3'-(1H-tetrazol-5-yl)biphenyl-3-yl]-4-(trifluoromethyl)pyrimidin-2-amine

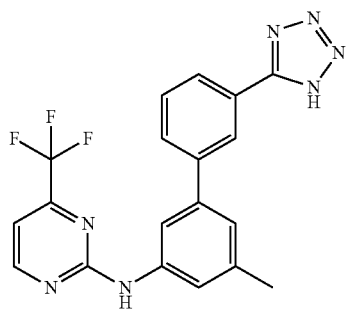

3.2

Step 1:

A suspension of N-[3-methyl-5-(4,4,5,5-tetramethyl-1,3,2-dioxaborolan-2-yl)phenyl]-4-(trifluoromethyl)pyrimidin-2-amine (1.00 g, 2.64 mmol), 3-bromobenzonitrile (0.492 g, 2.70 mmol), 1,1'-bis(diphenylphosphino)ferrocene-palladium(II)dichloride dichloromethane complex (0.054 g, 0.066 mmol), 1,4-dioxane (10 mL), and aqueous sodium carbonate (2 M, 2.64 mL, 5.27 mmol) was placed under an argon atmosphere by performing 6 vacuum/argon cycles. The reaction mixture was then heated to 160° C. for 10 minutes using a microwave reactor. The resulting suspension was diluted with ethyl acetate (75 mL) and saturated aqueous sodium bicarbonate (25 mL). The layers were separated, and the organic layer was washed with water (10 mL) and then brine (25 mL), dried over sodium sulfate, filtered, and concentrated under reduced pressure. The residue was purified by chromatography on silica gel (ethyl acetate/hexanes) to afford 3'-methyl-5'-{[4-(trifluoromethyl)pyrimidin-2-yl]amino}biphenyl-3-carbonitrile. MS ESI calc'd. for $C_{19}H_{14}F_3N_4$ $[M+H]^+$ 355, found 355.

Step 2:

A suspension of 3'-methyl-5'-{[4-(trifluoromethyl)pyrimidin-2-yl]amino}biphenyl-3-carbonitrile (354 mg, 1.00 mmol), zinc bromide (225 mg, 1.00 mmol), and sodium azide (68.3 mg, 1.05 mmol) in water (2 mL) was heated to 115° C. for 24 hours. The reaction mixture was then diluted with ethyl acetate (15 mL) and aqueous 2 M hydrochloric acid (2.25 mL) to give two layers. The layers were separated and the aqueous layer was extracted with ethyl acetate (15 mL). The combined organic layers were washed with brine, dried over sodium sulfate, filtered, and concentrated under reduced pressure. The residue was purified via reverse phase HPLC to yield N-[5-methyl-3'-(1H-tetrazol-5-yl)biphenyl-3-yl]-4-(trifluoromethyl)pyrimidin-2-amine MS ESI calc'd. for $C_{19}H_{15}F_3N_7$ $[M+H]^+$ 398, found 398. $^1$H NMR (500 MHz, DMSO-$d_6$) δ 10.28 (s, 1H), 8.83 (d, J=4.9 Hz, 1H), 8.30 (s, 1H), 8.02 (d, J=7.8 Hz, 1H), 7.99 (s, 1H), 7.82 (d, J=7.9 Hz, 1H), 7.70 (t, J=7.8 Hz, 1H), 7.59 (s, 1H), 7.27 (d, J=4.9 Hz, 1H), 7.24 (s, 1H), 2.38 (s, 3H).

Example 3.3

3'-Methyl-4-(2-methylpropoxy)-5'-{[4-(trifluoromethyl)pyrimidin-2-yl]amino}biphenyl-3-carboxylic acid 3.3

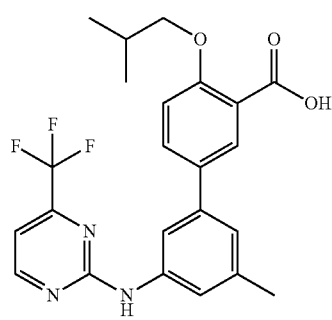

Step 1:

A mixture of methyl 2-hydroxy-5-iodobenzoate (11.6 g, 41.5 mmol) in 2-methyl-THF (180 mL) and water (82.5 mL) was purged with $N_2$ for 30 minutes. Sodium carbonate (12.6 g, 119 mmol), N-[3-methyl-5-(4,4,5,5-tetramethyl-1,3,2-dioxaborolan-2-yl)phenyl]-4-(trifluoromethyl)pyrimidin-2-amine (15.0 g, 39.6 mmol) and [1,1-bis(diphenylphosphino)ferrocene]dichloropalladium(II) (1.61 g, 1.98 mmol) were added to the reaction mixture at rt under $N_2$ and then the mixture was heated to 80° C. for 14 hours. The reaction mixture was poured into a 1:1 solution of ethyl acetate/2N HCl (800 mL) and the layers were separated. The organic layer was dried over $Na_2SO_4$, filtered, and concentrated in vacuo. The residue was purified by silica gel column chromatography (ethyl acetate/hexanes) to afford methyl 4-hydroxy-3'-methyl-5'-{[4-(trifluoromethyl)pyrimidin-2-yl]amino}biphenyl-3-carboxylate. MS ESI calcd. for $C_{20}H_{12}F_3N_3O_3$ $[M+H]^+$ 404, found 404.

Step 2:

A mixture of PS-triphenylphosphine (0.057 g, 0.220 mmol), methyl 4-hydroxy-3'-methyl-5'-{[4-(trifluoromethyl)pyrimidin-2-yl]amino}biphenyl-3-carboxylate (0.040 g, 0.1 mmol) and THF (1.33 mL) was stirred for 5 minutes at room temperature, then a solution of di-tert-butylazodicarboxylate (0.037 g, 0.160 mmol) in THF (0.33 mL) was added. The reaction mixture was stirred for 30 minutes, then a solution of 2-methylpropan-1-ol (9.0 mg, 0.120 mmol) in THF (0.33 mL) was added, and the reaction mixture was stirred for 48 hours at room temperature. A 1:1 mixture of MeOH:NaOH (1 mL, 1N) was added to the reaction mixture and then stirred at 50° C. for 6 hours. The mixture was filtered, washing with DMSO (1 mL), and concentrated under reduced pressure. The residue was dissolved in DMSO (2 mL) and purified by mass triggered reverse phase HPLC to give 3'-methyl-4-(2-methylpropoxy)-5'-{[4-(trifluoromethyl)pyrimidin-2-yl]amino}biphenyl-3-carboxylic acid. MS ESI calcd. for $C_{23}H_{23}F_3N_3O_3$ $[M+H]^+$ 446, found 446. $^1$H NMR (600 MHz, DMSO-$d_6$) δ 10.17 (s, 1H), 8.79 (d, J=4.9 Hz, 1H), 7.86 (s, 1H), 7.84 (s, 1H), 7.69 (d, J=8.7 Hz, 1H), 7.48 (s, 1H), 7.23 (d, J=4.9 Hz, 1H), 7.16 (d, J=8.7 Hz, 1H), 7.09 (s, 1H), 3.82 (d, J=6.4 Hz, 2H), 2.37-2.27 (m, 3H), 2.01 (dt, J=13.3 Hz, 6.6 Hz, 1H), 0.97 (d, J=6.7 Hz, 6H).

The following examples in Table 3.1 were prepared in an analogous manner to that described for Example 3.3.

TABLE 3.1

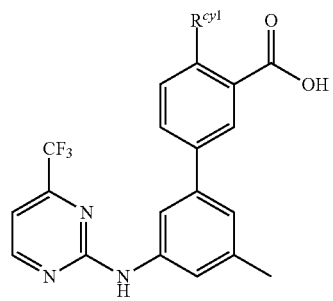

| Ex. No. | R<sup>cyl</sup> | Name | [M + H]+ Calc'd | [M + H]+ Obsv'd | Form(s) |
|---|---|---|---|---|---|
| 3.4 | | 4-(2-fluoroethoxy)-3'-methyl-5'-{[4-(trifluoromethyl)pyrimidin-2-yl]amino}biphenyl-3-carboxylic acid | 436 | 436 | Ammonium Salt |
| 3.5 | | 4-(cyclopentyloxy)-3'-methyl-5'-{[4-(trifluoromethyl)pyrimidin-2-yl]amino}biphenyl-3-carboxylic acid | 458 | 458 | Ammonium Salt |
| 3.6 | | 4-(cyclopropylmethoxy)-3'-methyl-5'-{[4-(trifluoromethyl)pyrimidin-2-yl]amino}biphenyl-3-carboxylic acid | 444 | 444 | Ammonium Salt |
| 3.7 | | 4-(cyclohexyloxy)-3'-methyl-5'-{[4-(trifluoromethyl)pyrimidin-2-yl]amino}biphenyl-3-carboxylic acid | 472 | 472 | Ammonium Salt |
| 3.8 | | 4-(benzyloxy)-3'-methyl-5'-{[4-(trifluoromethyl)pyrimidin-2-yl]amino}biphenyl-3-carboxylic acid | 480 | 480 | Ammonium Salt |
| 3.9 | | 3'-methyl-4-(3-phenylpropoxy)-5'-{[4-(trifluoromethyl)pyrimidin-2-yl]amino}biphenyl-3-carboxylic acid | 508 | 508 | Ammonium Salt |

TABLE 3.1-continued

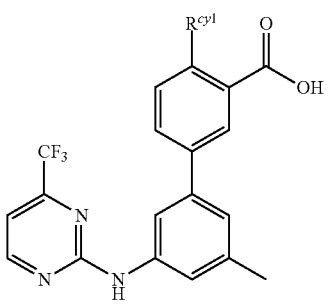

| Ex. No. | R$^{cyl}$ | Name | [M + H]+ Calc'd | [M + H]+ Obsv'd | Form(s) |
|---|---|---|---|---|---|
| 3.10 | (2-phenylethoxy) | 3'-methyl-4-(2-phenylethoxy)-5'-{[4-(trifluoromethyl)pyrimidin-2-yl]amino}biphenyl-3-carboxylic acid | 494 | 494 | Ammonium Salt |
| 3.11 | (3-fluorobenzyl)oxy | 4-[(3-fluorobenzyl)oxy]-3'-methyl-5'-{[4-(trifluoromethyl)pyrimidin-2-yl]amino}biphenyl-3-carboxylic acid | 498 | 498 | Ammonium Salt |
| 3.12 | naphthalen-2-ylmethoxy | 3'-methyl-4-(naphthalen-2-ylmethoxy)-5'-{[4-(trifluoromethyl)pyrimidin-2-yl]amino}biphenyl-3-carboxylic acid | 530 | 530 | Ammonium Salt |
| 3.13 | 2-naphthalen-1-ylethoxy | 3'-methyl-4-(2-naphthalen-1-ylethoxy)-5'-{[4-(trifluoromethyl)pyrimidin-2-yl]amino}biphenyl-3-carboxylic acid | 544 | 544 | Ammonium Salt |
| 3.14 | 2,3-dihydro-1H-inden-2-yloxy | 4-(2,3-dihydro-1H-inden-2-yloxy)-3'-methyl-5'-{[4-(trifluoromethyl)pyrimidin-2-yl]amino}biphenyl-3-carboxylic acid | 506 | 506 | Ammonium Salt |
| 3.15 | 2-methoxyethoxy | (2-methoxyethoxy)-3'-methyl-5'-{[4-(trifluoromethyl)pyrimidin-2-yl]amino}biphenyl-3-carboxylic acid | 448 | 448 | Ammonium Salt |

TABLE 3.1-continued

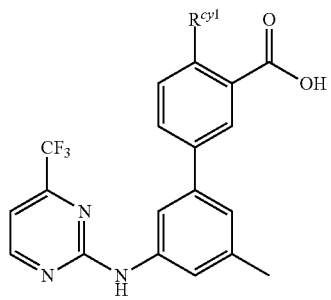

| Ex. No. | $R^{cy1}$ | Name | [M + H]+ Calc'd | [M + H]+ Obsv'd | Form(s) |
|---|---|---|---|---|---|
| 3.16 | (3-methoxypropoxy group) | 4-(3-methoxypropoxy)-3'-methyl-5'-{[4-(trifluoromethyl)pyrimidin-2-yl]amino}biphenyl-3-carboxylic acid | 462 | 462 | Ammonium Salt |
| 3..17 | (tetrahydrofuran-3-yloxy, racemic) | 3'-methyl-4-(tetrahydrofuran-3-yloxy)-5'-{[4-(trifluoromethyl)pyrimidin-2-yl]amino}biphenyl-3-carboxylic acid | 460 | 460 | Ammonium Salt |
| 3.18 | (tetrahydro-2H-pyran-4-yloxy) | 3'-methyl-4-(tetrahydro-2H-pyran-4-yloxy)-5'-{[4-(trifluoromethyl)pyrimidin-2-yl]amino}biphenyl-3-carboxylic acid | 474 | 474 | Ammonium Salt |
| 3.19 | (2-(2-oxopyrrolidin-1-yl)ethoxy) | 3'-methyl-4-[2-(2-oxopyrrolidin-1-yl)ethoxy]-5'-{[4-(trifluoromethyl)pyrimidin-2-yl]amino}biphenyl-3-carboxylic acid | 501 | 501 | Ammonium Salt |
| 3.20 | (2-(3,4-dimethoxyphenyl)ethoxy) | 4-[2-(3,4-dimethoxyphenyl)ethoxy]-3'-methyl-5'-{[4-(trifluoromethyl)pyrimidin-2-yl]amino}biphenyl-3-carboxylic acid | 554 | 554 | Ammonium Salt |
| 3.21 | (pyridin-2-ylmethoxy) | 3'-methyl-4-(pyridin-2-ylmethoxy)-5'-{[4-(trifluoromethyl)pyrimidin-2-yl]amino}biphenyl-3-carboxylic acid | 481 | 481 | Ammonium Salt |

TABLE 3.1-continued

| Ex. No. | R$^{cyl}$ | Name | [M + H]+ Calc'd | [M + H]+ Obsv'd | Form(s) |
|---|---|---|---|---|---|
| 3.22 | (pyridin-3-ylmethoxy) | 3'-methyl-4-(pyridin-3-ylmethoxy)-5'-{[4-(trifluoromethyl)pyrimidin-2-yl]amino}biphenyl-3-carboxylic acid | 481 | 481 | Ammonium Salt |
| 3.23 | (pyridin-4-ylmethoxy) | 3'-methyl-4-(pyridin-4-ylmethoxy)-5'-{[4-(trifluoromethyl)pyrimidin-2-yl]amino}biphenyl-3-carboxylic acid | 481 | 481 | Ammonium Salt |
| 3.24 | (2-methoxybenzyl)oxy | 4-[(2-methoxybenzyl)oxy]-3'-methyl-5'-{[4-(trifluoromethyl)pyrimidin-2-yl]amino}biphenyl-3-carboxylic acid | 510 | 510 | Ammonium Salt |
| 3.25 | (3-methoxybenzyl)oxy | 4-[(3-methoxybenzyl)oxy]-3'-methyl-5'-{[4-(trifluoromethyl)pyrimidin-2-yl]amino}biphenyl-3-carboxylic acid | 510 | 510 | Ammonium Salt |
| 3.26 | 2-(dimethylamino)ethoxy | 4-[2-(dimethylamino)ethoxy]-3'-methyl-5'-{[4-(trifluoromethyl)pyrimidin-2-yl]amino}biphenyl-3-carboxylic acid | 461 | 461 | Ammonium Salt |
| 3.27 | 3-(dimethylamino)propoxy | 4-[3-(dimethylamino)propoxy]-3'-methyl-5'-{[4-(trifluoromethyl)pyrimidin-2-yl]amino}biphenyl-3-carboxylic acid | 475 | 475 | Ammonium Salt |

TABLE 3.1-continued

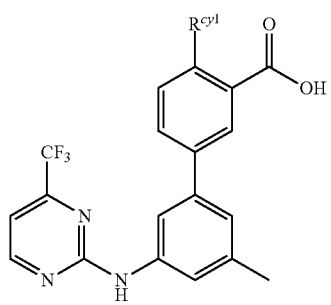

| Ex. No. | R$^{cyl}$ | Name | [M + H]+ Calc'd | [M + H]+ Obsv'd | Form(s) |
|---|---|---|---|---|---|
| 3.28 | (dimethylaminopropoxy group, racemic) | 4-[2-(dimethylamino)-1-methylethoxy]-3'-methyl-5'-{[4-(trifluoromethyl)pyrimidin-2-yl]amino}biphenyl-3-carboxylic acid | 475 | 475 | Ammonium Salt |
| 3.29 | (morpholinoethoxy group) | 3'-methyl-4-(2-morpholin-4-ylethoxy)-5'-{[4-(trifluoromethyl)pyrimidin-2-yl]amino}biphenyl-3-carboxylic acid | 503 | 503 | Ammonium Salt |
| 3.30 | (pyrrolidinylethoxy group) | 3'-methyl-4-(2-pyrrolidin-1-ylethoxy)-5'-{[4-(trifluoromethyl)pyrimidin-2-yl]amino}biphenyl-3-carboxylic acid | 487 | 487 | Ammonium Salt |
| 3.31 | (4-methylpiperazinylethoxy group) | 3'-methyl-4-[2-(4-methylpiperazin-1-yl)ethoxy]-5'-{[4-(trifluoromethyl)pyrimidin-2-yl]amino}biphenyl-3-carboxylic acid | 516 | 516 | Ammonium Salt |
| 3.32 | (1-methylpiperidin-4-ylmethoxy group) | 3'-methyl-4-[(1-methylpiperidin-4-yl)methoxy]-5'-{[4-(trifluoromethyl)pyrimidin-2-yl]amino}biphenyl-3-carboxylic acid | 501 | 501 | Ammonium Salt |
| 3.33 | (2-(2-hydroxyethoxy)ethoxy group) | 4-[2-(2-hydroxyethoxy)ethoxy]-3'-methyl-5'-{[4-(trifluoromethyl)pyrimidin-2-yl]amino}biphenyl-3-carboxylic acid | 478 | 478 | Formate Salt |

TABLE 3.1-continued

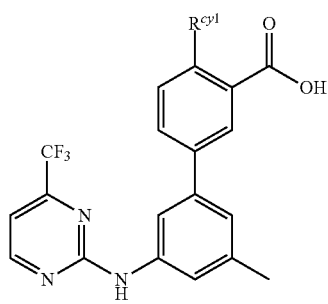

| Ex. No. | $R^{cyl}$ | Name | [M + H]+ Calc'd | [M + H]+ Obsv'd | Form(s) |
|---|---|---|---|---|---|
| 3.34 | HO~~~O~ | 4-(3-hydroxypropoxy)-3'-methyl-5'-{[4-(trifluoromethyl)pyrimidin-2-yl]amino}biphenyl-3-carboxylic acid | 448 | 448 | Formate Salt |
| 3.35 | HO~~~~O~ | 4-(4-hydroxybutoxy)-3'-methyl-5'-{[4-(trifluoromethyl)pyrimidin-2-yl]amino}biphenyl-3-carboxylic acid | 462 | 462 | Formate Salt |
| 3.36 | AcNH-CH2CH2-O~ | 4-[2-(acetylamino)ethoxy]-3'-methyl-5'-{[4-(trifluoromethyl)pyrimidin-2-yl]amino}biphenyl-3-carboxylic acid | 475 | 475 | Formate Salt |
| 3.37 | 1-methylimidazol-5-yl-CH2-O~ | 3'-methyl-4-[(1-methyl-1H-imidazol-5-yl)methoxy]-5'-{[4-(trifluoromethyl)pyrimidin-2-yl]amino}biphenyl-3-carboxylic acid | 484 | 484 | Formate Salt |
| 3.38 | 1-methylimidazol-4-yl-CH2-O~ | 3'-methyl-4-[(1-methyl-1H-imidazol-4-yl)methoxy]-5'-{[4-(trifluoromethyl)pyrimidin-2-yl]amino}biphenyl-3-carboxylic acid | 484 | 484 | Formate Salt |

TABLE 3.1-continued

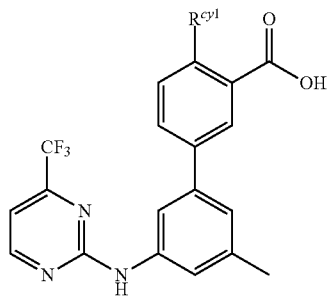

| Ex. No. | R<sup>cyl</sup> | Name | [M + H]+ Calc'd | [M + H]+ Obsv'd | Form(s) |
|---|---|---|---|---|---|
| 3.39 | (2-pyridyl-CH(CH₃)-O-, racemic) | 3'-methyl-4-(1-pyridin-2-ylethoxy)-5'-{[4-(trifluoromethyl)pyrimidin-2-yl]amino}biphenyl-3-carboxylic acid | 495 | 495 | Formate Salt |
| 3.40 | (CH₃C(O)NH-CH₂CH₂CH₂-O-) | 4-[3-(acetylamino)propoxy]-3'-methyl-5'-{[4-(trifluoromethyl)pyrimidin-2-yl]amino}biphenyl-3-carboxylic acid | 489 | 489 | Formate Salt |
| 3.41 | (1-methyl-1H-1,2,4-triazol-5-yl-CH₂-O-) | 3'-methyl-4-[(1-methyl-1H-1,2,4-triazol-5-yl)methoxy]-5'-{[4-(trifluoromethyl)pyrimidin-2-yl]amino}biphenyl-3-carboxylic acid | 485 | 485 | Formate Salt |

Example 3.42

N-(3'-methyl-5'-{[4-(trifluoromethyl)pyrimidin-2-yl]amino}biphenyl-3-yl)methanesulfonamide

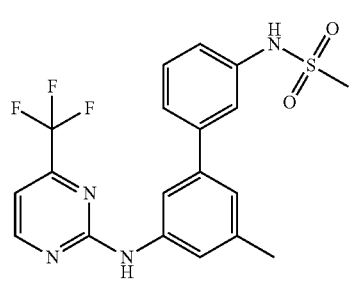

3.42

Methanesulfonyl chloride (0.017 g, 0.150 mmol) and triethylamine (0.028 ml, 0.200 mmol) were added to a solution of 5-methyl-$N^3$-[4-(trifluoromethyl)pyrimidin-2-yl]biphenyl-3,3'-diamine (0.034 g, 0.100 mmol) in DCM (1.00 ml) and stirred for 14 hours at room temperature. The reaction mixture was concentrated under reduced pressure and the residue was dissolved in DMSO (1 mL), then purified by mass triggered reverse phase HPLC to give N-(3'-methyl-5'-{[4-(trifluoromethyl)pyrimidin-2-yl]amino}biphenyl-3-yl)methanesulfonamide. MS ESI calcd. for $C_{19}H_{18}F_3N_4O_2S$ [M+H]⁺ 423, found 423. ¹H NMR (600 MHz, DMSO-d₆) δ 10.21 (s, 1H), 8.78 (d, J=4.9 Hz, 1H), 7.83 (s, 1H), 7.52 (s, 1H), 7.40 (dt, J=15.7, 4.8 Hz, 2H), 7.30 (d, J=7.7 Hz, 1H), 7.23 (d, J=4.9 Hz, 1H), 7.17 (dd, J=8.0, 1.3 Hz, 1H), 7.04 (s, 1H), 2.99 (s, 3H), 2.32 (s, 3H).

The following examples in Table 3.2 were prepared in an analogous manner of that described for Example 3.42.

TABLE 3.2

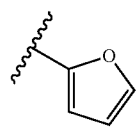 [SMILES: *c1ccco1]

| Ex. No. | R<sup>cyA</sup> | Name | [M + H]+ Calc'd | [M + H]+ Obsv'd | Form(s) |
|---|---|---|---|---|---|
| 3.43 | —CH$_2$CH$_3$ | N-(3'-methyl-5'{[4-(trifluoromethyl)pyrimidin-2-yl]amino}biphenyl-3-yl)ethanesulfonamide | 437 | 437 | Formate Salt |
| 3.44 | —C(H)(CH$_3$)$_2$ | N-(3'-methyl-5'-{[4-(trifluoromethyl)pyrimidin-2-yl]amino}biphenyl-3-yl)propane-2-sulfonamide | 451 | 451 | Formate Salt |
| 3.45 | 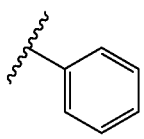 [SMILES: *c1ccccc1] | N-(3'-methyl-5'-{[4-(trifluoromethyl)pyrimidin-2-yl]amino}biphenyl-3-yl)furan-2-sulfonamide | 475 | 475 | Formate Salt |
| 3.46 | 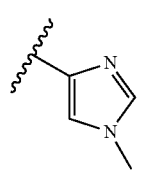 [SMILES: *c1cn(C)cn1] | N-(3'-methyl-5'-{[4-(trifluoromethyl)pyrimidin-2-yl]amino}biphenyl-3-yl)benzenesulfonamide | 485 | 485 | Formate Salt |
| 3.47 | 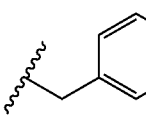 | 1-methyl-N-(3'-methyl-5'-{[4-(trifluoromethyl)pyrimidin-2-yl]amino}biphenyl-3-yl)-1H-imidazole-4-sulfonamide | 489 | 489 | Formate Salt |
| 3.48 | 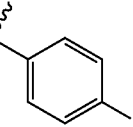 | N-(3'-methyl-5'-{[4-(trifluoromethyl)pyrimidin-2-yl]amino}biphenyl-3-yl)-1-phenylmethanesulfonamide | 499 | 499 | Formate Salt |
| 3.49 | 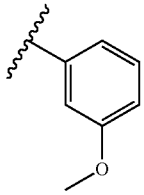 | 4-methoxy-N-(3'-methyl-5'-{[4-(trifluoromethyl)pyrimidin-2-yl]amino}biphenyl-3-yl)benzenesulfonamide | 515 | 515 | Formate Salt |
| 3.50 | 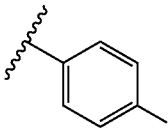 | 3-methoxy-N-(3'-methyl-5'-1[4-(trifluoromethyl)pyrimidin-2-yl]amino}biphenyl-3-yl)benzenesulfonamide | 515 | 515 | Formate Salt |
| 3.51 | | 4-chloro-N-(3'-methyl-5'-{[4-(trifluoromethyl)pyrimidin-2-yl]amino}biphenyl-3-yl)benzenesulfonamide | 519 | 519 | Formate Salt |

TABLE 3.2-continued

| Ex. No. | R<sup>CyA</sup> | Name | [M + H]+ Calc'd | [M + H]+ Obsv'd | Form(s) |
|---|---|---|---|---|---|
| 3.52 | 3-chlorophenyl | 3-chloro-N-(3'-methyl-5'-{[4-(trifluoromethyl)pyrimidin-2-yl]amino}biphenyl-3-yl)benzenesulfonamide | 519 | 519 | Formate Salt |
| 3.53 | 2-chlorophenyl | 2-chloro-N-(3'-methyl-5'-{[4-(trifluoromethyl)pyrimidin-2-yl]amino}biphenyl-3-yl)benzenesulfonamide | 519 | 519 | Formate Salt |
| 3.54 | naphthalen-2-yl | N-(3'-methyl-5'-{[4-(trifluoromethyl)pyrimidin-2-yl]amino}biphenyl-3-yl)naphthalene-2-sulfonamide | 535 | 535 | Formate Salt |
| 3.55 | naphthalen-1-yl | N-(3'-methyl-5'-{[4-(trifluoromethyl)pyrimidin-2-yl]amino}biphenyl-3-yl)naphthalene-1-sulfonamide | 535 | 535 | Formate Salt |
| 3.56 | benzothiophen-2-yl | N-(3'-methyl-5'-{[4-(trifluoromethyl)pyrimidin-2-yl]amino}biphenyl-3-yl)-1-benzothiophene-2-sulfonamide | 541 | 541 | Formate Salt |
| 3.57 | 3,4-dimethoxyphenyl | 3,4-dimethoxy-N-(3'-methyl-5'-{[4-(trifluoromethyl)pyrimidin-2-yl]amino}biphenyl-3-yl)benzenesulfonamide | 545 | 545 | Formate Salt |

TABLE 3.2-continued

| Ex. No. | R^cyA | Name | [M + H]+ Calc'd | [M + H]+ Obsv'd | Form(s) |
|---|---|---|---|---|---|
| 3.58 | | N-(3'-methyl-5'-{[4-(trifluoromethyl)pyrimidin-2-yl]amino}biphenyl-3-yl)-4-(trifluoromethyl)benzenesulfonamide | 553 | 553 | Formate Salt |
| 3.59 | | 5-(dimethylamino)-N-(3'-methyl-5'-{[4-(trifluoromethyl)pyrimidin-2-yl]amino}biphenyl-3-yl)naphthalene-1-sulfonamide | 578 | 578 | Formate Salt |

Example 4

Preparation of Compounds of Formula (I) Using the General Methods Illustrated in Scheme 4

Example 4.1

Methyl-5'-(4-(trifluoromethyl)pyrimidin-2-ylamino)biphenyl-3-sulfonic acid

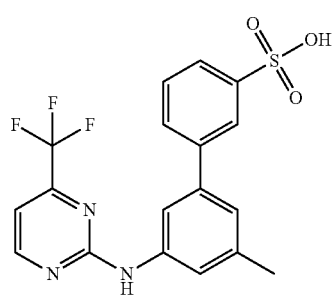

Sodium hydroxide (1M in water, 1 mL, 1.0 mmol) was added to a solution of 3-bromosulfonyl chloride (0.148 g, 0.580 mmol) in dioxane (2.64 mL) at room temperature. The reaction mixture was heated at 80° C. for 2 hours and then cooled to room temperature. N-(3-methyl-5-(4,4,5,5-tetramethyl-1,3,2-dioxaborolan-2-yl)phenyl)-4-(trifluoromethyl)pyrimidin-2-amine (0.20 g, 0.527 mmol), sodium carbonate (0.527 mL, 1.055 mmol) and PdCl$_2$(dppf)-CH$_2$Cl$_2$ adduct (0.022 g, 0.026 mmol) were added to the reaction mixture and heated to 80° C. for 14 hours. Upon cooling to room temperature, the reaction mixture was diluted with ethyl acetate (50 mL) and then acidified with hydrochloric acid (1N in water). The aqueous layer was separated and extracted with ethyl acetate (50 mL). The combined organic layers were dried, filtered, and concentrated in vacuo. The residue was purified by silica gel flash column chromatography (methanol/ethyl acetate). The fractions were combined and concentrated under reduced pressure. The residue was triturated with ether to give a brown solid, which was filtered and dried in vacuo. The residue was purified by reverse phase HPLC to give 3'-methyl-5'-(4-(trifluoromethyl)pyrimidin-2-ylamino)biphenyl-3-sulfonic acid as a white solid. MS ESI calcd. for C$_{18}$H$_{15}$F$_3$N$_3$O$_3$S [M+H]$^+$ 410, found 410. $^1$H NMR (600 MHz, CD$_3$OD) δ 11.05 (s, 1H), 9.63 (s, 1H), 8.65, (m, 2H), 8.42-8.34 (m, 3H), 8.23 (m, 1H), 8.06 (m, 1H), 7.91 (s, 1H), 7.65 (br.s, 1H), 3.17 (s, 3H).

Example 4.2

N,3'-Dimethyl-5'-((4-(trifluoromethyl)pyrimidin-2-yl)amino)-[1,1'-biphenyl]-3-sulfonamide

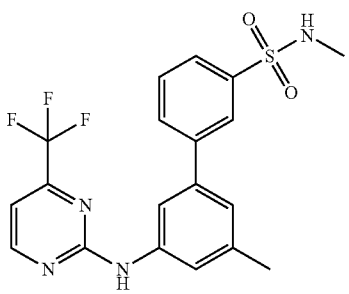

Methylamine (40% aq., 0.5 mL, 1.00 mmol) was added to a solution of 3-bromosulfonyl chloride (0.148 g, 0.580 mmol) in dioxane (2.64 mL) at room temperature and the reaction mixture was heated to 80° C. for 2 hours. Upon cooling to room temperature, N-(3-methyl-5-(4,4,5,5-tetramethyl-1,3,2-dioxaborolan-2-yl)phenyl)-4-(trifluoromethyl)pyrimidin-2-amine (30 mg, 0.079 mmol), PdCl$_2$(dppf) (0.022 g, 0.026 mmol) and sodium carbonate (2M in water, 0.527 mL, 1.055 mmol) were added to the reaction mixture, then heated to 80° C. for 14 hours. The reaction mixture was allowed to cool to room temperature, acidified with saturated aqueous ammonium chloride (1 mL) and diluted with ethyl acetate (2 mL). The mixture was stirred at room temperature for 3 hours. The aqueous layer was removed and Silicycle PTP resin (300 mg) was added to the organic layer. The suspension was stirred at room temperature for 3 hours and then filtered to give a clear solution which was evaporated in vacuo. The residue was dissolved in dimethyl sulfoxide (1 mL) and purified by reverse phase HPLC purification to give N,3'-dimethyl-5'-((4-(trifluoromethyl)pyrimidin-2-yl)amino)-[1,1'-biphenyl]-3-sulfonamide as a white solid. MS ESI calcd. for C$_{19}$H$_{18}$F$_3$N$_4$O$_2$S [M+H]$^+$ 423, found 423. $^1$H NMR (500 MHz, MeOH-d$^4$) δ 11.09 (s, 1H), 9.63 (d, J=4.9 Hz, 1H), 8.79 (m, 2H), 8.69 (m, 1H), 8.54 (m, 2H), 8.42 (s, 1H), 8.31 (m, 1H), 8.08 (d, J=4.9 Hz, 1H), 7.99 (s, 1H), 4.11 (s, 3H), 2.87 (s, 3H).

The following examples in Table 4 were prepared in an analogous manner to that described for Example 4.2.

TABLE 4

| Ex. No. | R$^{cyB}$ | Name | [M + H]+ Calc'd | [M + H]+ Obsv'd | Form(s) |
|---|---|---|---|---|---|
| 4.3 | (NH-CH$_2$CH$_2$CH$_2$-COOH) | 4-{[(3'-methyl-5'-{[4-(trifluoromethyl)pyrimidin-2-yl]amino}biphenyl-3-yl)sulfonyl]amino}butanoic acid | 495 | 495 | Free Base |
| 4.4 | (NH-CH$_2$CH$_2$-COOH) | N-[(3'-methyl-5'-{[4-(trifluoromethyl)pyrimidin-2-yl]amino}biphenyl-3-yl)sulfonyl]-beta-alanine | 481 | 481 | Free Base |
| 4.5 | (D-proline N-attached) | 1-[(3'-methyl-5'-{[4-(trifluoromethyl)pyrimidin-2-yl]amino}biphenyl-3-yl)sulfonyl]-D-proline | 507 | 507 | Free Base |
| 4.6 | (NH-CH$_2$-C$_6$H$_4$-COOH) | 4-({[(3'-methyl-5'-{[4-(trifluoromethyl)pyrimidin-2-yl]amino}biphenyl-3-yl)sulfonyl]amino}methyl)benzoic acid | 543 | 543 | Free Base |
| 4.7 | (NH-C$_6$H$_4$-COOH) | 3-{[(3'-methyl-5'-{[4-(trifluoromethyl)pyrimidin-2-yl]amino}biphenyl-3-yl)sulfonyl]amino}benzoic acid | 529 | 529 | Free Base |

TABLE 4-continued

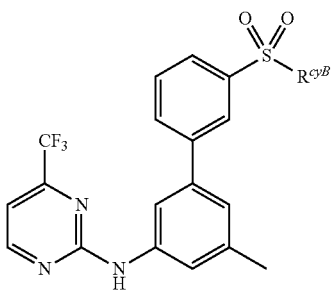

| Ex. No. | R<sup>cyB</sup> | Name | [M + H]+ Calc'd | [M + H]+ Obsv'd | Form(s) |
|---|---|---|---|---|---|
| 4.8 | *NH-C6H4-COOH* | 4-{[(3'-methyl-5'-{[4-(trifluoromethyl)pyrimidin-2-yl]amino}biphenyl-3-yl)sulfonyl]amino}benzoic acid | 529 | 529 | Free Base |
| 4.9 | *NH-CH2CH2-pyrrolidine* | 3'-methyl-N-(2-pyrrolidin-1-ylethyl)-5'-{[4-(trifluoromethyl)pyrimidin-2-yl]amino}biphenyl-3-sulfonamide | 506 | 506 | Free Base |
| 4.10 | *N-piperidin-4-ol* | 1-[(3'-methyl-5'-{[4-(trifluoromethyl)pyrimidin-2-yl]amino}biphenyl-3-yl)sulfonyl]piperidin-4-ol | 493 | 493 | Free Base |
| 4.11 | *NH-CH2CH2-OMe* | N-(2-methoxyethyl)-3'-methyl-5'-{[4-(trifluoromethyl)pyrimidin-2-yl]amino}biphenyl-3-sulfonamide | 467 | 467 | Free Base |
| 4.12 | *NH-CH2-pyridin-2-yl* | 3'-methyl-N-(pyridin-2-ylmethyl)-5'-{[4-(trifluoromethyl)pyrimidin-2-yl]amino}biphenyl-3-sulfonamide | 500 | 500 | Free Base |
| 4.13 | *NH-pyridin-3-yl* | 3'-methyl-N-pyridin-3-yl-5'-{[4-(trifluoromethyl)pyrimidin-2-yl]amino}biphenyl-3-sulfonamide | 486 | 486 | Free Base |

Example 5

Compounds of Formula (I) using the General Methods Illustrated in Scheme 5

The description provided in Example 5 is a prophetic example.

Procedure A

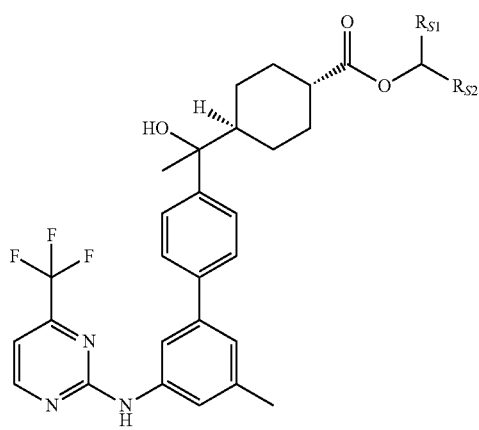

This general procedure describes the procedure for conversion of (A1) to (A) as shown in Scheme 5. To a mixture of compound of formula (A1) (1 mmol), 1° or 2° alcohol (5 mmol), and triphenylphosphine (resin-bound, 1.6 mmol/g loading, 2 mmol) in tetrahydrofuran is added di-tert-butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3×). The filtrate is concentrated under reduced pressure to afford the crude residue TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by silica gel chromatography to afford the product residue. The residue is lyophilized from acetonitrile and water to afford a compound of structural subtype (A).

The following compounds in Table 5.1 could be prepared according to procedures which are analogous to those described in Example 5, Procedure A.

TABLE 5.1

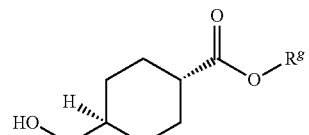

| Ex. No. | $R^g$ |
|---|---|
| 5.1 | 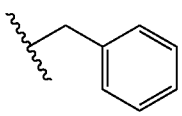 [SMILES: *Cc1ccccc1] |
| 5.2 |  |
| 5.3 | 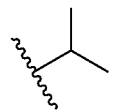 [SMILES: *C(C)C] |
| 5.4 | 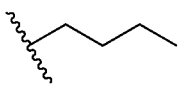 [SMILES: *CCCC] |
| 5.5 | 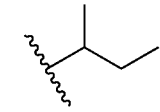 |
| 5.6 | 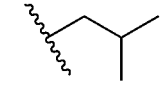 |
| 5.7 | 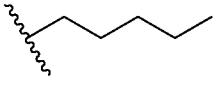 [SMILES: *CCCCC] |
| 5.8 | 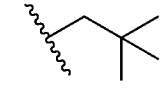 [SMILES: *CC(C)(C)C] |
| 5.9 | 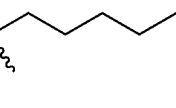 |
| 5.10 | 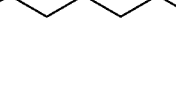 |

TABLE 5.1-continued

[Structure: cyclohexane carboxylate ester with Rg group, connected to biphenyl-pyrimidine-aniline scaffold bearing CF3 and methyl groups, with HO and H stereochemistry indicators]

| Ex. No. | Rg |
|---|---|
| 5.12 | cyclohexyl |
| 5.13 | tetrahydropyran-4-yl |
| 5.14 | cyclohexylmethyl |
| 5.15 | -CH2CH2OCH3 |
| 5.16 | -CH2CH2OCH2CH2OCH2CH3 |
| 5.17 | -CH2C(O)OCH3 |
| 5.18 | -CH2C(O)N(CH3)2 |
| 5.19 | -CH2CH2CH2-morpholinyl |
| 5.20 | -CH2CH2N(CH3)2 |
| 5.21 | (4-methyl-2-oxo-1,3-dioxol-5-yl)methyl |

Procedure B

[Structure: same scaffold with ester linkage –C(O)O–CH(R_{S5})–O–C(O)–O–R_{S6}]

This general procedure describes the procedure for conversion of (A1) to (C) as shown in Scheme 5. A mixture of compound of formula (A1) (1.0 mmol), potassium carbonate (2.0 mmol), and sodium iodide (0.50 mmol) in DMF is stirred at 20° C. After 30 minutes, alkyl halide of formula (C1) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography (ethyl acetate/hexanes, linear gradient) to afford the product residue. The residue is lyophilized from acetonitrile and water to afford a compound of formula (C).

The following compounds in Table 5.2 could be prepared according to procedures which are analogous to those described in Example 5, Procedure B.

TABLE 5.2

| Ex. No. | R$^g$ |
|---|---|
| 5.22 | (isopropyl ethyl carbonate group) |
| 5.23 | (ethyl isopropyl carbonate group) |
| 5.24 | (isopropyl isopropyl carbonate group) |
| 5.25 | (cyclohexyl isopropyl carbonate group) |

Procedure C

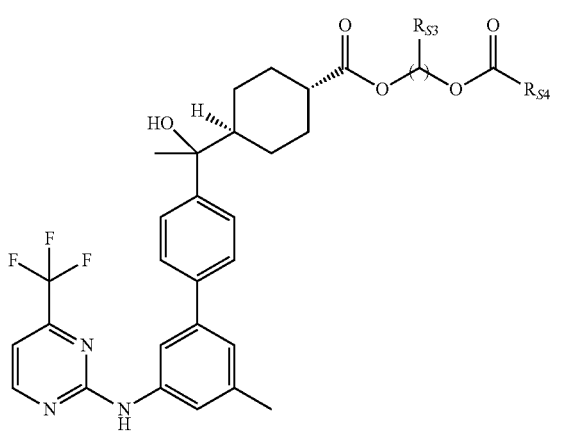

(n) = 1, 2

This general procedure describes the procedure for conversion of (A1) to (B) as shown in Scheme X. To a solution of compound of formula (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by silica gel chromatography (ethyl acetate/hexanes, linear gradient) to afford the product residue. The residue is lyophilized from acetonitrile and water to afford a compound of formula (B).

The following compounds in Table 5.3 could be prepared according to procedures which were analogous to those described in Example 5, Procedure C.

TABLE 5.3

| Ex. No. | R$^g$ |
|---|---|
| 5.26 | (ethyl pivalate group) |
| 5.27 | (isopropyl acetate group) |
| 5.28 | (isopropyl isobutyrate group) |
| 5.29 | (ethyl acetate group) |

Example 6

Compounds of Formula (I) Using the General Methods Illustrated in Scheme 6

The description provided in Example 6 is a prophetic example.

Example 6.1

Methyl trans-4-(1R or 1S)-1-hydroxy-1-[(3'-methyl-5'-{[4-(trifluoromethyl)pyrimidin-2-yl]amino}[1,1'-biphenyl]-4-yl]ethyl)cyclohexanecarboxylate

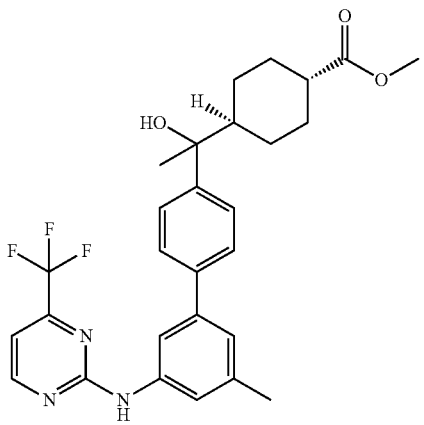

6.1

This general procedure describes the procedure for conversion of (A1) to (D) as shown in Scheme 6. To a suspension of compound of formula (A1) (1.0 mmol) in 1:1 methanol:dichloromethane is added trimethylsilyldiazomethane (2.0 M in diethyl ether, 1.0 mmol) at 0° C. The reaction mixture is stirred at 0° C. until all gas evolution ceases. The reaction mixture is allowed to warm to ambient temperature and quenched by the addition of several drops of acetic acid. The reaction mixture is concentrated under reduced pressure and the residue is purified by silica gel chromatography (ethyl acetate/hexanes, linear gradient) to afford the product residue. The residue is lyophilized from acetonitrile and water to afford methyl trans-4-(1R or 1S)-1-hydroxy-1-[(3'-methyl-5'-{[4-(trifluoromethyl)pyrimidin-2-yl]amino}[1,1'-biphenyl]-4-yl]ethyl)cyclohexanecarboxylate.

Example 7

Preparation of Hydroxyalkyl Esters

The description provided in Example 7 is a prophetic example.

Example 7.1

2-Hydroxyethyl trans-4-(1R or 1S)-1-hydroxy-1-[(3'-methyl-5'-{[4-(trifluoromethyl)pyrimidin-2-yl]amino}[1,1'-biphenyl]-4-yl]ethyl)cyclohexanecarboxylate

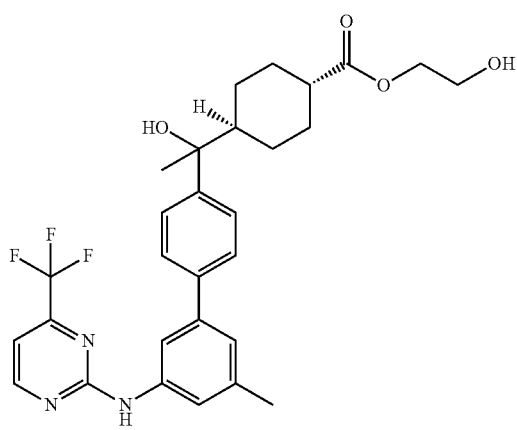

7.1

A mixture of compounds of formula (A1) (1.0 mmol), potassium carbonate (6.0 mmol) and sodium iodide (1.0 mmol) in DMF is stirred for 10 minutes at ambient temperature. To this mixture is added 2-chloroethanol (4.0 mmol) and the reaction mixture is heated at 60° C. for 16 hours. After 16 hours, additional 2-chloroethanol (1.0 mmol) is added and the reaction mixture is heated to 65° C. for an additional 2 hours. The reaction mixture is then diluted with ethyl acetate and washed sequentially with water (3×), aqueous sodium carbonate solution (2×), additional water (3×), and brine (2×). The organic layer is dried over magnesium sulfate, filtered, and concentrated under reduced pressure to afford the crude product residue. The residue is purified by silica gel chromatography ([3% (1.0 M ammonia in dioxane) in ethyl acetate]/[3% (1.0M ammonia in dioxane) in dichloromethane], linear gradient) to afford 2-hydroxyethyl trans-4-(1R or 1S)-1-hydroxy-1-[(3'-methyl-5'-{[4-(trifluoromethyl)pyrimidin-2-yl]amino}[1,1'-biphenyl]-4-yl]ethyl)cyclohexanecarboxylate.

Hydrolysis Assay: Analysis of Hydrolysis of Prodrug to Parent Species

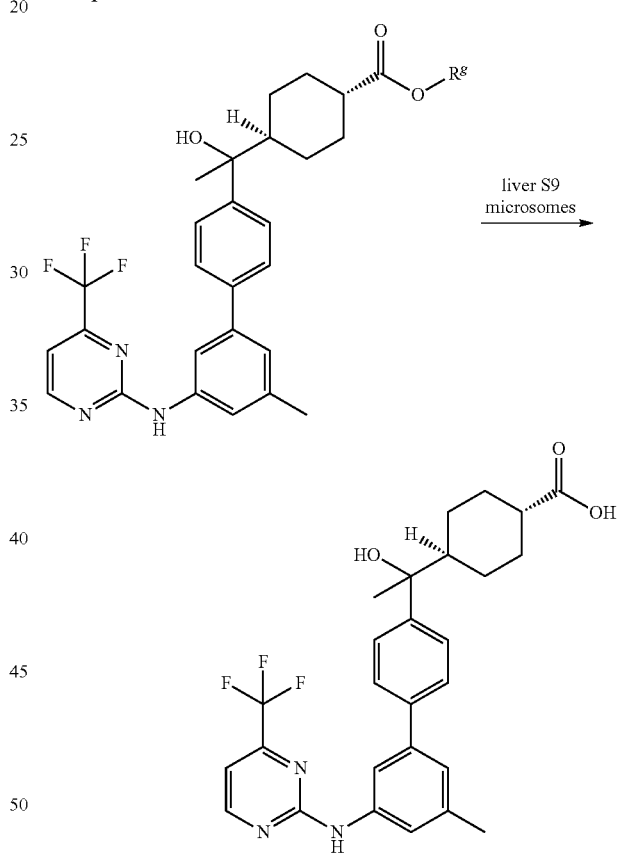

The stability of prodrugs is investigated in human liver S9 microsomes. Incubations of prodrugs (10 μM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treat with 4 volumes of acetonitrile containing 2% formic acid and an internal standard, and centrifuge. The supernatants are analyzed by LC-MS/MS for prodrug disappearance and appearance of active drug. The half-life of the prodrug is calculated from the % prodrug remaining at different time points calculated from on the peak area ratio relative to t=0. The amount of active drug generated at the different time points is determined using a standard curve.

Biological Assay
Homogeneous Time-Resolved Fluorescence (HTRF) Assay for the Recombinant Human Syk Enzyme A recombinant GST-hSYK fusion protein was used to measure potency of compounds to inhibit human Syk activity. The recombinant human GST-SYK (Carna Biosciences #08-176) (5 μM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 μM final concentration). Final volume of the reaction was 10 μL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 μL. The resulting HTRF signal was measured after 30 minutes on an EnVision (Perkin-Elmer) reader using a time-resolved fluorescence protocol. Table A below lists activities as $IC_{50}$ values (nM) for representative compounds of the invention.

TABLE A

| Ex. No. | $IC_{50}$ (nM) |
| --- | --- |
| 1.1 | 12.6 |
| 1.2 | 18.9 |
| 1.3 | 1877 |
| 1.4 | 1536 |
| 1.5 | 76.7 |
| 1.6 | 231.7 |
| 1.7 | 293.3 |
| 1.8 | 78.7 |
| 1.9 | 131.7 |
| 1.10 | 846.2 |
| 1.11 | 1879 |
| 1.12 | 333.7 |
| 1.13 | 433.5 |
| 1.14 | 424.1 |
| 1.15 | 242.0 |
| 1.16 | 58.1 |
| 1.17 | 814.5 |
| 1.18 | 251.1 |
| 1.19 | 79.8 |
| 1.20 | 67.4 |
| 1.21 | 255.8 |
| 1.22 | 367.7 |
| 1.23 | 147.5 |
| 1.24 | 33.2 |
| 1.25 | 1694 |
| 1.26 | 46.9 |
| 1.27 | 3.3 |
| 1.28 | 171.9 |
| 1.29 | 1750 |
| 1.30 | 79.3 |
| 1.31 | 260.0 |
| 1.32 | 36.8 |
| 1.33 | 219.7 |
| 1.34 | 42.9 |
| 1.35 | 102.3 |
| 1.36 | 172.7 |
| 1.37 | 2101 |
| 1.38 | 313.5 |
| 1.39 | 256.9 |
| 1.40 | 3342 |
| 1.41 | 681.0 |
| 1.42 | 589.6 |
| 1.43 | 1952 |
| 1.44 | 547.1 |
| 1.45 | 268.3 |
| 1.46 | 201.3 |
| 1.47 | 268.8 |
| 1.48 | 357.3 |
| 1.49 | 369.7 |
| 1.50 | 352.6 |
| 1.51 | 1456 |
| 1.52 | 155.7 |
| 1.53 | 594.8 |
| 1.54 | 363.1 |
| 1.55 | 218.2 |
| 1.56 | 40.7 |
| 1.57 | 2490 |
| 1.58 | 2121 |
| 1.59 | 1811 |
| 1.60 | 178.4 |
| 1.61 | 2563 |
| 1.62 | 627.7 |
| 1.63 | 528.3 |
| 1.64 | 176.4 |
| 1.65 | 279.9 |
| 1.66 | 645.1 |
| 1.67 | 222.8 |
| 1.68 | 87.0 |
| 1.69 | 276.3 |
| 1.70 | 189.5 |
| 1.71 | 162.0 |
| 1.72 | 69.1 |
| 1.73 | 280.2 |
| 1.74 | 97.1 |
| 1.75 | 21.6 |
| 1.76 | 65.4 |
| 1.77 | 128.7 |
| 1.78 | 1.9 |
| 1.79 | 4.6 |
| 1.80 | 1.3 |
| 1.81 | 6726 |
| 1.82 | 27.0 |
| 1.83 | 7.6 |
| 1.84 | 7.1 |
| 1.85 | 35.0 |
| 1.86 | 90.7 |
| 1.87 | 225.1 |
| 1.88 | 5.9 |
| 1.89 | 181.6 |
| 1.90 | 533.1 |
| 1.91 | 478.9 |
| 1.92 | 560.0 |
| 1.93 | 484.6 |
| 1.94 | 861.2 |
| 1.95 | 2550 |
| 1.96 | 2.7 |
| 1.97 | 177.5 |
| 1.98 | 2.8 |
| 1.99 | 5.6 |
| 1.100 | 18.4 |
| 1.101 | 11.3 |
| 1.102 | 4.8 |
| 1.103 | 3.2 |
| 1.104 | 27.1 |
| 1.105 | 879.3 |
| 1.106 | 1113 |
| 1.107 | 1600 |
| 1.108 | 1694 |
| 1.109 | 2640 |
| 1.110 | 3381 |
| 1.111 | 5609 |
| 1.112 | 6.6 |
| 1.113 | 500.8 |
| 1.114 | 8.0 |
| 1.115 | 10.8 |
| 1.116 | 25.6 |
| 1.117 | 1422 |
| 1.118 | 685.2 |
| 1.119 | 6.5 |
| 1.120 | 4.2 |
| 1.121 | 544.7 |
| 1.122 | 846.6 |

TABLE A-continued

| Ex. No. | IC$_{50}$ (nM) |
|---|---|
| 1.123 | 477.4 |
| 1.124 | 8.5 |
| 1.125 | 72.2 |
| 1.126 | 37.4 |
| 1.127 | 288.3 |
| 1.128 | 919.9 |
| 1.129 | 482.9 |
| 1.130 | 52.7 |
| 1.131 | 610.0 |
| 1.132 | 837.0 |
| 1.133 | 375.7 |
| 1.134 | 609.6 |
| 1.135 | 212.1 |
| 1.136 | 119.6 |
| 1.137 | 5306 |
| 1.138 | 99.5 |
| 1.139 | 238.2 |
| 1.140 | 6.4 |
| 1.141 | 6.2 |
| 1.142 | 16.0 |
| 1.143 | 15.8 |
| 1.144 | 342.0 |
| 1.145 | 257.5 |
| 1.146 | 911.3 |
| 2.1 | 20.9 |
| 2.2 | 43.7 |
| 2.3 | 6.3 |
| 2.4 | 147.0 |
| 2.5 | 661.9 |
| 2.6 | 45.5 |
| 2.7 | 14.0 |
| 2.8 | 9.9 |
| 2.9 | 722.4 |
| 2.10 | 72.1 |
| 3.1 | 11.2 |
| 3.2 | 18.7 |
| 3.3 | 18.3 |
| 3.4 | 6.9 |
| 3.5 | 21.0 |
| 3.6 | 11.4 |
| 3.7 | 13.7 |
| 3.8 | 11.5 |
| 3.9 | 45.5 |
| 3.10 | 31.8 |
| 3.11 | 10.8 |
| 3.12 | 108.1 |
| 3.13 | 235.8 |
| 3.14 | 78.1 |
| 3.15 | 27.1 |
| 3.16 | 15.0 |
| 3.17 | 27.2 |
| 3.18 | 24.6 |
| 3.19 | 27.7 |
| 3.20 | 25.0 |
| 3.21 | 14.3 |
| 3.22 | 9.1 |
| 3.23 | 16.3 |
| 3.24 | 21.3 |
| 3.25 | 17.4 |
| 3.26 | 83.9 |
| 3.27 | 64.5 |
| 3.28 | 123.4 |
| 3.29 | 35.7 |
| 3.30 | 175.6 |
| 3.31 | 23.2 |
| 3.32 | 455.3 |
| 3.33 | 21.5 |
| 3.34 | 10.6 |
| 3.35 | 10.4 |
| 3.36 | 31.5 |
| 3.37 | 9.7 |
| 3.38 | 5.6 |
| 3.39 | 21.3 |
| 3.40 | 17.4 |
| 3.41 | 41.9 |
| 3.42 | 103.0 |
| 3.43 | 175.2 |
| 3.44 | 347.7 |
| 3.45 | 237.8 |
| 3.46 | 1663 |
| 3.47 | 140.4 |
| 3.48 | 1252 |
| 3.49 | 2412 |
| 3.50 | 3545 |
| 3.51 | 3227 |
| 3.52 | 3773 |
| 3.53 | 2353 |
| 3.54 | 9926 |
| 3.55 | 5973 |
| 3.56 | 4394 |
| 3.57 | 2660 |
| 3.58 | 7172 |
| 3.59 | 9625 |
| 4.1 | 8.5 |
| 4.2 | 159.0 |
| 4.3 | 7.4 |
| 4.4 | 4.6 |
| 4.5 | 30.7 |
| 4.6 | 30.5 |
| 4.7 | 49.6 |
| 4.8 | 2.2 |
| 4.9 | 99.1 |
| 4.10 | 242.1 |
| 4.11 | 167.8 |
| 4.12 | 451.6 |
| 4.13 | 171.0 |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound of the Formula (I)

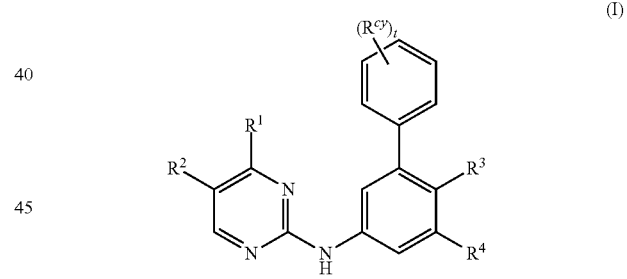

or a pharmaceutically acceptable salt thereof, wherein
$R^1$ is selected from the group consisting of $C_1$-$C_6$ alkyl, $C_1$-$C_3$ fluoroalkyl, $C_1$-$C_3$ alkoxy, $C_3$-$C_6$ cycloalkyl, 2,8-diazaspiro[4.5]decyl, and 4-piperidinyloxy;
$R^2$ is selected from the group consisting of H, methyl, methoxy, —$CHF_2$, —$CF_3$, halo, and cyano;
$R^3$ is selected from the group consisting of H, $C_1$-$C_3$ alkyl, and halo;
$R^4$ is selected from the group consisting of H, $C_1$-$C_3$ alkyl, $C_1$-$C_3$ fluoroalkyl, $C_1$-$C_3$ alkoxy, $C_3$-$C_6$ cycloalkyl, halo, —N($R^{4a}$)$_2$, —N($R^{4a}$)C(O)$R^{4b}$, —N($R^{4a}$)C(O)N($R^{4a}$)$_2$,
—N($R^{4a}$)S(O)$_2R^{4b}$, —N($R^{4a}$)C(O)N($R^{4a}$)—S(O)$_2R^{4a}$, —$CO_2$H, and $R^{4c}$,
wherein $R^{4c}$ is -G-$R^{4c1}$ or —$R^{4c1}$, wherein
G is a —O—, —C(O)—, or —$CH_2$—;
$R^{4c1}$ is:
(i) a 5-8 membered heterocyclyl containing 1 nitrogen atom and 0 to 1 additional heteroatoms selected from the group consisting of N, O, and S;

(ii) a 9-10 membered spiroheterocyclyl containing 1 nitrogen atom and 0 to 1 additional heteroatoms selected from the group consisting of N, O, and S; and (iii) phenyl;

wherein said $R^{4c1}$ is unsubstituted or substituted by 1 to 2 $R^{4c2}$ moieties selected from the group consisting of $C_1$-$C_3$ alkyl, —S(O)$_2$—($C_1$-$C_3$ alkyl), —CH$_2$—O—($C_1$-$C_3$ alkyl), —CH$_2$—N($C_1$-$C_3$ alkyl)$_2$, and —CH$_2$O—C(O)—($C_1$-$C_3$ alkyl), or optionally, wherein 2 $R^{c2}$ moieties are geminally substituted on a common ring carbon, the 2 $R^{4c2}$ moieties together with said ring carbon form a carbonyl;

each $R^{4a}$ is independently selected from the group consisting of H, $C_1$-$C_3$ alkyl, and $C_1$-$C_3$ fluoroalkyl;

$R^{4b}$ is selected from the group consisting of $C_1$-$C_3$ alkyl and phenyl, wherein said phenyl is unsubstituted or substituted by one halo;

t is 0, 1, 2, or 3;

each $R^{cy}$ is independently selected from the group consisting of:

A. a group of the formula

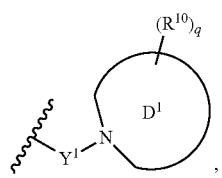

wherein $Y^1$ is a bond, —(CH$_2$)$_{z1}$—, —S(O)$_2$(CH$_2$)$_{z1}$—, —S(O)$_2$N(H)(CH$_2$)$_{z2}$—, —O(CH$_2$)$_{z2}$—, or —C(O)—;

the subscript z1 is 0, 1, 2, or 3;

the subscript z2 is 2 or 3;

$D^1$ is (i) a 4- to 9-membered mono- or bicyclic heterocyclic ring optionally containing one to two additional heteroatoms selected from the group consisting of N, O, S, S(O), and S(O)$_2$;

(ii) a 9- to 11-membered spiroheterocyclic ring containing one to two additional heteroatoms selected from the group consisting of N and O;

each $R^{10}$ is independently selected from the group consisting of $C_1$-$C_3$ alkyl, $C_1$-$C_3$ alkoxy, halo, hydroxyl, $C_1$-$C_3$ fluoroalkyl, —(CH$_2$)$_{n5}$CO$_2$R$^g$, hydroxyl($C_1$-$C_3$) alkyl, —(CH$_2$)$_{n5}$OCH$_3$, —C(O)—($C_1$-$C_3$) alkyl, —(CH$_2$)$_{n5}$C(O)N(R$^h$)$_2$, —S(O)$_2$—($C_1$-$C_3$) alkyl, —C(O)CH$_2$CN, and —C(O)CH$_2$OH, or wherein when two $R^{10}$ moieties are geminally substituted on a common ring carbon atom of $D^1$, the two geminally substituted $R^{10}$ moieties together with the carbon atom on which they are attached form —C(O)—;

each $R^h$ is independently H, $C_1$-$C_3$ alkyl, $C_3$-$C_6$ cycloalkyl, —CH$_2$CO$_2$H, —CH$_2$C(O)NH$_2$, —S(O)$_2$—$C_1$-$C_3$ alkyl, or —S(O)$_2$—NH$_2$;

the subscript n5 is 0, 1, 2, or 3;

the subscript q is 0, 1, 2, 3, 4, or 5;

B. a group of the formula

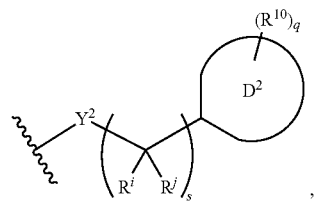

wherein $Y^2$ is a bond, —C(O)—, —N(R$^k$)—, —O—, —C(O)—N(R$^k$)—, —S(O)$_2$—N(R$^k$)—, or —N(R$^k$)—S(O)$_2$—;

$R^k$ is H or $C_1$-$C_3$ alkyl;

each $R^i$ is independently H, $C_1$-$C_3$ alkyl, hydroxyl, —CO$_2$H, or —N(H)C(O)NH$_2$;

each $R^j$ is independently H, $C_1$-$C_4$ alkyl, or cyclopropyl;

the subscript s is 0, 1, 2, 3, 4, or 5; and $D^2$ is selected from the group consisting of:

(i) a $C_3$-$C_{10}$ carbocycle, (ii) a 5- to 9-membered mono- or bicyclic heterocyclyl containing 1 or 3 heteroatoms selected from the group consisting of N, O, S, S(O), and S(O)$_2$; and (iii) a 5- to 6-membered heteroaryl containing 1 to 2 heteroatoms selected from the group consisting of N, O, and S;

C. a group of the formula

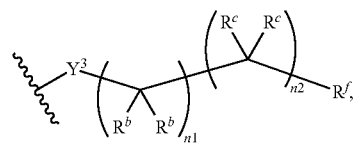

wherein $Y^3$ is (i) a bond, (ii)

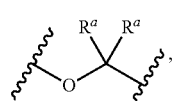

(iii)

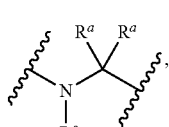

(iv)

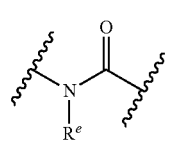

(v)

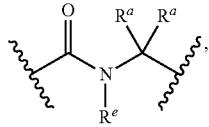

-continued (vi)
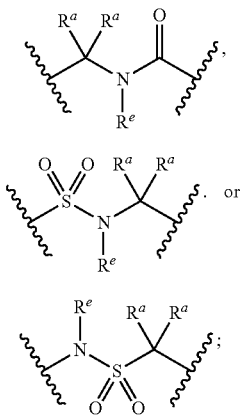

(vii)

(viii)

$R^e$ is H, $C_1$-$C_3$ alkyl, hydroxyl($C_2$-$C_3$) alkyl, or —(CH$_2$)$_{n3}$CN;

each $R^a$ is independently selected from the group consisting of H, fluoro, $C_1$-$C_6$ alkyl, and $C_1$-$C_3$ fluoroalkyl;

each $R^b$ is independently selected from the group consisting of H, hydroxyl, fluoro, $C_1$-$C_6$ alkyl, $C_1$-$C_3$ fluoroalkyl, hydroxy($C_1$-$C_3$) alkyl, —(CH$_2$)$_{n4}$—O—($C_1$-$C_3$) alkyl, —(CH$_2$)$_{n4}$C(O)NH$_2$, —(CH$_2$)$_{n4}$S—($C_1$-$C_3$) alkyl, and —(CH$_2$)$_{n4}$S(O)$_2$—($C_1$-$C_3$) alkyl;

each $R^e$ is independently H or $C_1$-$C_3$ alkyl;

$R^f$ is H, —CHF$_2$, —CF$_3$, —C(O)—($C_1$-$C_3$ alkyl), —CO$_2$R$^g$, —C(O)N(R$^h$)$_2$, —CN, hydroxyl, —N(R$^h$)$_2$, —SO$_3$H, —($C_1$-$C_3$) alkoxy, —O(CH$_2$)$_{n3}$OH;

the subscript n1 is 0, 1, 2, or 3;

the subscript n2 is 0 or 1;

each subscript n3 is independently 2 or 3;

each subscript n4 is independently 1, 2 or 3; and

D. a moiety selected from the group consisting of halo, —S—($C_1$-$C_3$ alkyl), and —S(O)$_2$—($C_1$-$C_3$ alkyl);

each $R^g$ is independently selected from the group consisting of:

(i) H;

(ii) $C_1$-$C_8$ alkyl;

(iii) a group of the formula -M-$R^{CH}$, wherein
  M is a bond or —(CH$_2$)$_{n6}$—, wherein the subscript n6 is 1 or 2;
  $R^{CH}$ is (a) aryl or $C_3$-$C_6$ cycloalkyl optionally substituted with 1-3 groups independently selected from halo, $C_1$-$C_4$ alkyl, or $C_1$-$C_4$ alkoxy; or (b) a 5- to 6-membered monocyclic heterocycle containing 1 or 2 heteroatoms independently selected from the group consisting of N and O, wherein said heterocycle of $R^{CH}$ is optionally substituted with 1 or 2 groups independently selected from the group consisting of oxo and $C_{1-3}$ alkyl;

(iv) a group of the formula —(CH$_2$)$_{n6}$—R$^m$ or —(CH$_2$)$_2$—O—(CH$_2$)$_2$—R$^m$ wherein R$^m$ is —CO$_2$R$^{m1}$, —C(O)N(R$^{m2}$)$_2$, or —O(CO)R$^{m1}$;

$R^{m1}$ is $C_1$-$C_4$ alkyl; and $R^{m2}$ is H or $C_1$-$C_4$ alkyl;

(v) a group of the formula —(CH$_2$)$_2$—R$^n$,
  R$^n$ is —OH, —O—($C_1$-$C_4$ alkyl), —O—(CH$_2$)$_2$—O—($C_1$-$C_4$ alkyl), —NH$_2$, —N(H)($C_1$-$C_4$ alkyl) or —N($C_1$-$C_4$ alkyl)$_2$;

(vi) a group of the formula

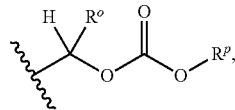

wherein
  $R^o$ is H or $C_1$-$C_4$ alkyl; and
  $R^p$ is $C_1$-$C_4$ alkyl, $C_3$-$C_6$ cycloalkyl, or phenyl; and, (vii) a group of the formula

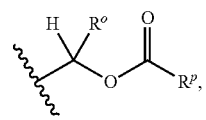

wherein $R^o$ and $R^p$ are as set forth above.

2. The compound of claim 1 or a pharmaceutically acceptable salt thereof, wherein $R^2$ is H.

3. The compound of claim 1 or a pharmaceutically acceptable salt thereof, wherein the subscript t is 1 or 2 and at least one $R^{cy}$ is a group of the formula

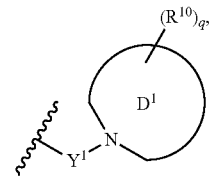

wherein $Y^1$, $D^1$, $R^{10}$, and q are as set forth in claim 1.

4. The compound of claim 1 or a pharmaceutically acceptable salt thereof, wherein t is 1 or 2 and at least one $R^{cy}$ is:
  a group of the formula

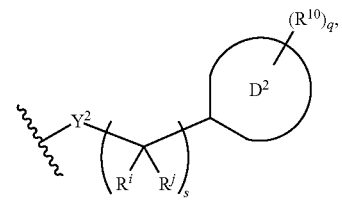

wherein $Y^2$, $D^2$, $R^i$, $R^j$, $R^{10}$, s and q are as set forth in claim 1.

5. The compound of claim 1 or a pharmaceutically acceptable salt thereof, wherein t is 1 or 2 and at least one $R^{cy}$ is a group of the formula

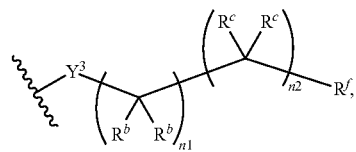

wherein $Y^3$, $R^b$, $R^c$, $R^f$, n1, and n2 are as set forth in claim 1.

6. The compound of claim 1 or a pharmaceutically acceptable salt thereof, having the Formula (IA)

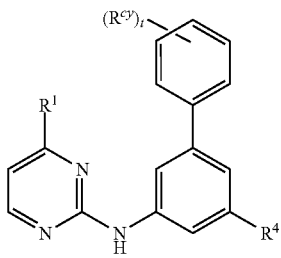

(IA)

wherein
R$^1$ is selected from the group consisting of C$_1$-C$_3$ alkyl, C$_1$-C$_3$ fluoroalkyl, and C$_3$-C$_6$ cycloalkyl;
R$^4$ is H or methyl;
the subscript t is 1 or 2; and
R$^{cy}$ is as set forth in claim 1.

7. The compound of claim 6 or a pharmaceutically acceptable salt thereof, wherein R$^1$ is —CF$_3$.

8. The compound of claim 6 or a pharmaceutically acceptable salt thereof, wherein at least one R$^{cy}$ is —CO$_2$H.

9. The compound of claim 8 or a pharmaceutically acceptable salt thereof, wherein the group

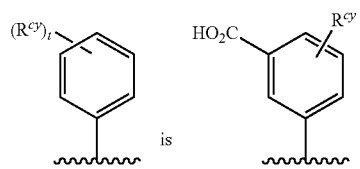

is

.

10. The compound of claim 1 or a pharmaceutically acceptable salt thereof, wherein the compound has the Formula (IB)

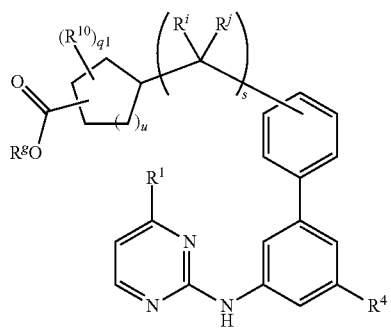

(IB)

wherein
R$^1$ is selected from the group consisting of C$_1$-C$_3$ alkyl, C$_1$-C$_3$ fluoroalkyl, and C$_3$-C$_6$ cycloalkyl;
R$^4$ is selected from the group consisting of H, C$_1$-C$_3$ alkyl and C$_1$-C$_3$ fluoroalkyl;
R$^i$ is H or hydroxyl;
R$^j$ is H or C$_1$-C$_3$ alkyl;
the subscript s is 0, 1, 2, or 3;
R$^{10}$ is C$_1$-C$_3$ alkyl or hydroxyl;
the subscript q1 is 0, 1, 2, or 3;
the subscript u is 0, 1 or 2; and
R$^g$ is as set forth in claim 1.

11. The compound of claim 10 or a pharmaceutically acceptable salt thereof,
wherein
R$^1$ is selected from the group consisting of methyl, —CF$_3$, and cyclopropyl;
R$^4$ is selected from the group consisting of H and methyl;
R$^i$ is H or hydroxyl;
R$^j$ is H or methyl;
the subscript s is 0 or 1; and
R$^{10}$ is methyl or hydroxyl.

12. The compound of claim 10 or a pharmaceutically acceptable salt thereof,
wherein the group

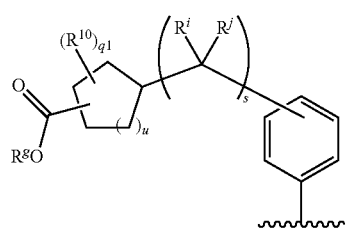

is a group of the formula

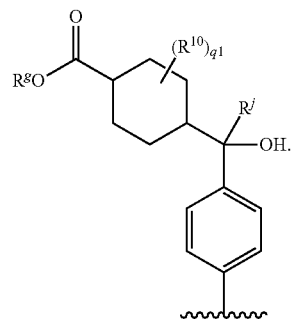

.

13. The compound of claim 1 or a pharmaceutically acceptable salt thereof, wherein R$^g$ is H or C$_1$-C$_3$ alkyl.

14. The compound of claim 1 or a pharmaceutically acceptable salt thereof, wherein the compound is selected from the group consisting of:
4-{[(3'-methyl-5'-{[4-(trifluoromethyl)pyrimidin-2-yl]amino}biphenyl-3-yl)sulfonyl]amino}benzoic acid;
4-methoxy-3'-methyl-5'-{[4-(trifluoromethyl)pyrimidin-2-yl]amino}biphenyl-3-carboxylic acid;
N-[(3'-methyl-5'-{[4-(trifluoromethyl)pyrimidin-2-yl]amino}biphenyl-3-yl)sulfonyl]-beta-alanine;
4-(2-fluoroethoxy)-3'-methyl-5'-{[4-(trifluoromethyl)pyrimidin-2-yl]amino}biphenyl-3-carboxylic acid;
4-{[(3'-methyl-5'-{[4-(trifluoromethyl)pyrimidin-2-yl]amino}biphenyl-3-yl)sulfonyl]amino}butanoic acid;
3'-methyl-4-(pyridin-3-ylmethoxy)-5'-{[4-(trifluoromethyl)pyrimidin-2-yl]amino}biphenyl-3-carboxylic acid;
3'-methyl-4-[(1-methyl-1H-imidazol-5-yl)methoxy]-5'-{[4-(trifluoromethyl)pyrimidin-2-yl]amino}biphenyl-3-carboxylic acid;
4-(4-hydroxybutoxy)-3'-methyl-5'-{[4-(trifluoromethyl)pyrimidin-2-yl]amino}biphenyl-3-carboxylic acid;
4-(3-hydroxypropoxy)-3'-methyl-5'-{[4-(trifluoromethyl)pyrimidin-2-yl]amino}biphenyl-3-carboxylic acid;

4-[(3-fluorobenzyl)oxy]-3'-methyl-5'-{[4-(trifluoromethyl)pyrimidin-2-yl]amino}biphenyl-3-carboxylic acid;
4-(cyclopropylmethoxy)-3'-methyl-5'-{[4-(trifluoromethyl)pyrimidin-2-yl]amino}biphenyl-3-carboxylic acid;
4-(benzyloxy)-3'-methyl-5'-{[4-(trifluoromethyl)pyrimidin-2-yl]amino}biphenyl-3-carboxylic acid;
4-(cyclohexyloxy)-3'-methyl-5'-{[4-(trifluoromethyl)pyrimidin-2-yl]amino}biphenyl-3-carboxylic acid;
3'-methyl-4-(2-methylpropoxy)-5'-{[4-(trifluoromethyl)pyrimidin-2-yl]amino}biphenyl-3-carboxylic acid;
trans-4-[1-hydroxy-1-(3'-methyl-5'-{[4-(trifluoromethyl)pyrimidin-2-yl]amino}biphenyl-4-yl)ethyl]cyclohexanecarboxylic acid;
(1R)-trans-4-[1-hydroxy-1-(3'-methyl-5'-{[4-(trifluoromethyl)pyrimidin-2-yl]amino}biphenyl-4-yl)ethyl]cyclohexanecarboxylic acid;
(1S)-trans-4-[1-hydroxy-1-(3'-methyl-5'-{[4-(trifluoromethyl)pyrimidin-2-yl]amino}biphenyl-4-yl)ethyl]cyclohexanecarboxylic acid;
3'-methyl-5'-{[4-(trifluoromethyl)pyrimidin-2-yl]amino}biphenyl-3-carboxylic acid;
5-cyano-3'-methyl-5'-{[4-(trifluoromethyl)pyrimidin-2-yl]amino}biphenyl-3-carboxylic acid;
5-fluoro-3'-methyl-5'-{[4-(trifluoromethyl)pyrimidin-2-yl]amino}biphenyl-3-carboxylic acid;
3-{3'-[(4-cyclopropylpyrimidin-2-yl)amino]-5'-methylbiphenyl-4-yl}propanoic acid;
4-chloro-3'-methyl-5'-{[4-(trifluoromethyl)pyrimidin-2-yl]amino}biphenyl-3-carboxylic acid;
4-amino-3'-methyl-5'-{[4-(trifluoromethyl)pyrimidin-2-yl]amino}biphenyl-3-carboxylic acid;
3''-methyl-5''-{[4-(trifluoromethyl)pyrimidin-2-yl]amino}-1,1':4',1''-terphenyl-2'-carboxylic acid;
3'-[(4-methoxypyrimidin-2-yl)amino]-5'-methylbiphenyl-3-carboxylic acid;
N-(4'-[(1R)-2,2-difluoro-1-hydroxyethyl]-5-{[4-(trifluoromethyl)pyrimidin-2-yl]amino}biphenyl-3-yl)acetamide;
3-{3'-[(4-cyclopropylpyrimidin-2-yl)amino]-5'-methylbiphenyl-3-yl}propanoic acid;
trans-4-(1-hydroxy-1-{3'-methyl-5'-[(4-methylpyrimidin-2-yl)amino]biphenyl-4-yl}ethyl)cyclohexanecarboxylic acid;
(1R)-trans-4-(1-hydroxy-1-{3'-methyl-5'-[(4-methylpyrimidin-2-yl)amino]biphenyl-4-yl}ethyl)cyclohexanecarboxylic acid;
(1S)-trans-4-(1-hydroxy-1-{3'-methyl-5'-[(4-methylpyrimidin-2-yl)amino]biphenyl-4-yl}ethyl)cyclohexanecarboxylic acid;
5-cyano-3'-{[4-(trifluoromethyl)pyrimidin-2-yl]amino}biphenyl-3-carboxylic acid;
3-(3'-methyl-5'-{[4-(trifluoromethyl)pyrimidin-2-yl]amino}biphenyl-4-yl)propanoic acid;
3-(3'-methyl-5'-{[4-(trifluoromethyl)pyrimidin-2-yl]amino}biphenyl-3-yl)propanoic acid;
3-(3'-methyl-5'-{[4-(trifluoromethyl)pyrimidin-2-yl]amino}biphenyl-4-yl)propanoic acid;
5-fluoro-3'-{[4-(trifluoromethyl)pyrimidin-2-yl]amino}biphenyl-3-carboxylic acid;
3-(3'-methyl-5'-{[4-(trifluoromethyl)pyrimidin-2-yl]amino}biphenyl-3-yl)propanoic acid;
3-{3'-[(4-methoxypyrimidin-2-yl)amino]-5'-methylbiphenyl-3-yl}propanoic acid;
1-(4'-[(1R)-2,2-difluoro-1-hydroxyethyl]-5-{[4-(trifluoromethyl)pyrimidin-2-yl]amino}biphenyl-3-yl)-3-ethylurea; and
(1R)-1-(3'-Amino-5'-{[4-(trifluoromethyl)pyrimidin-2-yl]amino}biphenyl-4-yl)-2,2-difluoroethanol.

15. A pharmaceutical composition comprising a therapeutically effective amount of the compound of claim 1 or a pharmaceutically acceptable salt thereof and a pharmaceutically acceptable carrier.

16. The pharmaceutical composition of claim 15, further comprising an additional therapeutic agent.

17. The compound of claim 10 or a pharmaceutically acceptable salt thereof, wherein $R^g$ is H or $C_1$-$C_3$ alkyl.

18. The compound of claim 11 or a pharmaceutically acceptable salt thereof, wherein $R^g$ is H or $C_1$-$C_3$ alkyl.

19. The compound of claim 12 or a pharmaceutically acceptable salt thereof, wherein $R^g$ is H or $C_1$-$C_3$ alkyl.

* * * * *